US007902205B2

(12) United States Patent
Xue et al.

(10) Patent No.: US 7,902,205 B2
(45) Date of Patent: Mar. 8, 2011

(54) PURINONE DERIVATIVES AS HM74A AGONISTS

(75) Inventors: Chu-Biao Xue, Hockessin, DE (US); Brian Metcalf, Moraga, CA (US); Anlai Wang, Wilmington, DE (US); Changsheng Zheng, Wilmington, DE (US); Ganfeng Cao, Bear, DE (US); Ke Zhang, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 174 days.

(21) Appl. No.: 12/237,794

(22) Filed: Sep. 25, 2008

(65) Prior Publication Data

US 2009/0088446 A1 Apr. 2, 2009

Related U.S. Application Data

(63) Continuation of application No. 11/766,990, filed on Jun. 22, 2007, now Pat. No. 7,462,624.

(60) Provisional application No. 60/922,924, filed on Apr. 11, 2007, provisional application No. 60/815,935, filed on Jun. 23, 2007.

(51) Int. Cl.
*A01N 43/54* (2006.01)
*A61K 31/505* (2006.01)
*C07D 491/00* (2006.01)
(52) U.S. Cl. .................................. 514/267; 544/251
(58) Field of Classification Search .................. 514/267; 544/251
See application file for complete search history.

(56) References Cited

U.S. PATENT DOCUMENTS

| 4,404,380 | A | 9/1983 | Temple, Jr. |
| 6,902,902 | B2 | 6/2005 | Unett et al. |
| 7,462,624 | B2 * | 12/2008 | Xue et al. .................. 514/267 |
| 7,511,050 | B2 | 3/2009 | Zheng et al. |
| 2004/0254224 | A1 | 12/2004 | Foord et al. |
| 2005/0004178 | A1 | 1/2005 | Unett et al. |
| 2006/0078916 | A1 | 4/2006 | Aguilar et al. |
| 2006/0160132 | A1 | 7/2006 | Golz et al. |

FOREIGN PATENT DOCUMENTS

| EP | 417790 | 3/1991 |
| EP | 1092435 | 4/2001 |
| EP | 1251130 | 10/2002 |
| WO | WO 90/01031 | 2/1990 |
| WO | WO 1998/056820 | 12/1998 |
| WO | WO 00/01388 | * 1/2000 |
| WO | WO 01/47931 | 7/2001 |
| WO | WO 2002/00196 | 1/2002 |
| WO | WO 02/44182 | 6/2002 |
| WO | WO 2002/084298 | 10/2002 |
| WO | WO 03/022284 | 3/2003 |
| WO | WO 2004/071378 | 8/2004 |
| WO | WO 2005/077950 | 8/2005 |
| WO | WO 2006/021892 | 3/2006 |
| WO | WO 2006/045564 | 5/2006 |
| WO | WO 2006/045565 | 5/2006 |
| WO | WO 2007/017261 | 2/2007 |
| WO | WO 2007/017262 | 2/2007 |
| WO | WO 2007/017265 | 2/2007 |

OTHER PUBLICATIONS

U.S. Appl. No. 12/237,807, filed Sep. 25, 2008, Xue et al.
U.S. Appl. No. 12/263,990, filed Nov. 3, 2008, Xue et al.
Altschul, et al., "Influence of nicotinic acid on serum cholesterol in man", *Arch. Biochem*, 1955, 54:558-559.
Blom, K.F., et al., "Preparative LC-MS purification: improved compound-specific method optimization", *J. Comb. Chem.*, 2004, 6:874-883.
Aktories, K., et al., "Nicotinic acid inhibits adipocyte adenylate cyclase in a hormone-like mannter" *FEBS Letters*, 1980, 115:11-14.
Aktories, K., et al., "Islet-activating protein prevent nicotinic acid-induced GTPase stimulation and GTP but not GTP gamma S-induced adenylate cyclase inhibition in rat adipocytes", *FEBS Letters*, 1983, 156:88-92.
Defronzo, R.A., "Dysfunctional fat cells, lipotoxicity and type 2 diabetes", *Int. J. Clin. Prac.* 2004, 58:9-21.
Higuchi, T. et al., "Pro-drugs as Novel Delivery Systems", vol. 14 of the A.C.S. Symposium Series.
Lorenzen, A., et al., "Characterization of a G Protein-Coupled Receptor for Nicotinic Acid", *Mol. Pharm*, 2001, 59:349-357.
Nicolaou, K.C. et al., "Lipoxins and related eicosanoids: Biosynthesis, Biological Properties, and Chemical Synthesis", *Angnew. Chem., Int. Engl.*, 1991, 30:1100.
Sonogashira, K., et al., ., "A convenienet synthesis of acetylenes: catalytic substitutions of acetylenic hydrogen with bromoalkenes, iodoarenes and bromopyridines", *Tetrahedron Letters*, 1975, p. 4467.
Taylor, A. et al., ., "Arterial Biology for the Investigation of the Treatment Effects of Reducing Cholesterol (ARBITER) 2: A Double-Blind, Placebo-Controlled Study of Extended-Release Niacin on Atherosclerosis Progression in Secondary Prevention Patients Treated with Statins", *Circulation*, 2004, 110:3512-3517.
Tunaru, S., et al., "PUMA-G and HM74 are receptors for nicotinic acid and mediate its antilipolytic effect", *Nat. Med.*, , 2003, 9:352-355.
Wise, et al., "Molecular Identification of High and Low Affinity Receptors for Nicotinic Acid", *J. Biol. Chem.*, 2003, 278:9869-9874.
Various contributors to Nature Medicine special focus on atherosclerosis , *Nature Med.*, 2002, 8:1209-1262.
Linton, M.F., et al., *NCEP ATP III, Am. J. Cardio.*, 2003, 92:19i-26i.
Garcia-Calvo, M. et al., The target of ezetimibe is Niemann-Pick C1-Like 1 (NPC1L1), , *PNAS*, 2005, 102:8132-8137.
*Remington's Pharmaceutical Sciences*, 17th ed., Mack Publishing Company, Easton, PA., p. 1418.
*Journal of Pharmaceutical Science*, 66, 2, 1977.
*Bioreversible Carriers in Drug Design*, Edward B. Roche, ed., American Pharmaceutical Associateion and Pergamon Press, 1987.

(Continued)

*Primary Examiner* — James O Wilson
*Assistant Examiner* — Erich A Leeser
(74) *Attorney, Agent, or Firm* — Pepper Hamilton LLP

(57) ABSTRACT

The present invention relates to purinone derivatives which are agonists of the HM74a receptor. Further provided are compositions and methods of using the compounds herein, and their pharmaceutically acceptable salts for the treatment of disease.

36 Claims, No Drawings

OTHER PUBLICATIONS

Green et al., *Protective Groups in Organic Synthesis*, 2nd ed., Wiley and Sons, 1991.

Temple, D.L., et al., Substituted 6,7-dihydroimidazo[1,2-a]purin-9(4H)-ones, *Journal of Medicinal Chemistry*, 23(11), 1188-98, 1980.

Mueller, C., et al., "Imidazo[2,1,1]purin-5-ones and Related Tricyclic Water-Soluble Purine Derivatives: Potent AZA-and A3-Adenosine Receptor Antagonists", *Journal of Medicinal Chemistry*, 45(16), 3440-3450, 2002.

Notice of Co-Pending Applications.

Notice of Allowance dated Aug. 19, 2010 received in copending U.S. Appl. No. 12/237,807.

Office Action dated Oct. 19, 2010 received in copending U.S. Appl. No. 12/263,990.

Wolff, Manfred E., Burger's Medicinal Chemistry and Drug Discovery, Fifth Ed., vol. 1: Principles and Practice, John Wiley & Sons, 1995, p. 975-977.

Banker et al., Modern Pharmaceutics, Marcel Dekker, New York, 1996, p. 451, p. 596.

* cited by examiner

PURINONE DERIVATIVES AS HM74A AGONISTS

This application is a continuation of U.S. patent application Ser. No. 11/766,990, filed on Jun. 22, 2007, now pending, which in turn claims benefit of priority to U.S. provisional patent application Ser. No. 60/815,935 filed Jun. 23, 2006, and to U.S. provisional patent application Ser. No. 60/922,924 filed Apr. 11, 2007, the disclosure of each of these three applications is hereby incorporated by reference in its entirety.

FIELD OF THE INVENTION

The present invention relates to agonists of the HM74a receptor, compositions thereof and methods of using the same.

BACKGROUND OF THE INVENTION

Coronary artery disease (or CAD) is the number one cause of death in the United States (Nature Med 2002, 8:1209-1262). The initiation and progression of CAD involves a complex interplay between multiple physiological processes, including inflammation, lipid homeostasis, and insulin resistance/diabetes mellitus. Multiple clinical studies have now shown that the three primary components of plasma lipids, low-density lipoprotein (or LDL), high-density lipoproteins (or HDL), and triglycerides (or TGs), are causally associated with the propensity to develop atherosclerosis and CAD. Along side other risk factors such as positive family history of CAD, elevated body-mass index, hypertension, and insulin resistance/diabetes mellitus, elevated plasma LDL and/or TG-rich lipoproteins and decreased plasma HDL levels have been defined as major cardiovascular risk factors by the National Cholesterol Education Program Adult Treatment Panel III (NCEP ATP III; Am J Cardio 2003, 92: 19i-26i). Accordingly, therapeutic intervention strategies designed to impact these plasma lipid components as well as those that underlie insulin resistance are of great interest to the medical community.

In terms of LDL-lowering, drugs of the statin class are structurally similar to the molecule hydroxymethylglutaryl-coenzyme A (HMG-CoA), a biosynthetic precursor of cholesterol. These drugs are competitive inhibitors of the rate-limiting step of cholesterol biosynthesis catalyzed by HMG-CoA reductase. Mechanistically, the statins lower LDL by upregulating the LDL receptor in the liver as well as by reducing the release of LDL into the circulation. As a monotherapy, the statin class of lipid lowering agents can reduce plasma LDL concentrations by 30-60% and triglycerides by 25%, producing a reduction in the incidence of CAD by 25-60% and the risk of death by 30%. Statins do not have an appreciable effect on HDL. A mechanistically distinct agent, Ezetimibe (Zetia, Merck and Co.), also possesses the ability to reduce plasma LDL, however it functions by inhibiting the absorption of cholesterol by the small intestine via antagonism of the NPC1L1 receptor (PNAS 2005, 102: 8132-8137). Monotherapy with Ezetimibe typically lowers LDL by 20%, however when co-formulated with a statin, maximal reductions can exceed 60%. As with the statins, however, Ezetimibe has a negligible effect on plasma HDL.

While statins can have a modest impact on circulating triglycerides, PPAR alpha agonists (or fibrates) are far superior in targeting this lipid endpoint. The fibrates function by increasing lipolysis and elimination of triglyceride-rich particles from plasma by activating lipoprotein lipase and reducing production of apolipoprotein C-III (an inhibitor of lipoprotein lipase activity). One such fibrate, Fenofibrate (Tricor, Abott), has been shown in clinical studies to decrease plasma triglyceride levels upwards of 40-60%. Interestingly, the fibrate class of lipid-lowering drugs also has a modest, but significant effect on both LDL (20% reduction) and HDL (10% increase).

Currently, the statin class of LDL lowering agents remains the cornerstone of dyslipidemia therapy. Despite the substantial reduction in cardiovascular events that have been achieved with this therapeutic approach, however, the cardio-protection that is afforded to patients by these therapies is still incomplete. It is now clear that therapies that are targeted to increase HDL cholesterol are critical in terms of maximizing patient cardio-protection. The only therapy available to date that has the ability to effectively raise circulating levels of cardio-protective HDL and consequently improve the progression of atherosclerosis in CAD patients is nicotinic acid (niacin or vitamin $B_3$). Nicotinic acid was first reported to modify lipoprotein profiles in 1955 (Altschul et al. Arch Biochem Biophys 1955, 54: 558-559). Its effects are the most broad-spectrum of any available therapy, effectively raising HDL levels (20-30%) as well as lowering circulating plasma LDL (16%) and triglycerides (38%). The clinical significance of this broad-spectrum activity has been revealed in multiple large clinical studies. In the most recent ARBITER 2 (Arterial Biology for the Investigation of the Treatment Effects of Reducing Cholesterol 2; Taylor et al. Circulation 2004, 110: 3512-3517) study, patients on statin therapy were randomized to either placebo or 1000 mg extended release (ER) niacin (Niaspan, Kos Pharmaceuticals). Patients receiving niacin exhibited a statistically significant decrease in carotid intima-media thickness, a validated surrogate cardiovascular end point. This study also revealed a significantly reduced rate of intima-media thickness progression in subjects without detectable insulin resistance. This study indicates the incomplete cardio-protection that is offered by statin therapy and substantiates the utility of nicotinic acid in reducing overall cardiac risk in low-HDL patients.

While nicotinic acid has been used clinically to modify lipid profiles for over four decades, the mechanism of action of the compound has remained largely obscure. It has long been known that acute nicotinic acid dosing results in a profound decrease in circulating free fatty acids (FFAs). This anti-lipolytic activity was first hypothesized in 1980 to be mediated by a membrane receptor linked to a decrease in intracellular cAMP (cyclic AMP, or cyclic adenosine monophosphate, or 3'-5'-cyclic adenosine monophosphate) levels (Aktories et al. FEBS Letters 1980, 115: 11-14). This hypothesis was later confirmed and the implied $G_{i/o}$ GPCR-coupling was verified using pertussis toxin sensitivity studies (Aktories et al. FEBS Letters 1983, 156: 88-92). The identification of specific nicotinic acid binding sites on the surface of adipose and spleen cells confirmed the membrane hypothesis and refined, using modern-day techniques, the G-protein coupling of the receptor itself (Lorenzen et al. Mol Pharm 2001, 59: 349-357). This G-protein mediated, anti-lipolytic activity of nicotinic acid was used for two decades to identify and characterize nicotinic acid analogues in terms of their therapeutic potential. Finally, in 2003, two independent groups simultaneously published the cloning of an orphan $G_{i/o}$-coupled GPCR, HM74a (Wise et al. J Biol Chem 2003, 278: 9869-9874; Tunaru et al. Nat Med 2003, 9: 352-355), which binds to nicotinic acid with high affinity. As predicted, this receptor was shown to be expressed in adipose tissue and spleen, and binds to not only nicotinic acid, but also to the structurally related derivatives that had been previously shown to exhibit adipocyte anti-lipolytic activity. Mice that have been made deficient in the rodent ortholog of HM74a (Puma-g) by homologous recombination resist nicotinic acid-dependent FFA reduction and TG lowering. It is currently hypothesized that the nicotinic acid anti-lipolytic activity is based on the activation of this high affinity GPCR (HM74a), resulting in a decrease in intracellular cAMP and a subsequent attenuation of hormone sensitive lipase (HSL) activity. Decreased adipocyte lipolytic output results in a reduction in circulating FFA and a corresponding reduction in hepatic TGs, very-low density LDL (VLDL), and LDL. The increased levels of HDL arise from an effective reduction of cholesterol ester transfer protein activity due to decreased availability of VLDL acceptor molecules.

Beyond impacting lipid levels and lipoprotein profiles, FFAs play fundamental roles in the regulation of glycemic control. It is now recognized that chronically elevated plasma FFA concentrations cause insulin resistance in muscle and liver, and impair insulin secretion (reviewed in Defronzo et al. Int. J. Clin. Prac. 2004, 58: 9-21). In muscle, acute elevations in plasma FFA concentrations can increase intramyocellular lipid content; this can have direct negative effects on insulin receptor signaling and glucose transport. In liver, increased plasma FFAs lead to accelerated lipid oxidation and acetyl-CoA accumulation, the later of which stimulates the rate-limiting steps for hepatic glucose production. In the pancreas, long-term exposure to elevated FFAs has been shown to impair the beta-cell's ability to secrete insulin in response to glucose. This data has driven the hypothesis that adipose tissue FFA release is a primary driver of the underlying pathologies in type 2 diabetes, and strategies designed to reduce FFAs, for example by agonizing HM74A, may prove effective in improving insulin sensitivity and lowering blood glucose levels in patients with type 2 diabetics/metabolic syndrome The utility of nicotinic acid as a hypolipidemic/FFA lowering agent is currently limited by four main factors. First, significant doses of nicotinic acid are required to impact FFA release and improve lipid parameters. Immediate release (IR) nicotinic acid is often dosed at 3-9 g/day in order to achieve efficacy, and ER nicotinic acid (Niaspan) is typically dosed between 1-2 g/day. These high doses drive the second issue with nicotinic acid therapy, hepatotoxicity. One of the main metabolic routes for nicotinic acid is the formation of nicotinamide (NAM). Increased levels of NAM have been associated with elevated liver transaminase which can lead to hepatic dysfunction. This toxicity is particularly problematic for sustained release formulations and results in the need to monitor liver enzymes during the initiation of therapy. Third, high doses of nicotinic acid are associated with severe prostaglandin-mediated cutaneous flushing. Virtually all patients experience flushing when on IR-nicotinic acid at or near the $T_{max}$ of the drug and discontinuation of therapy occurs in 20-50% of individuals. Niaspan, while exhibiting an increased dissolution time, still possesses a flushing frequency of approximately 70%, and this is in spite of the recommended dosing regimen that includes taking Niaspan along with an aspirin after a low-fat snack. Fourth, nicotinic acid therapy often results in FFA rebound, a condition whereby free fatty acid levels are not adequately suppressed throughout the dosing regimen, resulting in a compensatory increase in adipose tissue lipolysis. With immediate release nicotinic acid therapy, this rebound phenomenon is so great that daily FFA AUCs are actually increased after therapy. Such FFA excursions can lead to impaired glycemic control and elevated blood glucose levels, both of which have been shown to occur in some individuals after nicotinic acid therapy.

Giving the importance of nicotinic acid in modulating (especially agonizing) HM74a receptor and its limitations, novel small molecules designed to mimic the mechanism of nicotinic acid's action on HM74a offer the possibility of achieving greater HDL, LDL, TG, and FFA efficacy while avoiding adverse effects such as hepatotoxicity and cutaneous flushing. Such therapies are envisioned to have significant impact beyond dyslipidemia to include insulin resistance, hyperglycemia, and associated syndromes by virtue of their ability to more adequately reduce plasma FFA levels during the dosing interval. The present invention is directed to these, as well as other, important ends.

SUMMARY OF THE INVENTION

The present invention provides, inter alia, compounds of Formula I:

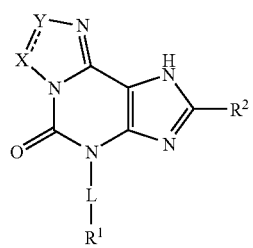

or pharmaceutically acceptable salts or prodrugs thereof, wherein constituent members are defined herein.

The present invention further provides compositions comprising a compound of the invention and at least one pharmaceutically acceptable carrier.

The present invention further provides methods of modulating HM74a receptor with a compound of the invention.

The present invention further provides methods of agonizing HM74a receptor by contacting the HM74a receptor with a compound of the invention.

The present invention further provides methods of treating diseases associated with HM74a receptor.

The present invention further provides a compound of the invention for use in therapy.

The present invention further provides a compound of the invention for use in the preparation of a medicament for use in therapy.

DETAILED DESCRIPTION

The present invention provides, inter alia, compounds which are agonists or partial agonists of HM74a and are useful in the treatment of a variety of diseases, such as cardiovascular diseases. The compounds can have Formula I:

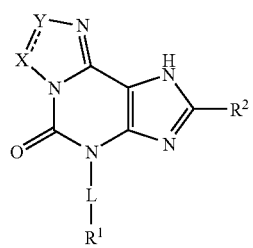

or are pharmaceutically acceptable salt or prodrug thereof, wherein:
  a dashed line indicates an optional bond;
  X is N, $CR^{3a}$, $CR^{4a}R^{5a}$, or $NR^{6a}$;
  Y is N, $CR^{3b}$, $CR^{4b}R^{5b}$, or $NR^{6b}$;

L is —($C_{1-6}$ alkylene)-$(Q^1)_m$-($C_{1-6}$ alkylene)$_p$-$(Q^2)_q$-($C_{1-6}$ alkylene)$_r$- optionally substituted by 1, 2, 3, 4, or 5 $R^{L1}$, wherein if m and q are both 1, then p is 1;

$R^1$ is H, $C_{1-10}$ alkyl, $C_{2-10}$ alkenyl, $C_{2-10}$ alkynyl, or Cy, wherein said $C_{1-10}$ alkyl, $C_{2-10}$ alkenyl, or $C_{2-10}$ alkynyl is optionally substituted with 1, 2, 3, 4, or 5 $R^{L2}$;

$R^2$ is halo, cyano, $C_1$ haloalkyl, or acetylenyl, wherein said acetylenyl is optionally optionally substituted by a substitutent selected from $C_{1-6}$ alkyl, $C_{2-6}$ alkenyl, $C_{2-10}$ alkynyl, $C_{1-6}$ haloalkyl, $C_{1-6}$ hydroxyalkyl, $C_{1-6}$ cyanoalkyl, $Cy^4$, CN, $NO_2$, $C(O)R^{b6}$, $C(O)NR^{c6}R^{d6}$, or $C(O)OR^{a6}$;

$R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^e$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$;

$R^{4a}$, $R^{4b}$, $R^{5a}$, and $R^{5b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substituents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{6a}$ and $R^{6b}$ are independently selected from H, $C_{1-6}$ alkyl, $C_{2-6}$ alkenyl, $C_{2-6}$ alkynyl, $C_{1-6}$ haloalkyl, $Cy^2$, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substituents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{L1}$ and $R^{L2}$ are independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $C(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

Cy is aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$;

$Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $-(L^B)_{t1}-Cy^3$, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, and $S(O)_2NR^{c4}R^{d4}$;

$Cy^3$ and $Cy^4$ are independently selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^6$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

$Q^1$ and $Q^2$ are independently selected from O, S, NH, $CH_2$, CO, CS, SO, $SO_2$, $OCH_2$, $SCH_2$, $NHCH_2$, $CH_2CH_2$, $COCH_2$, CONH, COO, $SOCH_2$, SONH, $SO_2CH_2$, and $SO_2NH$;

$R^a$ and $R^{a1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{a2}$, $R^{a3}$, $R^{a4}$, $R^{a5}$, and $R^{a6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^b$ and $R^{b1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{b2}$, $R^{b3}$, $R^{b4}$, $R^{b5}$, and $R^{b6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^c$ and $R^d$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^c$ and $R^d$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c1}$ and $R^{d1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^{c1}$ and $R^{d1}$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$ and $S(O)_2NR^{c5}R^{d5}$;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c2}$ and $R^{d2}$ together with the N atom to which they are attached form a 4-, 5-, 6- or 7-membered heterocycloalkyl group;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c3}$ and $R^{d3}$ together with the N atom to which they are attached form a 4-, 5-, 6- or 7-membered heterocycloalkyl group;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c4}$ and $R^{d4}$ together with the N atom to which they are attached form a 4-, 5-, 6- or 7-membered heterocycloalkyl group;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c5}$ and $R^{d5}$ together with the N atom to which they are attached form a 4-, 5-, 6- or 7-membered heterocycloalkyl group;

$R^{c6}$ and $R^{d6}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c6}$ and $R^{d6}$ together with the N atom to which they are attached form a 4-, 5-, 6- or 7-membered heterocycloalkyl group;

$L^B$ is $C_{1-4}$ alkylene optionally substituted with 1, 2, 3, 4 or 5 substituents independently selected from OH, halo, —O—($C_{1-4}$ alkyl), —O—($C_{1-4}$ haloalkyl), and amino; t1 is 0 or 1; and m, p, q, and r are independently selected from 0 and 1.

In some embodiments, when X=Y is $CR^{4a}R^{5a}$—$CR^{4b}R^{5b}$, then -L-$R^1$ is other than $C_{1-3}$ alkyl.

In some embodiments, X=Y is other than $CR^{4a}R^{5a}$—$CR^{4b}R^{5b}$.

In some embodiments, $R^2$ is halo, cyano, $C_1$ haloalkyl, or acetylenyl.

In some embodiments, $R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl are optionally substituted with 1, 2, or 3 substitutents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, $Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, and $S(O)_2NR^{c4}R^{d4}$.

In some embodiments, X is N.
In some embodiments, X is $CR^{3a}$.
In some embodiments, X is CH.
In some embodiments, X is C-Me.
In some embodiments, X is $CR^{4a}R^{5a}$.
In some embodiments, Y is N.
In some embodiments, Y is $CR^{3b}$.
In some embodiments, Y is CH. In some embodiments, Y is C-Me.
In some embodiments, Y is $CR^{4b}R^{5b}$.
In some embodiments, X is $NR^{6a}$ and Y is $CR^{4b}R^{5b}$.
In some embodiments, X is $CR^{4a}R^{5a}$ and Y is $NR^{6b}$.
In some embodiments, X is $NR^{6a}$ and Y is $NR^{6b}$.
In some embodiments, X is N and Y is N.
In some embodiments, X is $CR^{3a}$ and Y is N.
In some embodiments, X is N and Y is $CR^{3b}$.

In some embodiments, $R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, $S(O)R^b$, $S(O)_2R^b$, and $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, $R^{3a}$ and $R^{3b}$ are independently selected from H, $C_{1-6}$ alkyl, $C_{1-6}$ haloalkyl, $Cy^1$, $OR^a$, $SR^a$, $S(O)R^b$, $S(O)_2R^b$, and $NR^cR^d$, wherein said $C_{1-6}$ alkyl is optionally substituted with 1, 2, or 3 substituents independently selected from $Cy^1$, $C(O)NR^cR^d$, $C(O)OR^a$, halo, $OR^a$, $NR^cR^d$, $NR^cC(O)NR^cR^d$, and $NR^cC(O)R^b$.

In some embodiments, $R^{3a}$ and $R^{3b}$ are independently selected from H, halo, $C_{1-6}$ alkyl, $C_{2-6}$ alkenyl, $C_{2-6}$ alkynyl, and $C_{1-6}$ haloalkyl.

In some embodiments, $R^{3a}$ and $R^{3b}$ are independently selected from H, halo, $C_{1-6}$ alkyl, $C_{2-6}$ alkenyl, $C_{2-6}$ alkynyl, and $C_{1-6}$ haloalkyl.

In some embodiments, $R^{3a}$ and $R^{3b}$ are independently selected from H, halo, and $C_{1-4}$ alkyl. In some further embodiments, $R^{3a}$ and $R^{3b}$ are independently selected from H and $C_{1-4}$ alkyl. In yet further embodiments, $R^{3a}$ and $R^{3b}$ are independently $C_{1-4}$ alkyl.

In some embodiments:
at least one of $R^{3a}$ and $R^{3b}$ is selected from $Cy^1$;
$Cy^1$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $-(L^B)_{t1}$-$Cy^3$, $OR^{a4}$, $SR^{a4}$, $C(O)R^{a4}$, $C(O)NR^{c4}R^{d4}$, and $C(O)OR^{a4}$; and
$Cy^3$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:
$R^{3a}$ or $R^{3b}$ is $Cy^1$;
$Cy^1$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $-(L^B)_{t1}$-$Cy^3$, $OR^{a4}$, $SR^{a4}$, $C(O)R^{b4}$, $C(O)NR^{c4}R^{d4}$, and $C(O)OR^{a4}$; and
$Cy^3$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$ and $SR^{a6}$.

In some embodiments:
one of $R^{3a}$ and $R^{3b}$ is selected from $Cy^1$;
$Cy^1$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $-(L^B)_{t1}$-$Cy^3$, $OR^{a4}$, $SR^{a4}$, $C(O)R^{b4}$, $C(O)NR^{c4}R^{d4}$, and $C(O)OR^{a4}$; and
$Cy^3$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:
one of $R^{3a}$ and $R^{3b}$ is $Cy^1$;
$Cy^1$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $-(L^B)_{t1}$-$Cy^3$, $OR^{a4}$, $SR^{a4}$, $C(O)R^{b4}$, $C(O)NR^{c4}R^{d4}$, and $C(O)OR^{a4}$; and
$Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, one of $R^{3a}$ and $R^{3b}$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^{c4}R^{d4}$, and $C(O)OR^{a4}$.

In some embodiments:
one of $R^{3a}$ and $R^{3b}$ is $Cy^1$;
$Cy^1$ is selected from aryl and heteroaryl, each substituted with $-(L^B)_{t1}$-$Cy^3$ and optionally substituted with 1, 2 or 3 substituents independently selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^{c4}R^{d4}$, and $C(O)OR^{a4}$; and
$Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:
one of $R^{3a}$ and $R^{3b}$ is $Cy^1$;
$Cy^1$ is selected from aryl and heteroaryl, each substituted with $-(L^B)$-$Cy^3$ and optionally substituted with 1, 2 or 3 substituents independently selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^{c4}R^{d4}$, and $C(O)OR^{a4}$; and
$Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:
one of $R^{3a}$ and $R^{3b}$ is $Cy^1$;
$Cy^1$ is selected from aryl and heteroaryl, each substituted with $-Cy^3$ and optionally substituted with 1, 2 or 3 substituents independently selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^{c4}R^{d4}$, and $C(O)OR^{a4}$; and
$Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, at least one of $R^{3a}$ and $R^{3b}$ is selected from $C_{1-6}$ alkyl and $C_{1-6}$ haloalkyl, wherein said $C_{1-6}$ alkyl is optionally substituted with 1, 2, or 3 substituents independently selected from halo, $OR^a$, $C(O)NR^cR^d$, $C(O)OR^a$, $NR^cR^d$, $NR^cC(O)NR^cR^d$, and $NR^cC(O)R^b$. In some embodiments, one of $R^{3a}$ and $R^{3b}$ is selected from $C_{1-6}$ alkyl and $C_{1-6}$ haloalkyl, wherein said $C_{1-6}$ alkyl is optionally substituted with 1, 2, or 3 substituents independently selected from halo, $OR^a$, $C(O)NR^cR^d$, $C(O)OR^a$, $NR^cR^d$, $NR^cC(O)NR^cR^d$, and $NR^cC(O)R^b$.

In some embodiments, at least one of $R^{3a}$ and $R^{3b}$ is selected from $C_{1-6}$ alkyl and $C_{1-6}$ haloalkyl, wherein said $C_{1-6}$ alkyl is optionally substituted with 1, 2, or 3 substituents independently selected from OH, —O—($C_{1-4}$ alkyl) and —O—$C_{1-4}$ haloalkyl. In some embodiments, one of $R^{3a}$ and $R^{3b}$ is selected from $C_{1-6}$ alkyl and $C_{1-6}$ haloalkyl, wherein said $C_{1-6}$ alkyl is optionally substituted with 1, 2, or 3 substitutents independently selected from OH, —O—($C_{1-4}$ alkyl) and —O—$C_{1-4}$ haloalkyl. In further embodiments, one of $R^{3a}$ and $R^{3b}$ is $C_{1-6}$ alkyl.

In some embodiments, at least one of $R^{3a}$ and $R^{3b}$ is -$L^A$-$Cy^1$, wherein $L^A$ is $C_{1-3}$ alkylene optionally substituted with 1 or 2 substituents independently selected from halo, $OR^a$, and $SR^a$. In some embodiments, one of $R^{3a}$ and $R^{3b}$ is -$L^A$-$Cy^1$, wherein $L^A$ is $C_{1-3}$ alkylene optionally substituted with 1 or 2 substitutents independently selected from halo, $OR^a$, and $SR^a$. In some further embodiments, $Cy^1$ is aryl or heteroaryl, each optionally substituted by 1, 2, or 3 substituents independently selected from $Cy^3$, halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$. In yet further embodiments, $Cy^1$ is 1,2,4-oxadiazolyl optionally substituted by 1, 2, or 3 substituents independently selected from $Cy^3$, halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$.

In some embodiments:

at least one of $R^{3a}$ and $R^{3b}$ is selected from $C_{1-3}$ alkyl, wherein said $C_{1-3}$ alkyl is substituted with $Cy^1$ and optionally substituted with 1 or 2 substitutents independently selected from halo, $OR^a$, and $SR^a$;

$Cy^1$ is selected from aryl, heteroaryl, cycloalkyl, and heterocycloalkyl, each substituted with 1 or 2 $R^7$ and optionally substituted by 1, 2, or 3 $R^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:

one of $R^{3a}$ and $R^{3b}$ is selected from $C_{1-3}$ alkyl, wherein said $C_{1-3}$ alkyl is substituted with $Cy^1$ and optionally substituted with 1 or 2 substitutents independently selected from halo, $OR^a$, and $SR^a$;

$Cy^1$ is selected from aryl, heteroaryl, cycloalkyl, and heterocycloalkyl, each substituted with 1 or 2 $R^7$ and optionally substituted by 1, 2, or 3 $R^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:

at least one of $R^{3a}$ and $R^{3b}$ is selected from $C_{1-3}$ alkyl, wherein said $C_{1-3}$ alkyl is substituted with $Cy^1$ and optionally substituted with 1 or 2 substitutents independently selected from halo, $OR^a$, and $SR^a$;

$Cy^1$ is selected from aryl and heteroaryl each substituted with $R^7$ and optionally substituted by 1, 2, or 3 $R^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:

one of $R^{3a}$ and $R^{3b}$ is selected from $C_{1-3}$ alkyl, wherein said $C_{1-3}$ alkyl is substituted with $Cy^1$ and optionally substituted with 1 or 2 substitutents independently selected from halo, $OR^a$, and $SR^a$;

$Cy^1$ is selected from aryl and heteroaryl each substituted with $R^7$ and optionally substituted by 1, 2, or 3 $R^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, one of $R^{3a}$ and $R^{3b}$ is selected from $C_{1-3}$ alkyl substituted with 1,2,4-oxadiazolyl, wherein said 1,2,4-oxadiazolyl is substituted with a substituent selected from $Cy^3$ and -$L^B$-$Cy^3$. In some embodiments, one of $R^{3a}$ and $R^{3b}$ is selected from $C_{1-3}$ alkyl substituted with 1,2,4-oxadiazolyl, wherein said 1,2,4-oxadiazolyl is substituted with -$L^B$-$Cy^3$. In some further embodiments, $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, one of $R^{3a}$ and $R^{3b}$ is selected from $C_{1-3}$ alkyl substituted with 1,2,4-oxadiazolyl, wherein said 1,2,4-oxadiazolyl is substituted with -$Cy^3$. In some further embodiments, $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:

at least one of $R^{3a}$ and $R^{3b}$ is selected from $C_{1-3}$ alkyl, wherein said $C_{1-3}$ alkyl is substituted with —O-$Cy^2$ and optionally substituted with 1 or 2 substitutents independently selected from halo, $OR^a$, and $SR^a$;

$Cy^2$ is selected from aryl, heteroaryl, cycloalkyl, and heterocycloalkyl, each substituted with 1 or 2 $R^7$ and optionally substituted by 1, 2, or 3 $R^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:

one of $R^{3a}$ and $R^{3b}$ is selected from $C_{1-3}$ alkyl, wherein said $C_{1-3}$ alkyl is substituted with —O-$Cy^2$ and optionally substituted with 1 or 2 substituents independently selected from halo, $OR^a$, and $SR^a$;

$Cy^2$ is selected from aryl, heteroaryl, cycloalkyl, and heterocycloalkyl, each substituted with 1 or 2 $R^7$ and optionally substituted by 1, 2, or 3 $R^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:

at least one of $R^{3a}$ and $R^{3b}$ is selected from $C_{1-3}$ alkyl, wherein said $C_{1-3}$ alkyl is substituted with —O-$Cy^2$ and optionally substituted with 1 or 2 substituents independently selected from halo, $OR^a$, and $SR^a$;

$Cy^2$ is selected from aryl and heteroaryl, each substituted with $Cy^3$ and optionally substituted by 1, 2, or 3 $R^8$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:

one of $R^{3a}$ and $R^{3b}$ is selected from $C_{1-3}$ alkyl, wherein said $C_{1-3}$ alkyl is substituted with —O-$Cy^2$ and optionally substituted with 1 or 2 substituents independently selected from halo, $OR^a$, and $SR^a$;

$Cy^2$ is selected from aryl and heteroaryl, each substituted with $Cy^3$ and optionally substituted by 1, 2, or 3 $R^8$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, L is —($C_{1-18}$ alkylene)- optionally substituted by 1, 2, 3, 4, or 5 $R^{L1}$ In some embodiments, L is —($C_{1-18}$ alkylene)-.

In some embodiments, m and q are both 0.

In some embodiments, m is 0.

In some embodiments, q is 0.

In some embodiments, m is 1.

In some embodiments, q is 1.

In some embodiments, p is 1.

In some embodiments, r is 1.

In some embodiments, p is 0.

In some embodiments, r is 0.

In some embodiments, $R^1$ is H, $C_{1-10}$ alkyl, or Cy, wherein said $C_{1-10}$ alkyl is optionally substituted with 1, 2, 3, 4, or 5 $R^{L2}$.

In some embodiments, $R^1$ is H, $C_{1-10}$ alkyl optionally substituted with 1, 2, 3, 4, or 5 $R^{L2}$.

In some embodiments, $R^1$ is H or $C_{1-10}$ alkyl.

In some embodiments, $R^1$ is Cy.

In some embodiments, -L-$R^1$ is $C_{1-10}$ alkyl.

In some embodiments, -L-$R^1$ is $C_{1-7}$ alkyl optionally substituted with 1, 2, 3, 4 or 5 substitutents each independent selected from halo, cycloalkyl, OH, and CN. In some further embodiments, -L-$R^1$ is $C_{2-7}$ alkyl optionally substituted with 1, 2, 3, 4 or 5 halo.

In some embodiments, -L-$R^1$ is $C_{2-7}$ alkyl optionally substituted with 1, 2, 3, 4 or 5 substitutents each independent selected from halo, cycloalkyl, OH, and CN. In some further embodiments, -L-$R^1$ is $C_{2-7}$ alkyl optionally substituted with 1, 2, 3, 4 or 5 halo.

In some embodiments, -L-$R^1$ is $C_{2-7}$ alkyl. In some embodiments, -L-$R^1$ is $C_{3-6}$ alkyl. In some embodiments, -L-$R^1$ is $C_{3-5}$ alkyl. In some embodiments, -L-$R^1$ is propyl, butyl or pentyl.

In some embodiments, -L-$R^1$ is $C_{4-6}$ alkyl optionally substituted with 1, 2, 3, 4 or 5 substitutents each independent selected from halo, cycloalkyl, OH, and CN.

In some embodiments, -L-$R^1$ is butyl or pentyl.

In some embodiments, $R^2$ is halo, cyano, $C_1$ haloalkyl, or acetylenyl.

In some embodiments, $R^2$ is halo, cyano, or $C_1$ haloalkyl.

In some embodiments, $R^2$ is halo or $C_1$ haloalkyl.

In some embodiments, $R^2$ is Br or $CF_3$.

In some embodiments, $R^2$ is halo. In some further embodiments, $R^2$ is Cl or Br.

In some embodiments, $R^2$ is $C_1$ haloalkyl.

In some embodiments, $R^2$ is Br.

In some embodiments, $R^2$ is Cl.

In some embodiments, $R^2$ is $CF_3$.

In some embodiments, $R^{4a}$, $R^{4b}$, $R^{5a}$, and $R^{5b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, and $C_{1-6}$ cyanoalkyl.

In some embodiments, $R^{L1}$ and $R^{L2}$ are independently selected from halo, $C_{1-6}$ alkyl $C_{2-6}$ alkenyl, $C_{2-6}$ alkynyl, $C_{1-6}$ haloalkyl, CN, $NO_2$, and $OR^{a2}$.

In some embodiments, Cy is aryl optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, Cy is aryl.

In some embodiments, Cy is heteroaryl optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, Cy is heteroaryl.

In some embodiments, Cy is cycloalkyl optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, Cy is cycloalkyl.

In some embodiments, Cy is heterocycloalkyl optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, Cy is heterocycloalkyl.

In some embodiments, $Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $-(L^B)_{r1}-Cy^3$, $OR^{a4}$, $SR^{a4}$, $C(O)R^{b4}$, $C(O)NR^{c4}R^{d4}$ and $C(O)OR^{a4}$. In some embodiments, $Cy^1$ and $Cy^2$ are independently selected from aryl and heteroaryl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $-(L^B)_{r1}-Cy^3$, $OR^{a4}$, $SR^{a4}$, $C(O)R^{b4}$, $C(O)NR^{c4}R^{d4}$, and $C(O)OR^{a4}$.

In some embodiments, $Cy^1$ and $Cy^2$ are independently selected from aryl and heteroaryl, each substituted with $R^7$ and optionally substituted by 1, 2, or 3 $R^8$;

$R^7$ is selected from $Cy^3$ and $-L^B-Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiment, $L^B$ is $C_{1-4}$ alkylene optionally substituted with 1, 2, or 3 substituents independently selected from halo, OH, —O—($C_{1-4}$ alkyl), and —O—($C_{1-4}$ haloalkyl). In some further embodiment, $L^B$ is $C_{1-3}$ alkylene optionally substituted with 1 or 2 substituents independently selected from halo, OH, —O—($C_{1-4}$ alkyl), and —O—($C_{1-4}$ haloalkyl). In yet further embodiment, $L^B$ is $C_{1-3}$ alkylene optionally substituted with OH. In further embodiment, $L^B$ is $C_{1-3}$ alkylene.

In some embodiment, $L^B$ is $C_{1-4}$ alkylene optionally substituted with 1, 2, or 3 substituents independently selected from halo and OH. In some embodiment, $L^B$ is $C_{1-4}$ alkylene optionally substituted with 1 or 2 substituents independently selected from halo and OH. In some embodiment, $L^B$ is $C_{1-4}$ alkylene optionally substituted with 1 or 2 halo.

In some embodiments, the compounds of the invention have Formula IIa or IIb:

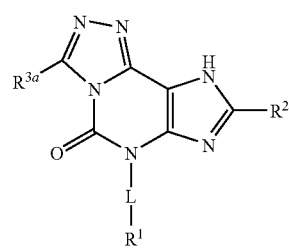

In some embodiments, the compounds of the invention have Formula IIa or IIb wherein:

L is $C_{1-18}$ alkylene;

$R^{3a}$ is H, halo, $C_{1-6}$ alkyl, $C_{2-6}$ alkenyl, $C_{2-6}$ alkynyl, or $C_{1-6}$ haloalkyl; and $R^2$ is halo or $C_1$ haloalkyl.

In some embodiments, the compounds of the invention have Formula IIa1 or IIb1:

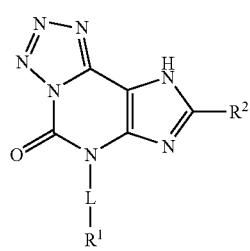

wherein $R^{3a}$, L, $R^1$ and $R^2$ are defined as the same as hereinabove.

In some embodiments, the compounds of the invention have Formula IIb1.

In some embodiments, the compounds of the invention have Formula IIb1, wherein -L-$R^1$ is $C_{1-7}$ alkyl optionally substituted with 1, 2, 3, 4 or 5 substitutents each independent selected from halo, cycloalkyl, OH, and CN. In some further embodiments, -L-$R^1$ is $C_{2-7}$ alkyl optionally substituted with 1, 2, 3, 4 or 5 halo. In yet further embodiments, -L-$R^1$ is $C_{2-6}$ alkyl or $C_{3-5}$ alkyl. In still further embodiments, -L-$R^1$ is propyl, butyl or pentyl. In further embodiments, -L-$R^1$ is butyl or pentyl.

In some embodiments, the compounds of the invention have Formula IIb1, wherein $R^2$ is halo or $C_1$ haloalkyl. In some further embodiments, $R^2$ is halo. In further embodiments, $R^2$ is Cl or Br. In some further embodiments, $R^2$ is Cl. In some embodiments, $R^2$ is Br.

In some embodiments, the compounds of the invention have Formula IIa1.

In some embodiments, the compounds of the invention have Formula IIa1, wherein:

-L-$R^1$ is $C_{1-7}$ alkyl optionally substituted with 1, 2, 3, 4 or 5 substitutents each independent selected from halo, cycloalkyl, OH, and CN;

$R^2$ is halo or $C_1$ haloalkyl; and $R^{3a}$ is selected from H, $C_{1-6}$ alkyl, $C_{1-6}$ haloalkyl, $Cy^1$, $OR^a$, $SR^a$, $S(O)R^b$, $S(O)_2R^b$, and $NR^cR^d$, wherein said $C_{1-6}$ alkyl is optionally substituted with 1, 2, or 3 substitutents independently selected from $Cy^1$, $C(O)NR^cR^d$, $C(O)OR^a$, halo, $OR^a$, $NR^cR^d$, $NR^cC(O)NR^cR^d$, and $NR^cC(O)R^b$.

In some embodiments, the compounds of the invention have Formula IIa, wherein -L-$R^1$ is $C_{2-7}$ alkyl optionally substituted with 1, 2, 3, 4 or 5 substitutents each independent selected from halo, cycloalkyl, OH, and CN. In some further embodiments, -L-$R^1$ is $C_{2-7}$ alkyl optionally substituted with 1, 2, 3, 4 or 5 halo. In yet further embodiments, -L-R$^1$ is C$_{2-6}$ alkyl or C$_{3-5}$ alkyl. In still further embodiments, -L-R$^1$ is propyl, butyl or pentyl.

In some embodiments, the compounds of the invention have Formula IIa, wherein R$^{3a}$ is selected from H, C$_{1-3}$ alkyl or C$_{1-3}$ haloalkyl. In some further embodiments, R$^{3a}$ is selected from H and methyl. In yet further embodiments, R$^{3a}$ is methyl.

In some embodiments, the compounds of the invention have Formula IIa, wherein:

R$^{3a}$ is C$_{1-3}$ alkyl substituted with Cy$^1$ and optionally substituted with 1 or 2 substitutents independently selected from halo, OR$^a$, and SR$^a$;

Cy$^1$ is selected from aryl and heteroaryl each substituted with R$^7$ and optionally substituted by 1, 2, or 3 R$^8$;

R$^7$ is, at each occurrence, independently selected from Cy$^3$ and -L$^B$-Cy$^3$;

R$^8$ is, at each occurrence, independently selected from halo, C$_{1-4}$ alkyl, C$_{2-4}$ alkenyl, C$_{2-4}$ alkynyl, C$_{1-4}$ haloalkyl, CN, NO$_2$, OR$^{a4}$, SR$^{a4}$, C(O)R$^{b4}$, C(O)NR$^{c4}$R$^{d4}$, and C(O)OR$^{a4}$; and Cy$^3$ is selected from aryl and heteroaryl, each optionally substituted with 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, aryl, heteroaryl, CN, NO$_2$, NR$^{c6}$R$^{d6}$, OR$^{a6}$, and SR$^{a6}$.

In some embodiments, the compounds of the invention have Formula IIa, wherein R$^{3a}$ is selected from C$_{1-3}$ alkyl substituted with 1,2,4-oxadiazolyl, wherein said 1,2,4-oxadiazolyl is substituted with a substituent selected from -Cy$^3$ and -L$^B$-Cy$^3$. In some further embodiments, Cy$^3$ is selected from aryl and heteroaryl, each optionally substituted with 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, aryl, heteroaryl, CN, NO$_2$, NR$^{c6}$R$^{d6}$, OR$^{a6}$, and SR$^{a6}$. In some embodiment, L$^B$ is C$_{1-4}$ alkylene optionally substituted with 1, 2, or 3 substituents independently selected from OH, —O—(C$_{1-4}$ alkyl), and —O—(C$_{1-4}$ haloalkyl).

In some embodiments, the compounds of the invention have Formula IIa, wherein:

R$^{3a}$ is C$_{1-3}$ alkyl, wherein said C$_{1-3}$ alkyl is substituted with —O-Cy$^2$ and optionally substituted with 1 or 2 substitutents independently selected from halo, OR$^a$, and SR$^a$;

Cy$^2$ is selected from aryl and heteroaryl, each substituted with Cy$^3$ and optionally substituted by 1, 2, or 3 R$^8$;

R$^8$ is, at each occurrence, independently selected from halo, C$_{1-4}$ alkyl, C$_{2-4}$ alkenyl, C$_{2-4}$ alkynyl, C$_{1-4}$ haloalkyl, CN, NO$_2$, OR$^{a4}$, SR$^{a4}$, C(O)R$^{b4}$, C(O)NR$^{c4}$R$^{d4}$, and C(O)OR$^{a4}$; and Cy$^3$ is selected from aryl and heteroaryl, each optionally substituted with 1, 2, 3, 4 or 5 substituents independently selected from halo, C$_{1-4}$ alkyl, C$_{2-4}$ alkenyl, C$_{2-4}$ alkynyl, C$_{1-4}$ haloalkyl, aryl, heteroaryl, CN, NO$_2$, NR$^{c6}$R$^{d6}$, OR$^{a6}$, and SR$^{a6}$.

In some embodiments, the compounds of the invention have Formula IIa, wherein -L-R$^1$ is C$_{2-6}$ alkyl optionally substituted with 1, 2, 3, 4 or 5 halo; R$^2$ is halo; and R$^{3a}$ is selected from H, C$_{1-3}$ alkyl and C$_{1-3}$ haloalkyl. In some further embodiments, R$^2$ is Cl or Br; and R$^{3a}$ is methyl.

In some embodiments, the compounds of the invention have Formula III:

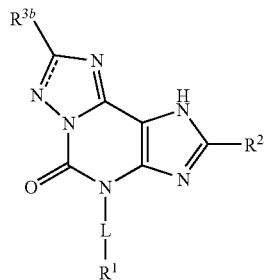

wherein R$^{3b}$, L, R$^1$ and R$^2$ are defined as the same as hereinabove.

In some embodiments, the compounds of the invention have Formula IIIa:

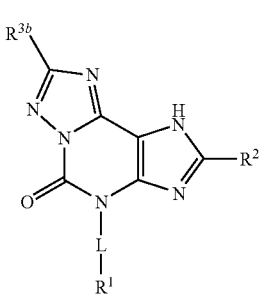

wherein R$^{3b}$, L, R$^1$ and R$^2$ are defined as the same as hereinabove.

In some embodiments, the compounds of the invention have Formula IIIa, wherein -L-R$^1$ is C$_{1-7}$ alkyl optionally substituted with 1, 2, 3, 4 or 5 substitutents each independent selected from halo, cycloalkyl, OH, and CN;

R$^2$ is halo or C$_1$ haloalkyl; and

R$^{3b}$ is selected from H, C$_{1-6}$ alkyl, C$_{1-6}$ haloalkyl, Cy$^1$, OR$^a$, SR$^a$, S(O)R$^b$, S(O)$_2$R$^b$, and NR$^c$R$^d$, wherein said C$_{1-6}$ alkyl is optionally substituted with 1, 2, or 3 substituents independently selected from Cy$^1$, C(O)NR$^c$R$^d$, C(O)OR$^a$, halo, OR$^a$, NR$^c$R$^d$, NR$^c$C(O)NR$^c$R$^d$, and NR$^c$C(O)R$^b$.

In some embodiments, the compounds of the invention have Formula IIIa, wherein -L-R$^1$ is C$_{2-7}$ alkyl optionally substituted with 1, 2, 3, 4 or 5 substitutents each independent selected from halo, cycloalkyl, OH, and CN. In some further embodiments, -L-R$^1$ is C$_{2-7}$ alkyl optionally substituted with 1, 2, 3, 4 or 5 halo. In yet further embodiments, -L-R$^1$ is C$_{2-6}$ alkyl or C$_{3-5}$ alkyl. In further embodiments, -L-R$^1$ is propyl, butyl or pentyl.

In some embodiments, the compounds of the invention have Formula IIIa, wherein R$^{3b}$ is selected from H, C$_{1-3}$ alkyl or C$_{1-3}$ haloalkyl. In some further embodiments, R$^{3b}$ is selected from H and methyl. In yet further embodiments, R$^{3b}$ is methyl.

In some embodiments, the compounds of the invention have Formula IIIa, wherein:

R$^{3b}$ is C$_{1-3}$ alkyl substituted with Cy$^1$ and optionally substituted with 1 or 2 substitutents independently selected from halo, OR$^a$, and SR$^a$;

Cy$^1$ is selected from aryl, heteroaryl, cycloalkyl, and heterocycloalkyl, each substituted with 1 or 2 R$^7$ and optionally substituted by 1, 2, or 3 R$^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, the compounds of the invention have Formula IIIa, wherein:

$R^{3b}$ is $C_{1-3}$ alkyl substituted with $Cy^1$ and optionally substituted with 1 or 2 substitutents independently selected from halo, $OR^a$, and $SR^a$;

$Cy^1$ is selected from aryl and heteroaryl each substituted with $R^7$ and optionally substituted by 1, 2, or 3 $R^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, the compounds of the invention have Formula IIIa, wherein $R^{3b}$ is selected from $C_{1-3}$ alkyl substituted with 1,2,4-oxadiazolyl, wherein said 1,2,4-oxadiazolyl is substituted with a substituent selected from -$Cy^3$ and -$L^B$-$Cy^3$. In some further embodiments, $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$. In some embodiment, $L^B$ is $C_{1-4}$ alkylene optionally substituted with 1, 2, or 3 substituents independently selected from OH, —O—($C_{1-4}$ alkyl), and —O—($C_{1-4}$ haloalkyl).

In some embodiments, the compounds of the invention have Formula IIIa, wherein:

$R^{3b}$ is selected from $C_{1-3}$ alkyl, wherein said $C_{1-3}$ alkyl is substituted with —O-$Cy^2$ and optionally substituted with 1 or 2 substitutents independently selected from halo, $OR^a$, and $SR^a$;

$Cy^2$ is selected from aryl and heteroaryl, each substituted with $Cy^3$ and optionally substituted by 1, 2, or 3 $R^8$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, the compounds of the invention have Formula IIIa, wherein $R^2$ is halo. In some further embodiments, $R^2$ is Cl. In other embodiments, $R^2$ is Br.

In some embodiments, the compounds of the invention have Formula IIIa, wherein -L-$R^1$ is $C_{2-6}$ alkyl optionally substituted with 1, 2, 3, 4 or 5 halo; $R^2$ is halo; and $R^{3b}$ is selected from H, $C_{1-3}$ alkyl and $C_{1-3}$ haloalkyl. In some further embodiments, $R^2$ is Cl or Br; and $R^{3b}$ is methyl.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl (e.g., n-propyl or isopropyl), $C_4$ alkyl (e.g., n-butyl, isobutyl, t-butyl), or, $C_5$ alkyl (e.g., n-pentyl, isopentyl, or neopentyl), and $C_6$ alkyl.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group. One example of alkylene is —$CH_2CH_2$—.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Examples of haloalkyl group include $CH_2F$, $CHF_2$, $CF_3$, $C_2F_5$, $CCl_3$, $CHCl_2$, $CH_2CF_3$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles. A heterocycloalkyl group having one or more fused aromatic rings can be attached though either the aromatic or non-aromatic portion. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "arylalkyl" refers to alkyl substituted by aryl and "cycloalkylalkyl" refers to alkyl substituted by cycloalkyl. One example of arylalkyl is benzyl. One example of cycloalkylalkyl is —$CH_2CH_2$-cyclopropyl.

As used herein, "heteroarylalkyl" refers to an alkyl group substituted by a heteroaryl group, and "heterocycloalkylalkyl" refers to alkyl substituted by heterocycloalkyl. One example of heteroarylalkyl is —$CH_2$-(Pyridin-4-yl). One example of heterocycloalkylalkyl is —$CH_2$-(piperidin-3-yl).

As used herein, "halo" or "halogen" includes fluoro, chloro, bromo, and iodo.

As used herein, "hydroxyalkyl" refers to an alkyl group substituted with a hydroxyl group.

As used herein, "cyanoalkyl" refers to an alkyl group substituted with a cyano group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted.

All compounds, and pharmaceutically acceptable salts thereof, are also meant to include solvated or hydrated forms.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques as described below.

Scheme 1 describes the synthesis of trifluoromethyl substituted triazolopurinone derivative 1j and tetrazolopurinone derivative 1k. Reaction of urea 1a with cyanoacetic acid 1b in the presence of an anhydride such as Ac$_2$O provides the pyrimidinedione intermediate 1c. Nitrosation of compound 1c using sodium nitrite under a suitable condition (such as in the presence of acetic acid and aqueous HCl), followed by reducing the resulting nitroso intermediate 1d using a reducing reagent such as Na$_2$S$_2$O$_4$, affords the diamino intermediate 1e. Cyclization of the diamino intermediate 1e can be accomplished by treatment with trifluoroacetic anhydride to yield the xanthine derivative 1f. Following conversion of the 4-carbonyl of xanthine 1f to thiocarbonyl using P$_2$S$_5$, selective methylation at the sulfur using methyl sulfate in aqueous NaOH solution gives rise to the thioether intermediate 1h. Reaction of the thioether intermediate 1h with hydrazine affords the resulting hydrazone 1i, which is subjected to treatment with an orthoester [such as R$^{3a}$C(O-alkyl)$_3$, e.g., R$^{3a}$C(OEt)$_3$] to yield the cyclized trizole 1j. Alternatively, intermediate 1i can be treated with NaNO$_2$ under a suitable condition (such as in the presence of an acid, e.g., aqueous HCl) to provides the cyclized tetrazolopurinone 1j.

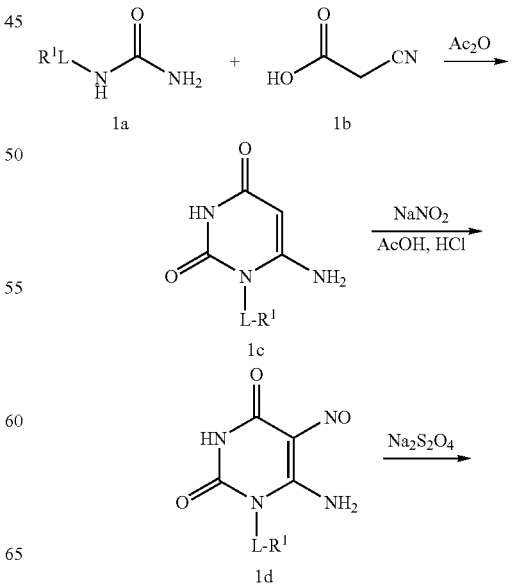

Scheme 1

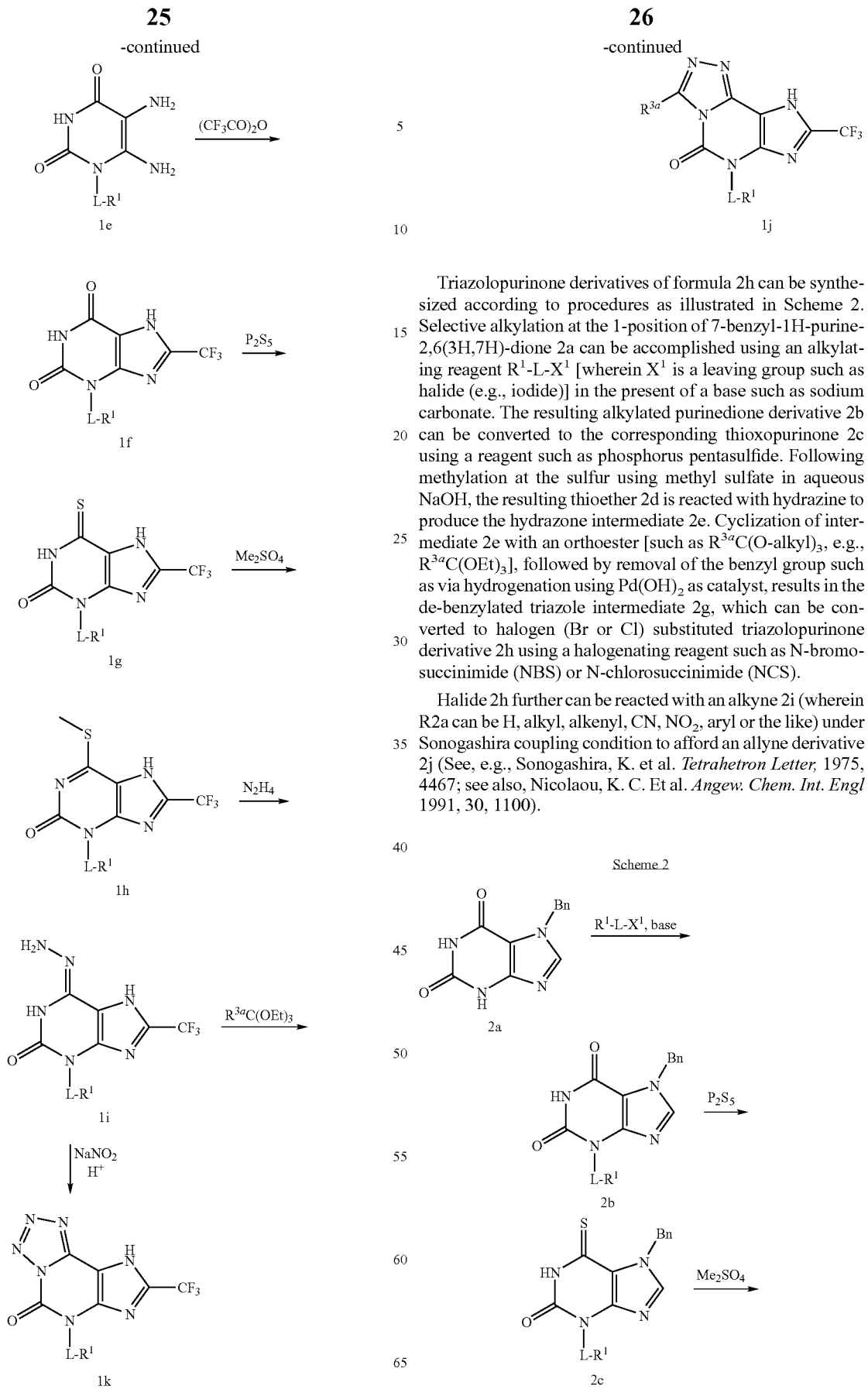

Triazolopurinone derivatives of formula 2h can be synthesized according to procedures as illustrated in Scheme 2. Selective alkylation at the 1-position of 7-benzyl-1H-purine-2,6(3H,7H)-dione 2a can be accomplished using an alkylating reagent $R^1$-L-$X^1$ [wherein $X^1$ is a leaving group such as halide (e.g., iodide)] in the present of a base such as sodium carbonate. The resulting alkylated purinedione derivative 2b can be converted to the corresponding thioxopurinone 2c using a reagent such as phosphorus pentasulfide. Following methylation at the sulfur using methyl sulfate in aqueous NaOH, the resulting thioether 2d is reacted with hydrazine to produce the hydrazone intermediate 2e. Cyclization of intermediate 2e with an orthoester [such as $R^{3a}$C(O-alkyl)$_3$, e.g., $R^{3a}$C(OEt)$_3$], followed by removal of the benzyl group such as via hydrogenation using Pd(OH)$_2$ as catalyst, results in the de-benzylated triazole intermediate 2g, which can be converted to halogen (Br or Cl) substituted triazolopurinone derivative 2h using a halogenating reagent such as N-bromosuccinimide (NBS) or N-chlorosuccinimide (NCS).

Halide 2h further can be reacted with an alkyne 2i (wherein R2a can be H, alkyl, alkenyl, CN, NO$_2$, aryl or the like) under Sonogashira coupling condition to afford an allyne derivative 2j (See, e.g., Sonogashira, K. et al. *Tetrahetron Letter*, 1975, 4467; see also, Nicolaou, K. C. Et al. *Angew. Chem. Int. Engl* 1991, 30, 1100).

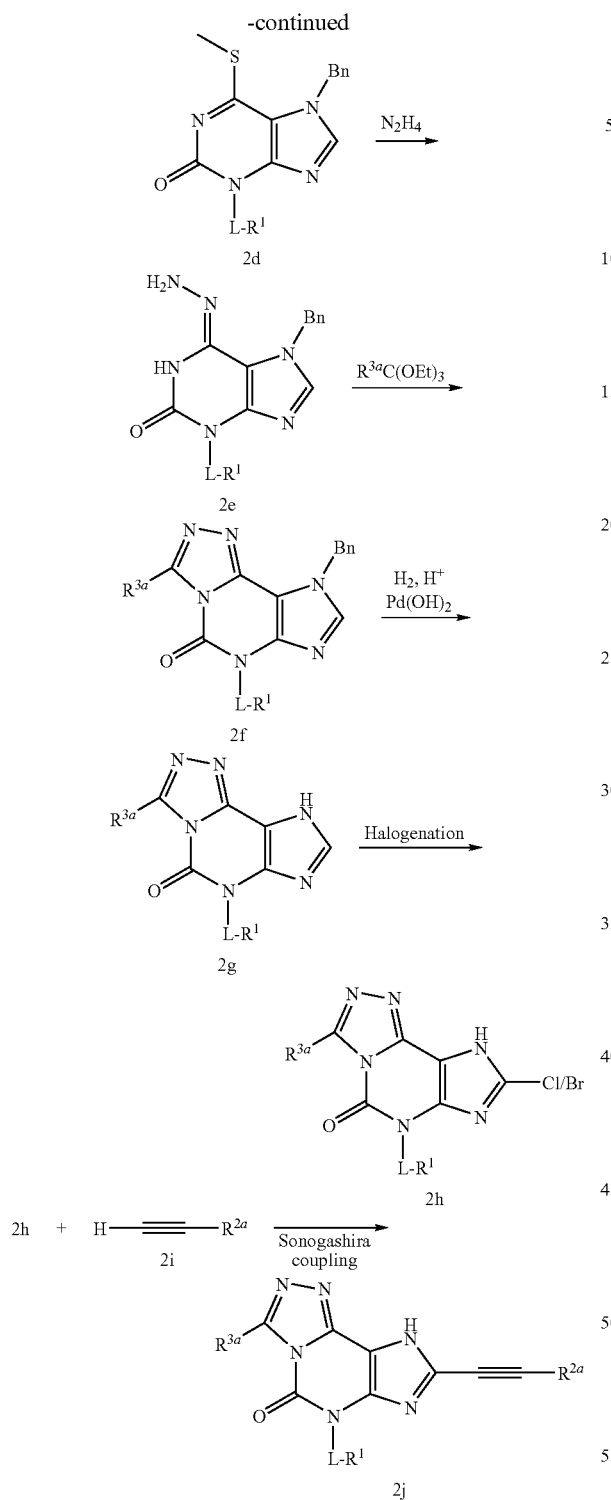

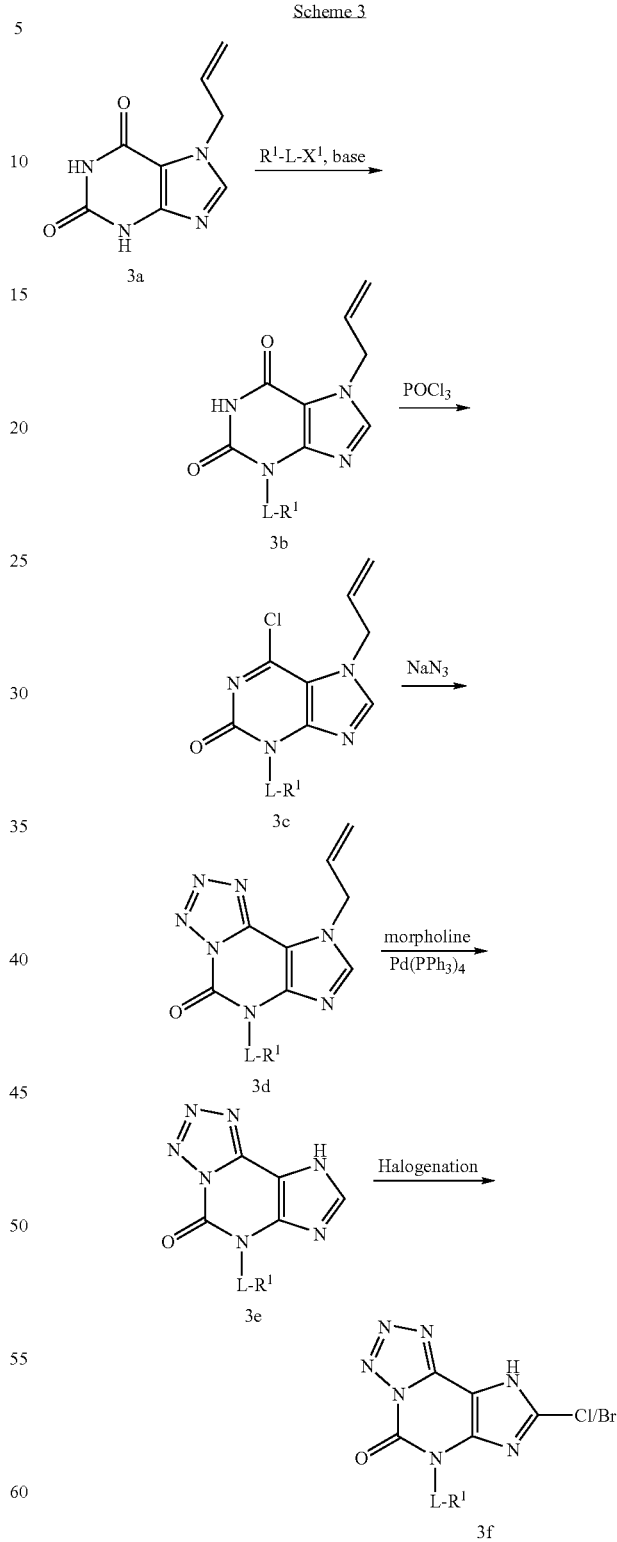

Pd(PPh$_3$)$_4$, halogenation of the resulting intermediate 3e using a halogenating reagent such as NBS or NCS can afford compound 3f.

Compounds of formula 3f can be prepared using procedures depicted in Scheme 3. 7-Allyl-1H-purine-2,6(3H,7H)-dione 3a can be region-selectively alkylated at the 3-position with an alkylation reagent R$^1$-L-X$^1$ such an alkyl halide (wherein the leaving group X$^1$ is halo) in the presence of a base such as sodium carbonate. The resulting intermediate 3b is subjected to treatment with phosphoryl chloride to provide intermediate 3c. Treatment of 3c with sodium azide can give rise to tetrazolopurinone intermediate 3d. Following removal of the allyl group such as using morpholine in the presence of Compounds of formula 4g can be prepared using procedures outlined in Scheme 4. Selective alkylation at the amino group of commercially available 4-amino-1H-imidazole-5-carbonitrile (4a) by reductive amination with an appropriate aldehyde provides the alkylated product 4b. Reaction of intermediate 4b with a hydrazide R³ᵇ—C(O)—NHNH₂ yields triazole derivative 4c. Alternatively, carbonitrile 4b can be reacted with sodium hydrogen sulfide to form carbothioamide 4d, which is subjected to methylation to afford carbimidothioate 4e. Reaction of carbimidothioate 4e with a hydrazide R³ᵇ—C(O)—NHNH₂ yields triazole derivative 4c. Cyclization of triazole derivative 4c with 1,1'-carbonyldiimidazole (CDI) yields triazolopurinone 4f. Selective halogenation of 4f using a suitable halogenating reagent (such as NBS or NCS) provides the halo-substituted triazolopurinone derivative 4g.

Compounds of formula 5b can be prepared using procedures described in Scheme 5. Cyclization of triazole derivative 4c (wherein R³ᶜ is R³ᵃ or R³ᵇ) with phosgene yields a mixture of triazolopurinones 5a and 4f which can be separated by conventional methods such as using column chromatography. Selective halogenation of 5a using a suitable halogenating reagent (such as NBS or NCS) provides the halo-substituted triazolopurinone derivatives of formula 5b.

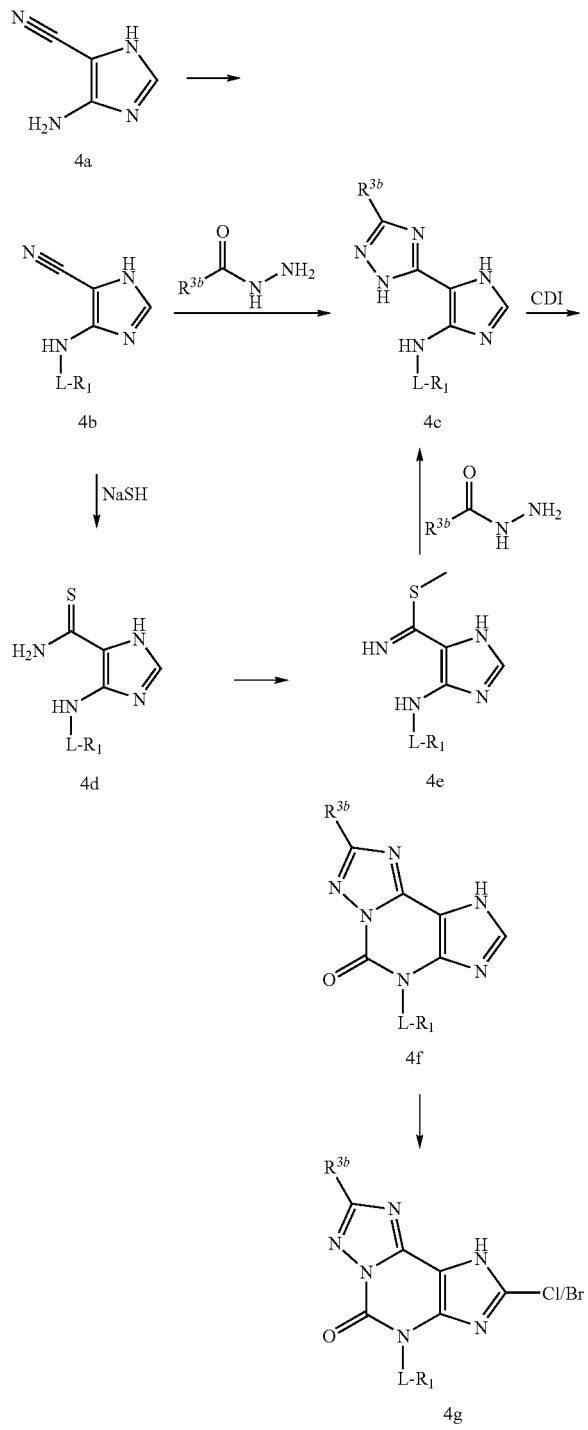

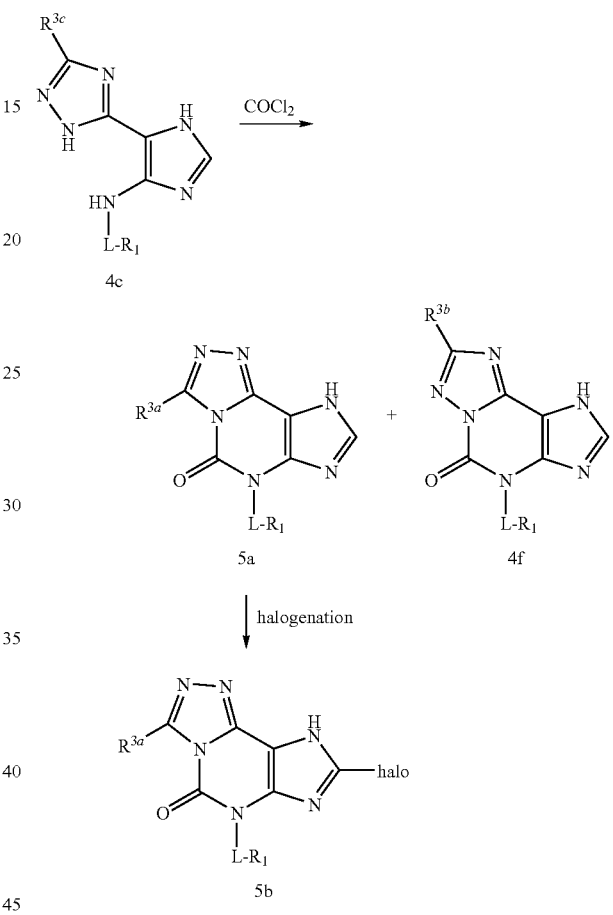

Compounds of formula 6g can be prepared using procedures shown in Scheme 6. Coupling of hydroxyimidamide 6a with acid 6b (wherein n can be 1, 2, or 3) in the presence of CDI (followed by cyclization and condensation) yields oxadiazol ester 6c. Saponification of 6c, followed by coupling with hydrazine under a suitable condition, provides hydrazide 6e. Reaction of hydrazide 6e with carbimidothioate 4e at an elevated temperature generates triazolopurinone 6f, which is halogenated using a suitable halogenating reagent (such as NBS or NCS) to provide the halo-substituted triazolopurinone 6g.

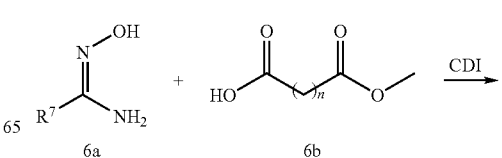

-continued

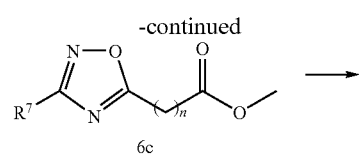
6c

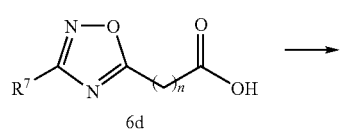
6d

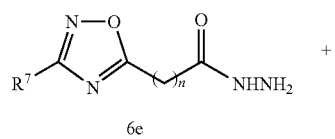 +
6e

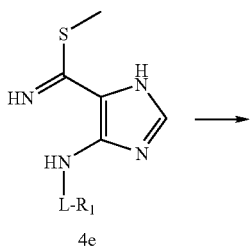
4e

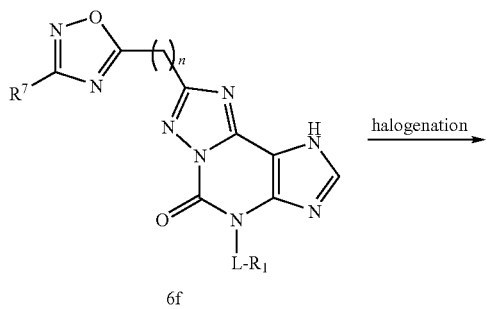
6f halogenation →

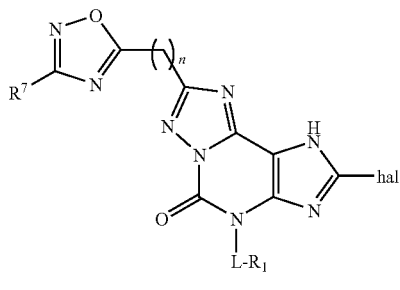
6g

Compounds of formula 7f can be prepared using procedures outlined in Scheme 7. Conversion of commercially available (4-bromophenoxy)acetic acid (7a) to hydrazide 7b using hydrazine, followed by condensation with carbimidothioate 4e, provides triazole intermediate 7c. Cyclization of triazole derivative 7c in the presence of CDI yields triazolopurinone 7d. Reaction of formula 7d with known boric acid B(OH)$_2$Cy$^3$ [wherein Cy$^3$ is an optionally substituted aryl or an optionally substituted heteroaryl group] under Suzuki coupling conditions can yield triazolopurinone derivatives of formula 7e. Selective halogenation of 7e using a suitable halogenating reagent (such as NBS or NCS) provides the halo-substituted triazolopurinone derivatives of formula 7f.

Scheme 7

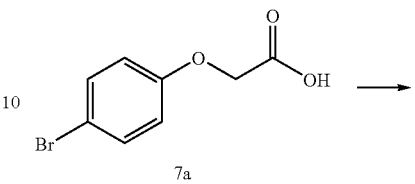
7a

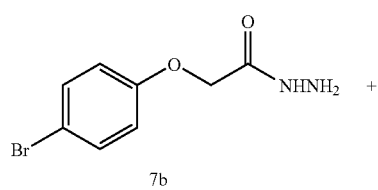
7b +

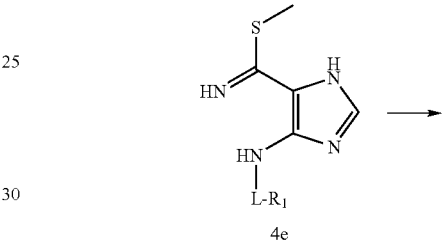
4e

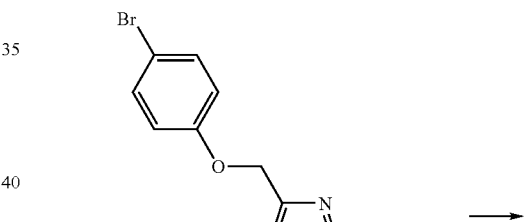
7c

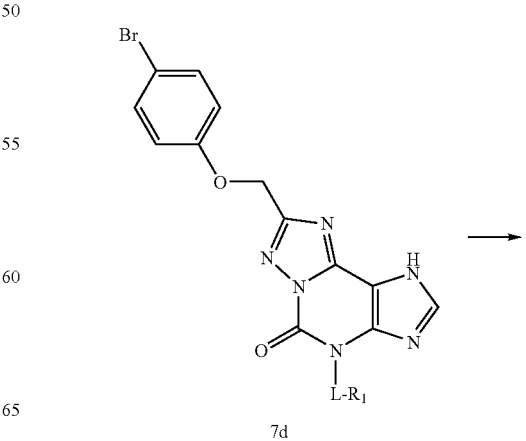
7d

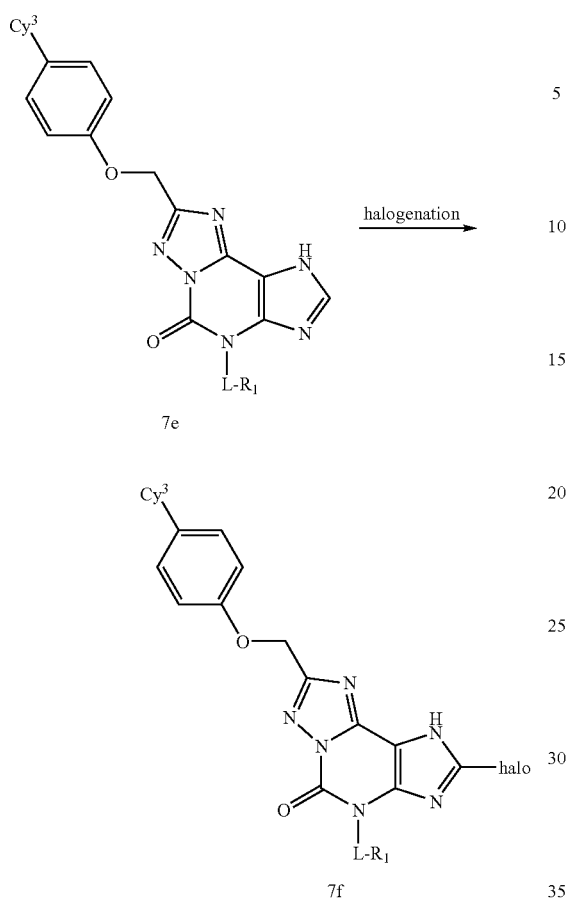

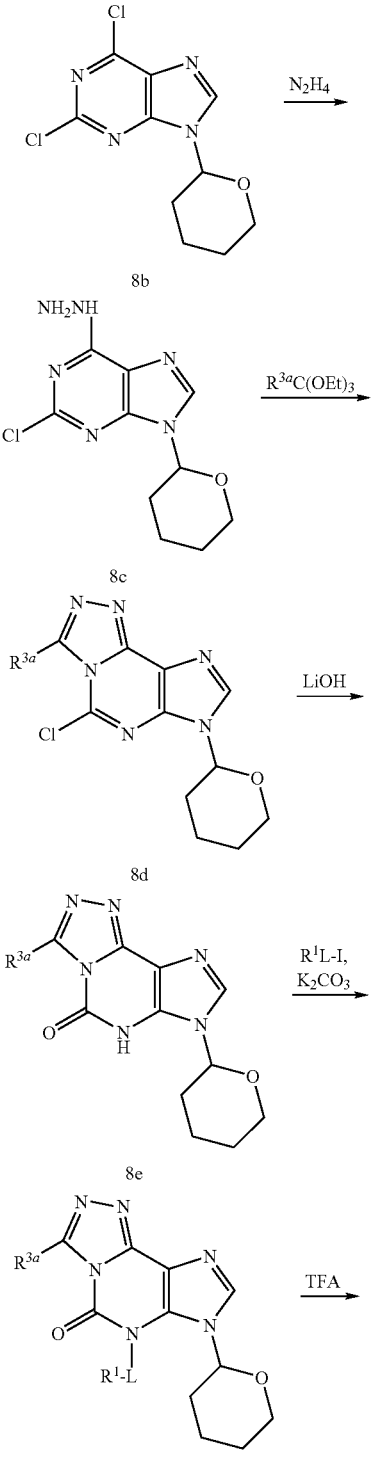

Compounds of formula 5b can also be prepared using procedures summarized in Scheme 8. Reaction of commercially available 2,6-dichloropurine (8a) with dihydropyran catalyzed by an acid provides protected 2,6-dichloropurine 8b. Addition of hydrazine to compound 8b gives hydrazinopurine 8c, which can be cyclized with an orthoester [such as $R^{3a}C(O\text{-alkyl})_3$, e.g., $R^{3a}C(OEt)_3$] to give triazolopurine 8d. Treatment of chloride 8d with a base such as LiOH yields triazolopurin-5-one 8e. Selective alkylation of compound 8e with alkylating reagent such as an alkyl iodide $R^1$-L-I, in the presence of a base such as $K_2CO_3$, gives alkylated triazolopurin-5-one 8f. Removal of the tetrahydropyranyl protecting group of compound 8f under acidic condition [such as in the presence of trifluoroacetic acid (TFA)], followed by selective halogenation of intermediate 8g, provides the halo-substituted triazolopurinone derivatives of formula 5b.

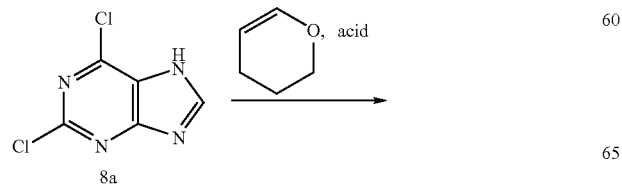

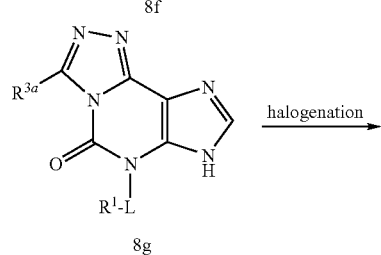

-continued

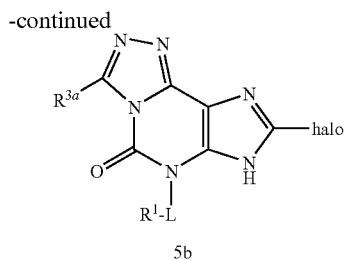

5b

Pharmaceutical Methods

Compounds of the invention can modulate activity of the HM74a receptor. The term "modulate" is meant to refer to an ability to increase or decrease activity of a receptor. Accordingly, compounds of the invention can be used in methods of modulating HM74a receptor by contacting the receptor with any one or more of the compounds or compositions described herein. In some embodiments, compounds of the present invention can act as full or partial agonists of HM74a receptors. In further embodiments, the compounds of the invention can be used to modulate activity of HM74a receptors in an individual by administering a modulating amount of a compound of the invention.

The present invention further provides methods of treating diseases associated with the HM74a receptor, such as dyslipidemia, insulin resistance, hyperglycemia, and others, in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to the HM74a receptor, such as diseases, disorders or conditions associated with low expression or low activity of HM74a receptor.

Examples of HM74a receptor-associated diseases include, but are not limited to, dyslipidemia, highly-active anti-retroviral therapy (HAART)-associated lipodystrophy, insulin resistance, diabetes such as type 2 diabetes mellitus, metabolic syndrome, atherosclerosis, coronary heart disease, stroke, obesity, elevated body mass index (BMI), elevated waist circumference, non-alcoholic fatty liver disease, hepatic steatosis, hypertension, and other pathologies, such as those (like many of the aforementioned) associated with elevated plasma FFAs.

Other diseases treatable by administration of compounds of the invention (and salts or prodrugs there) include chronic inflammatory diseases such as, for example, pancreatitis and gout.

As used herein, the term "dyslipidemia" refers to any one or more of the following diseases or conditions: low-HDL cholesterol, elevated cholesterol, elevated LDL cholesterol (including any combination of small, dense LDL, intermediate density lipoproteins, very-low density lipoproteins, and chylomicrons), elevated total cholesterol/HDL ratio, elevated plasma triglycerides, elevated circulating free fatty acid levels, and elevated lipoprotein (a).

In some embodiments, the present invention provides methods of lowering cholesterol level, lowering LDL, lowering total cholesterol/HDL ratio, lowering plasma triglycerides, lowering circulating free fatty acid levels, lowering lipoprotein (a), or raising HDL cholesterol, in a mammal by administering an effective amount of a compound or composition herein to the mammal.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell comprising the eye.

As used herein, the term "contacting" refers to the bringing together of indicated moieties in an in vitro system or an in vivo system. For example, "contacting" the HM74a receptor with a compound of the invention includes the administration of a compound of the present invention to an individual or patient, such as a human, having the HM74a receptor, as well as, for example, introducing a compound of the invention into a sample containing a cellular or purified preparation containing the HM74a receptor.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing or retarding the pathology and/or symptomatology) such as decreasing the severity of disease.

Combination Therapies

The compounds of the present invention can be used in combination with other enzyme or receptor modulators. Examples of other enzyme or receptor modulators include, but are not limited to, any one or more of the following: steroidal and non-steroidal anti-inflammatory agents (e.g., inhibitors or prostaglandin synthesis), inhibitors of PCSK9, inhibitors of ACC1, inhibitors of ACC2, inhibitors of SCD1, inhibitors of DGAT, activators of AMPK, thyroid receptor modulators, renin inhibitors, agents that degrade or inhibit formation of advanced glycation end products, HMG-CoA reductase inhibitors (so-called statins), PPAR alpha agonists or selective modulators, PPAR gamma agonists or selective modulators (both TZD and non-TZD), PPAR delta agonists or selective modulators, PPAR alpha/gamma dual agonists, pan-PPAR agonists or selective modulators, glucocorticoid receptor antagonists or selective modulators, bile acid-binding resins, NPC1L1 receptor antagonists, cholesterol ester transfer protein inhibitors, apoA-I or synthetic apoA-I/HDL molecules, LXR agonists or selective modulators, FXR agonists or selective modulators, endothelial lipase inhibitors, hepatic lipase inhibitors, SR-BI modulators, estrogen receptor agonists or selective modulators, anabolic steroid or steroid derivatives, insulin or insulin mimetics, sulfonylureas, metformin or other biguanides, DPP-IV inhibitors, PTP-1B modulators, glucose-6-phosphatase inhibitors, T1-translocase inhibitors, fructose-1,6-bisphosphatase inhibitors, glycogen phosphorylase inhibitors, glucagon receptor antagonists, 11-beta-hydroxysteroid dehydrogenase type 1 inhibitors, intestinal lipase inhibitors, neurotransmitter reuptake inhibitor, endocannabinoid receptor antagonist, NPY antagonist, MCH antagonists, MC4R agonists, GLP-1 or GLP-1 analogues (incretins), GLP-1 receptor agonists, thiazide diuretics, beta-adrenergic receptor antagonists, angiotensin II converting enzyme inhibitors, angiotensin II receptor antagonists, calcium channel antagonists, and mineralocorticoid receptor antagonists, or combinations thereof.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, antibodies, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating HM74a in tissue samples, including human, and for identifying HM74a ligands by binding of a labeled compound. Accordingly, the present invention includes HM74a assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radiolabeled compounds will depend on the specific application of that radio-labeled compound. For example, for in vitro labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to HM74a. Accordingly, the ability of a test compound to compete with the radio-labeled compound for binding to HM74a directly correlates to its binding affinity.

Kits

The present invention also includes pharmaceutical kits useful, for example, in the treatment or prevention of HM74a-associated diseases or disorders. The kits can include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

The compounds of the example section were found to be agonists or partial agonists of HM74a receptor according to one or more of the assays provided herein.

EXAMPLES

General Information

All reagents and solvents were obtained from commercial sources and were used directly without further purification. LCMS analysis was performed on a Water SunFire C18 column (2.1×50 mm, 5 µM particle size), eluting with 0.025% TFA/water and 0.025% TFA/acetonitrile using a mass spectrum scan range of 105-900 Da. Preparative LCMS purifications were performed on a Water FractionLynx system using mass directed fraction and compound-specific method optimization (J. Comb. Chem. 2004, 6, 874-883). The LC method utilized a Waters SunFire column (19×100 mm, 5 µM particle size), eluting with either 0.1% TFA/water and 0.1% TFA/acetonitrile gradient (method A) or a Waters×Bridge C18 column (19×100 mm, 5 µM particle size), eluting with 0.15% NH$_4$OH/water and 0.15% NH$_4$OH/acetonitrile gradient (method B) at a flow rate of 30 mL/min over a total run time of 5 min. NMR spectra were obtained using a Varian Mercury-300 or Mercury-400 spectrometer. Chemical shifts are reported in parts per million (ppm) relative to tetramethylsilane as an internal standard.

Example 1

Preparation of 6-pentyl-8-(trifluoromethyl)-6,9-dihydro-5H-[1,2,4]triazolo[3,4-i]purin-5-one

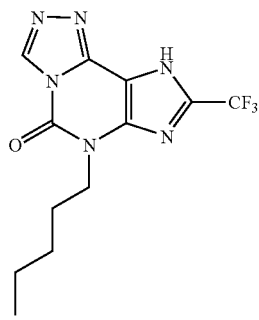

Step A: N-Pentylurea

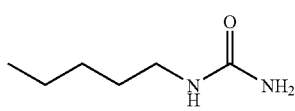

To a 7.0 M solution of ammonia in methanol (32 mL) was dropwise added 1-isocyanatopentane (5.0 g, 0.044 mol). After the addition, the mixture was stirred at room temperature for 1 h and concentrated under reduced pressure to give a white solid, which was directly used for next step without further purification. LCMS calculated for C$_6$H$_{15}$N$_2$O (M+H): 131.1. found 131.1.

Step B:
6-Amino-1-pentylpyrimidine-2,4(1H,3H)-dione

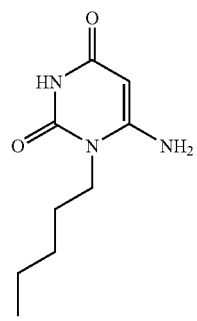

A mixture of N-pentylurea (5.8 g, 0.044 mol), acetic anhydride (20 mL, 0.2 mol) and cyanoacetic acid (4.21 g, 0.0495 mol) was stirred at 70° C. for 2 h. After cooling down to room temperature, the precipitate was collected by suction filtration, washed with EtOH and air dried to yield 6.0 g of solid. The solid was treated with a 3.0 M solution of sodium hydroxide in water (25 mL) at 70° C. for 2 h. After cooling down to room temperature, the pH of the reaction mixture was adjusted to neutral using 10 N HCl aqueous solution and the solid formed was collected by filtration to afford the desired product as a white solid (4.0 g, 46% yield). LCMS calculated for C$_9$H$_{16}$N$_3$O$_2$ (M+H): 198.1. found 198.0.

Step C: 6-Amino-5-nitroso-1-pentylpyrimidine-2,4 (1H,3H)-dione

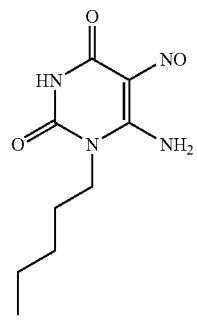

To a stirring mixture of 6-amino-1-pentylpyrimidine-2,4 (1H,3H)-dione (4.0 g, 0.020 mol) and acetic acid (20 mL, 0.4 mol) in water (20 mL) was slowly added sodium nitrite (1.5 g, 0.022 mol). Stirring was continued at room temperature for 2 h at which time the reaction mixture became pink and precipitate formed. The reaction mixture was concentrated under reduced pressure. The resulting residue was dissolved in aqueous NaOH solution and extracted with methylene chloride to remove byproducts. The aqueous solution was neutralized with HCl and concentrated. The residue was treated with methanol and filtered. The filtrate was concentrated to give the desired product as pink solid. LCMS calculated for C$_9$H$_{15}$N$_4$O$_3$ (M+H): 227.1. found: 227.1 (M+H), 249.1 (M+Na).

Step D: 5,6-Diamino-1-pentylpyrimidine-2,4(1H, 3H)-dione

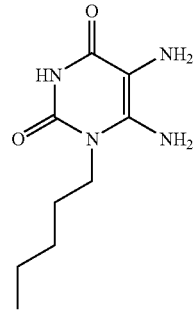

To a mixture of 6-amino-5-nitroso-1-pentylpyrimidine-2, 4(1H,3H)-dione (1.9 g, 8.3 mmol) and a solution of ammonia in water (20 M, 20 mL) at 70° C. was added sodium dithionite (3.1 g, 18 mmol) slowly. After stirring for 20 minutes, the reaction mixture was concentrated to a volume of about 10 mL and cooled in an ice bath. The greenish solid was collected by filtration and dried on high vacuum for 4 h to provide the desire product (1.5 g, 85% yield). LCMS calculated for $C_9H_{17}N_4O_2$(M+H): 213.1. found: 213.2.

Step E: 3-Pentyl-8-(trifluoromethyl)-3,7-dihydro-1H-purine-2,6-dione

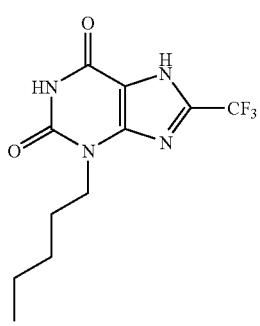

A mixture of 5,6-diamino-1-pentylpyrimidine-2,4(1H, 3H)-dione (1.5 g, 7.1 mmol) and trifluoroacetic anhydride (20 mL, 100 mmol) in DMF (20 mL) was heated at 70° C. for 1 h. After removing most of unreacted trifluoroacetic anhydide by evaporation under reduced pressure, the remaining solution was transferred to a sealed tube and heated at 120° C. for 1 h. After cooling to room temperature, the reaction mixture was concentrated under reduced pressure and the residue was triturated with methylene chloride to form solid precipitates. The solid was filtered to provide the desired product (0.81 g, 39.5% yield). LCMS calculated for $C_{11}H_{14}F_3N_4O_2$ (M+H): 291.107. found: 291.1.

Step F: 3-Pentyl-6-thioxo-8-(trifluoromethyl)-1,3,6, 7-tetrahydro-2H-purin-2-one

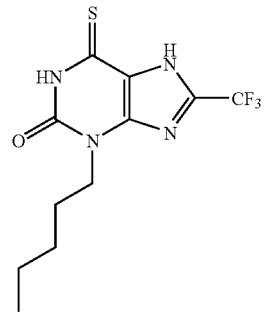

A mixture of 3-pentyl-8-(trifluoromethyl)-3,7-dihydro-1H-purine-2,6-dione (0.81 g, 2.8 mmol) and phosphorus pentasulfide (1.2 g, 2.8 mmol) in 1,4-dioxane (20 mL) was heated at 100° C. for 2 h. The reaction mixture was concentrated under reduced pressure. The residue was purified by silica gel chromatography twice (0-50% MeOH in $CH_2Cl_2$) to yield 0.15 g of pure product as a yellow solid (0.15 g, 18% yield). LCMS calculated for $C_{11}H_{14}F_3N_4OS$ (M+H): 307.1. found: 307.1.

Step G: 6-(Methylthio)-3-pentyl-8-(trifluoromethyl)-3,7-dihydro-2H-purin-2-one

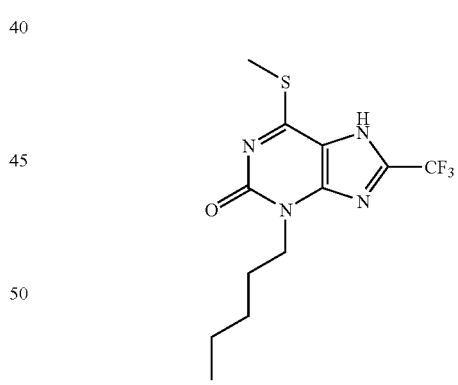

To a mixture of 3-pentyl-6-thioxo-8-(trifluoromethyl)-1,3, 6,7-tetrahydro-2H-purin-2-one (0.15 g, 0.49 mmol) in a solution of sodium hydroxide in water (2 M, 2 mL) was added dimethyl sulfate (0.056 mL, 0.59 mmol). The reaction mixture was heated at 80° C. for 1.5 h, quenched with acetic acid and extracted with methylene chloride. The organic layer was dried (MgSO$_4$), concentrate and purified by silica gel chromatography (0-20% EtOAc in hexane) to provide the product as a yellow solid (0.15 g, 95% yield). LCMS calculated for $C_{12}H_{16}F_3N_4OS$ (M+H): 321.1. found: 321.1.

Step H: (6E)-3-Pentyl-8-(trifluoromethyl)-3,7-dihydro-1H-purine-2,6-dione-6-hydrazone

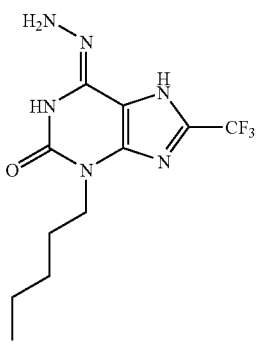

A mixture of 6-(methylthio)-3-pentyl-8-(trifluoromethyl)-3,7-dihydro-2H-purin-2-one (0.15 g, 0.23 mmol) and hydrazine (0.80 mL, 25 mmol) in water (0.80 mL) was heated at 100° C. for 1 h. The solution was concentrated under reduced pressure and azeotropically treated with toluene twice. The resulting residue was used for next step without purification. LCMS calculated for $C_{11}H_{16}F_3N_6O$ (M+H): 305.1. found: 305.1.

Step I: 6-Pentyl-8-(trifluoromethyl)-6,9-dihydro-5H-[1,2,4]triazolo[3,4-i]purin-5-one

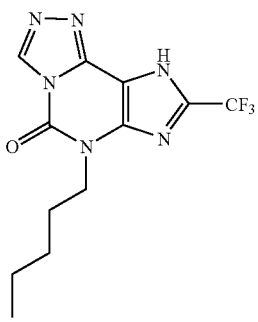

(6E)-3-Pentyl-8-(trifluoromethyl)-3,7-dihydro-1H-purine-2,6-dione-6-hydrazone (0.15 g, 0.20 mmol) was mixed with ethyl orthoformate (2 mL, 10 mmol). The mixture was heated at 100° C. for 30 min, concentrated under reduced pressure and purified by preparative HPLC to yield the desired product. LCMS calculated for $C_{12}H_{14}F_3N_6O$ (M+H): 315.1. found: 315.1.

Example 2

Preparation of 6-butyl-8-(trifluoromethyl)-6,9-dihydro-5H-[1,2,4]triazolo[3,4-i]purin-5-one

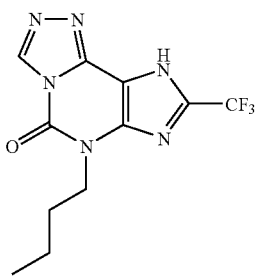

The title compound was prepared using procedures analogous to those described for Example 1. LCMS calculated for $C_{11}H_{12}F_3N_6O$: (M+H) 301.1. found 301.1.

Example 3

Preparation of 6-butyl-3-methyl-8-(trifluoromethyl)-6,9-dihydro-5H-[1,2,4]triazolo[3,4-i]purin-5-one

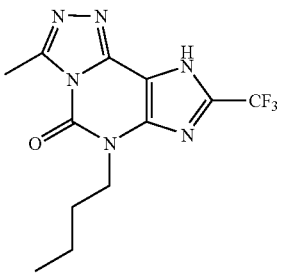

The title compound was prepared using procedures analogous to those described for Example 1. LCMS calculated for $C_{12}H_{13}F_3N_6O$ (M+H): 315.1. found 315.1.

Example 4

Preparation of 8-bromo-6-pentyl-6,9-dihydro-5H-[1,2,4]triazolo[3,4-i]purin-5-one

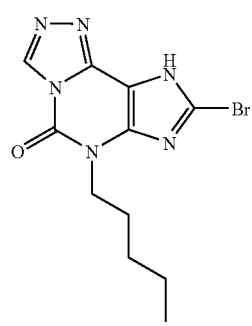

Step A:
2-Amino-7-benzyl-1,7-dihydro-6H-purin-6-one

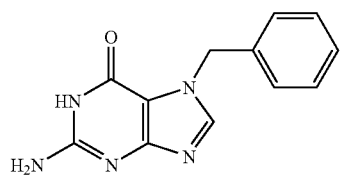

A mixture of 2-amino-9-[(1S,2R,3S,4S)-2,3-dihydroxy-4-(hydroxymethyl)-cyclopentyl]-1,9-dihydro-6H-purin-6-one (60.0 g, 0.213 mol) and benzyl bromide (60.9 mL, 0.512 mol) in DMSO (300 mL) was stirred at room temperature for 18 h. Concentrated HCl aqueous solution (150 mL) was added to the reaction mixture and stirring was continued for 45 min. The resulting mixture was poured into MeOH (1800 ml). The solution was neutralized with 2 M NaOH solution. The resulting white precipitate was collected by filtration, washed with water, and dried under vacuum to afford the product (48 g, 93.3%). LCMS calculated for $C_{12}H_{12}N_5O$ (M+H): 242.1. found: 242.1.

Step B: 7-Benzyl-3,7-dihydro-1H-purine-2,6-dione

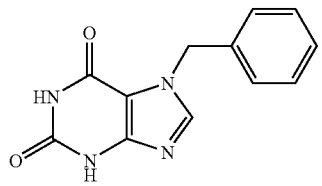

To a mixture of 2-amino-7-benzyl-3,7-dihydro-6H-purin-6-one (25.0 g, 0.104 mol) in acetic acid (750.0 mL) and water (50.0 mL) at 55° C. was added a solution of sodium nitrite (28 g, 0.41 mol) in water (50 ml) dropwise. After the addition, the mixture was continued to stir for about 30 min until no starting material was left and then cooled to room temperature. The reaction mixture was concentrated to about ⅓ of its original volume, then diluted with 250 ml water. The precipitate formed was collected by filtration to provide the desired product (20 g, 79.7%). LCMS calculated for $C_{12}H_{11}N_4O_2$ (M+H): 243.1. found: 243.1.

Step C: 7-Benzyl-3-pentyl-3,7-dihydro-1H-purine-2,6-dione

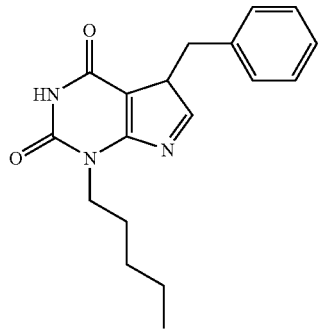

7-Benzyl-3,7-dihydro-1H-purine-2,6-dione (5.0 g, 21 mmol) was mixed with sodium carbonate (3.3 g, 31 mmol) and 1-iodopentane (4.0 mL, 31 mmol) in DMF (60 mL). After being stirred at 40° C. for 18 h, the reaction mixture was diluted with water and EtOAc. The aqueous layer was extracted with EtOAc twice. The combined organic layers were dried, filtered and concentrated. The resulting white solid was collected and dried in vacuum oven at 50° C. for 18 h to provide the desired product (2.84 g, 44% yield). LCMS calculated for $C_{17}H_{21}N_4O_2$ (M+H): 313.2. found: 313.2.

Step D: 7-Benzyl-3-pentyl-6-thioxo-1,3,6,7-tetrahydro-2H-purin-2-one

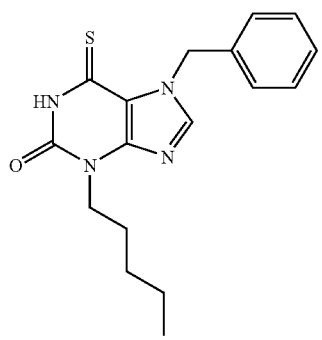

7-Benzyl-3-pentyl-3,7-dihydro-1H-purine-2,6-dione (2.0 g, 6.4 mmol) and phosphorus pentasulfide (3.0 g, 6.7 mmol) were mixed in 1,4-dioxane (20 mL). After stirring at 100° C. for 6 h, the reaction mixture was treated with a 2 M solution of sodium hydroxide in water (20 mL). Then the reaction mixture was adjusted to be acidic (pH ~4) with 2 N HCl and extracted with EtOAc. The organic layer was concentrated, and the solid formed was washed with ether to provide the product as a yellow solid (1.30 g, 61.8% yield). LCMS calculated for $C_{17}H_{21}N_4OS$ (M+H): 329.1. found: 329.1.

Step E: 7-Benzyl-6-(methylthio)-3-pentyl-3,7-dihydro-2H-purin-2-one

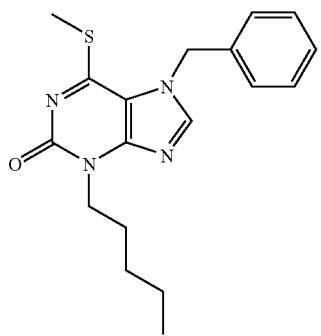

To a mixture of 7-benzyl-3-pentyl-6-thioxo-1,3,6,7-tetrahydro-2H-purin-2-one (5.3 g, 16 mmol) in a solution of sodium hydroxide in water (2 M, 50.0 mL) was added dimethyl sulfate (2.3 mL, 24 mmol). The reaction mixture was stirred at 80° C. overnight, quenched with acetic acid and extracted with dichloromethane (DCM). The organic layer was dried and concentrated to provide the desired product (5.2 g, 98% yield). LCMS calculated for $C_{18}H_{23}N_4OS$ (M+H): 343.2. found: 343.1.

Step F: (6Z)-7-Benzyl-3-pentyl-3,7-dihydro-1H-purine-2,6-dione 6-hydrazone

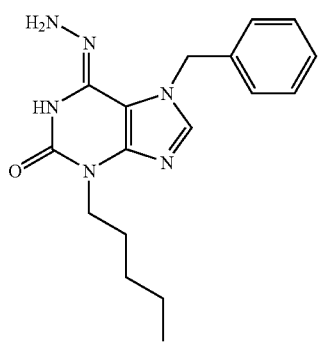

7-Benzyl-6-(methylthio)-3-pentyl-3,7-dihydro-2H-purin-2-one (1.2 g, 3.5 mmol) and hydrazine (10 mL, 100 mmol) were mixed. After being stirred at 100° C. overnight, the solution was concentrated in vacuum. The residue was dissolved in DMSO and purified using preparative LCMS. The product fractions were collected and lyophilized to provide the product as a white powder (0.56 g, 60% yield). LCMS calculated for $C_{17}H_{23}N_6O$ (M+H): 327.2. found: 327.1.

Step G: 9-Benzyl-6-pentyl-6,9-dihydro-5H-[1,2,4]triazolo[3,4-i]purin-5-one

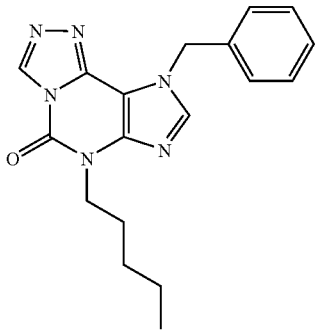

(6Z)-7-Benzyl-3-pentyl-3,7-dihydro-1H-purine-2,6-dione 6-hydrazone (0.50 g, 1.5 mmol) was mixed with ethyl orthoformate (5 mL, 30 mmol). After being stirred at 60° C. for 1 h, the reaction mixture was concentrated in vacuum. The residue was treated with ether to yield the desired product as a white solid (0.25 g, 48.5%). LCMS calculated for $C_{18}H_{21}N_6O$ (M+H): 337.2. found: 337.1.

Step H: 6-Pentyl-6,9-dihydro-5H-[1,2,4]triazolo[3,4-i]purin-5-one

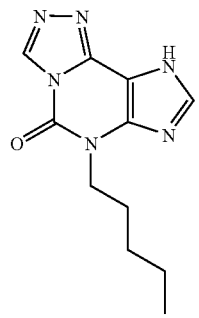

To a mixture of 9-benzyl-6-pentyl-6,9-dihydro-5H-[1,2,4]triazolo[3,4-i]purin-5-one (0.25 g, 0.74 mmol) in acetic acid (20 mL) was added palladium hydroxide (0.20 g, 1.4 mmol) under $N_2$. The mixture was shaken under $H_2$ at 60 psi overnight. Since the reaction was not complete, more palladium hydroxide (0.2 g, 1.4 mmol) and concentrated HCl (1 mL) were added. The resulting mixture was shaken under $H_2$ at 60 psi overnight. The reaction solution was filtered and the filtrate was concentrated under vacuum to provide the product as a white solid (0.12 g, 65.6%). LCMS calculated for $C_{11}H_{15}N_6O$ (M+H): 247.1. found: 247.1.

Step I: 8-Bromo-6-pentyl-6,9-dihydro-5H-[1,2,4]triazolo[3,4-i]purin-5-one

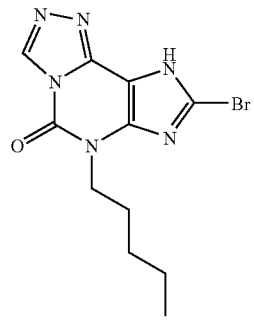

To a mixture of 6-pentyl-6,9-dihydro-5H-[1,2,4]triazolo[3,4-i]purin-5-one (0.12 g, 0.487 mmol) in THF (5 mL) in a microwave reaction tube was added N-bromosuccinimide (0.20 g, 1.1 mmol). The mixture was heated at 70° C. in microwave oven for 12 min. After cooling down to room temperature, it was purified using preparative LCMS to provide the product (0.011 g). LCMS calculated for $C_{11}H_{14}BrN_6O$ (M+H): 325.0, 327.0. found: 325.0, 327.0.

Example 5

Preparation of 8-bromo-6-butyl-6,9-dihydro-5H-[1,2,4]triazolo[3,4-i]purin-5-one

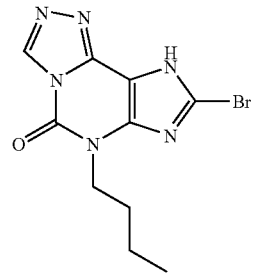

The title compound was prepared using procedures analogous to those described for Example 4. LCMS calculated for $C_{10}H_{12}BrN_6O$ (M+H): 311.0, 313.0. found: 311.0, 313.0.

Example 6

Preparation of 8-bromo-6-butyl-3-methyl-6,9-dihydro-5H-[1,2,4]triazolo[3,4-i]purin-5-one

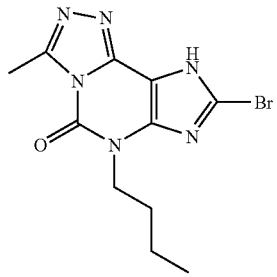

The title compound was prepared using procedures analogous to those described for Example 4. LCMS calculated for $C_{11}H_{14}BrN_6O$ (M+H): 325.0, 327.0. found: 325.0, 327.0.

Example 7

Preparation of 8-bromo-6-pentyl-6,9-dihydro-5H-tetrazolo[5,1-i]purin-5-one

Step A: 7-Allyl-3-pentyl-3,7-dihydro-1H-purine-2,6-dione

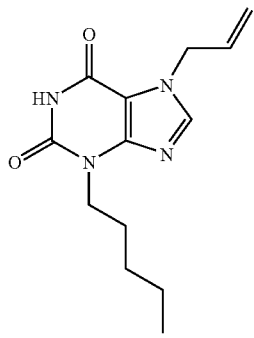

A mixture of 7-allyl-3,7-dihydro-1H-purine-2,6-dione (10.0 g, 0.052 mol), sodium carbonate (8.3 g, 0.078 mol), and 1-iodopentane (12 g, 0.062 mol) in DMF (100 mL) was stirred at 45° C. for 2 days. The reaction mixture was diluted with water and EtOAc. The aqueous layer was extracted with EtOAc three times. The combined organic layers were washed with brine, dried over $Na_2SO_4$ and concentrated. The residue was treated with ether and the solid formed was filtered to provide the desired product as white solid (6.2 g, 45.4%). LCMS calculated for $C_{13}H_{19}N_4O_2$ (M+H): 263.2. found: 263.2.

Step B: 7-Allyl-6-chloro-3-pentyl-3,7-dihydro-2H-purin-2-one

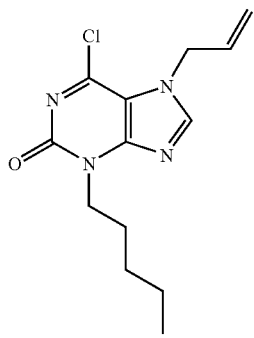

A mixture of 7-allyl-3-pentyl-3,7-dihydro-1H-purine-2,6-dione (0.80 g, 3.0 mmol) and phosphoryl chloride (10.0 mL, 100 mmol) was refluxed for 2 h. The excess phosphoryl chloride was removed by vacuum distillation. The residue was diluted with ice-water, neutralized with solid $K_2CO_3$, and then extracted with DCM three times. The combined organic layers were dried, filtered and concentrated to provide the crude product (0.60 g), which was used for next step without further purification. LCMS calculated for $C_{13}H_{18}ClN_4O$ (M+H): 281.1. found: 281.1.

Step C: 9-Allyl-6-pentyl-6,9-dihydro-5H-tetrazolo[5,1-i]purin-5-one

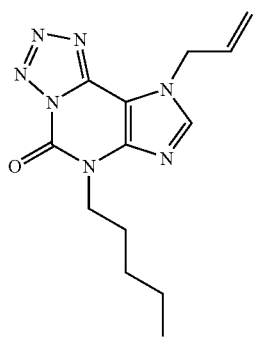

A mixture of 7-allyl-6-chloro-3-pentyl-3,7-dihydro-2H-purin-2-one (0.65 g, 2.3 mmol) and sodium azide (0.98 g, 15 mmol) in ethanol (20 mL) was refluxed overnight. The reaction mixture was concentrated under vacuum. The residue was diluted with water and EtOAc. The organic phase was separated and the aqueous layer was extracted with EtOAc twice. The combined organic layers were dried over $Na_2SO_4$, filtered and concentrated to give the crude product, which was purified by preparative LCMS to provide the desired product as a white powder (0.15 g, 22.6%). LCMS calculated for $C_{13}H_{18}N_7O$ (M+H): 288.2. found: 288.1.

Step D: 6-Pentyl-6,9-dihydro-5H-tetrazolo[5,1-i]purin-5-one

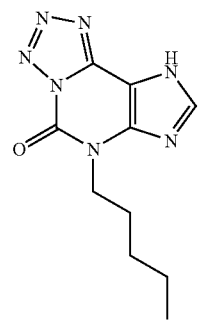

A mixture of 9-allyl-6-pentyl-6,9-dihydro-5H-tetrazolo[5,1-i]purin-5-one (0.10 g, 0.35 mmol) and morpholine (0.2 mL, 2.0 mmol) in THF (3 mL) was degassed for 5 min using $N_2$ and tetrakis(triphenylphosphine)palladium(0) (0.10 g, 0.086 mmol) was added to the mixture. After being stirred at room temperature overnight, the reaction mixture was mixed with 2 M HCl aqueous solution and DCM. The organic layer was separated, dried over $Na_2SO_4$ and concentrated. The residue was purified using preparative LCMS to provide the product as a white powder (0.030 g, 35%). LCMS calculated for $C_{10}H_{14}N_7O$ (M+H): 248.0. found: 248.0.

Step E: 8-Bromo-6-pentyl-6,9-dihydro-5H-tetrazolo[5,1-i]purin-5-one

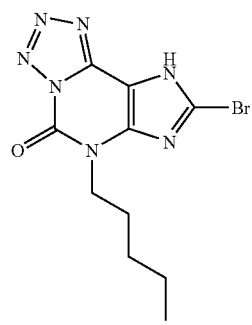

The mixture of 6-pentyl-6,9-dihydro-5H-tetrazolo[5,1-i]purin-5-one (0.020 g, 0.081 mmol) and N-bromosuccinimide (10 mg, 8.0 mmol) in acetonitrile (2 mL) in a 5 mL-microwave reaction tube was heated at 70° C. in microwave oven for 12 min. After cooling down to room temperature, the reaction mixture was purified using preparative LCMS to yield the desired product as a white powder. LCMS calculated for $C_{10}H_{13}BrN_7O$ (M+H): 326.0, 328.0. found: 326.0, 328.0.

Example 8

Preparation of 2-bromo-4-pentyl-8-phenyl-1,4-dihydro-5H-[1,2,4]triazolo[5,1-i]purin-5-one

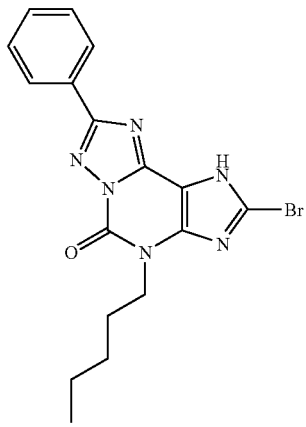

Step A: 4-(pentylamino)-1H-imidazole-5-carbonitrile

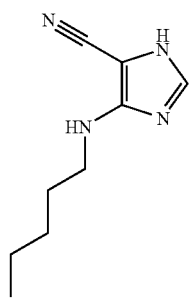

4-amino-1H-imidazole-5-carbonitrile (10.0 g, 0.0925 mol) and pentanal (11 mL, 0.10 mol) were mixed in methanol (100 mL). After stirring at room temperature for 2 hours, Sodium cyanoborohydride (7.0 g, 0.11 mol) was added to the mixture. The mixture was continued to stir overnight. The reaction mixture was concentrated, diluted with EtOAc (1 L) and washed with sat. NaHCO₃ (30 ml) and then brine (50 ml) solutions respectively. The organic layers were dried over Na₂SO₄, concentrated and purified with combi-flash silica gel chromatography (20%-80% EtOAc in hexane) to yield the desired product (11.5 g, 70%). LCMS calculated for $C_9H_{15}N_4$ (M+H): 179. found: 179.1.

Step B: N-pentyl-5-(3-phenyl-1H-1,2,4-triazol-5-yl)-1H-imidazol-4-amine

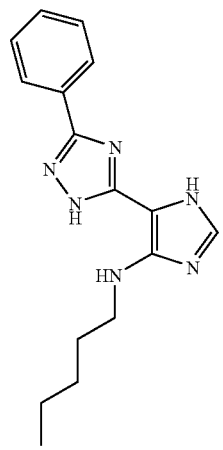

The mixture of 4-(pentylamino)-1H-imidazole-5-carbonitrile (200 mg, 1.12 mmol), benzohydrazide (229 mg, 1.68 mmol) and potassium carbonate (100 mg, 0.72 mmol) in 1-butanol (6 ml) in a sealed tube was stirred at 170° C. for 14 hours. The reaction was diluted with water and extracted with EtOAc three times. The combined organic layers was dried with sodium sulfate, filtered, and concentrated in vacuo. The crude residue was purified by preparative LCMS (method A) to yield the desired product (50 mg, 17% yield). LCMS calculated for $C_{16}H_{21}N_6$ (M+H): 297.2. found 297.1.

Step C: 4-pentyl-8-phenyl-1,4-dihydro-5H-[1,2,4]triazolo[5,1-i]purin-5-one

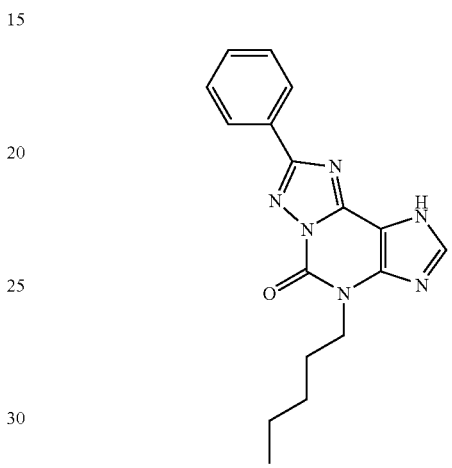

N-pentyl-5-(3-phenyl-1H-1,2,4-triazol-5-yl)-1H-imidazol-4-amine (50 mg, 0.17 mmol) and N,N-carbonyldiimidazole (50 mg, 0.3 mmol) were dissolved in THF (10 mL) and stirred at 70° C. for 2 hours. The reaction mixture was concentrated under reduced pressure, and the residue was purified by preparative LCMS (method B) to yield the desired product (25 mg, 45% yield). LCMS calculated for $C_{17}H_{19}N_6O$ (M+H): 323.2. found 323.1.

Step D: 2-bromo-4-pentyl-8-phenyl-1,4-dihydro-5H-[1,2,4]triazolo[5,1-i]purin-5-one

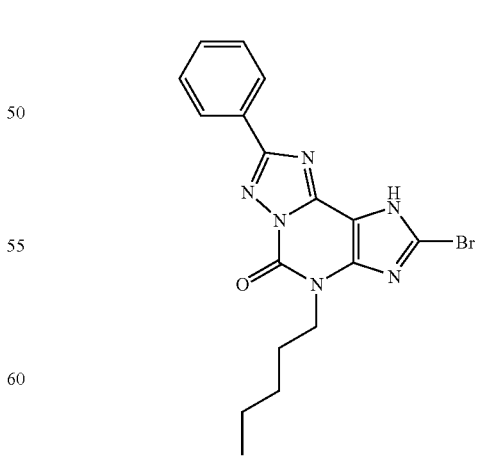

To the mixture of 4-pentyl-8-phenyl-1,4-dihydro-5H-[1,2,4]triazolo[5,1-i]purin-5-one (25 mg, 0.078 mmol) in THF (5 mL) was added N-Bromosuccinimide (19 mg, 0.11 mmol).

After stirring at room temperature for 1 hour, phenol was added to quench the reaction. The reaction mixture was concentrated, and the residue was purified by preparative LCMS (method B) to provide the desired product as white powder. $^1$HNMR (400 MHz, CD$_3$OD): δ 8.25 (m, 2H), 7.50 (m, 3H), 4.31 (t, J=7.3 Hz, 2H), 1.88 (m, 2H), 1.43 (m, 4H), 0.95 (m, 3H). LCMS calculated for C$_{17}$H$_{18}$BrN$_6$O (M+H): 401.1. found: 401.0, 403.0.

Example 9

Preparation of 2-bromo-8-methyl-4-pentyl-1,4-dihydro-5H-[1,2,4]triazolo[5,1-i]purin-5-one

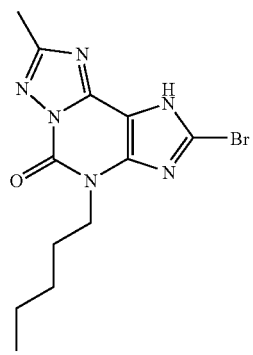

Step A: 5-(3-methyl-1H-1,2,4-triazol-5-yl)-N-pentyl-1H-imidazol-4-amine

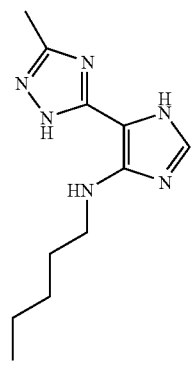

To the mixture of 4-(pentylamino)-1H-imidazole-5-carbonitrile (0.40 g, 2 mmol), acetic acid, hydrazide (0.33 g, 4.5 mmol) in 1-butanol (10 mL) was added potassium carbonate (0.10 g, 0.72 mmol). The mixture was sealed and stirred at 165° C. for 14 hours. The reaction mixture was diluted with water and extracted with ethyl acetate three times. The combined organic layers were dried with sodium sulfate, filtered, and concentrated in vacuo. The residue was purified by preparative LCMS (method A) to yield the desired product (45 mg, 10% yield). LCMS calculated for C$_{11}$H$_{19}$N$_6$(M+H): 235.2. found: 235.1.

Step B: 8-methyl-4-pentyl-1,4-dihydro-5H-[1,2,4]triazolo[5,1-i]purin-5-one

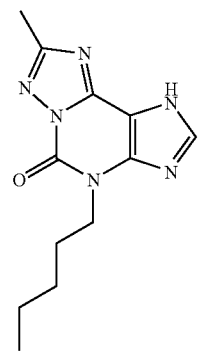

To a solution of 5-(3-methyl-1H-1,2,4-triazol-5-yl)-N-pentyl-1H-imidazol-4-amine (45 mg, 0.19 mmol) in THF (10 mL) at 0° C. was added phosgene in toluene (0.3 mL, 1.0 mmol). The reaction mixture was slowly warmed to room temperature while stirring. The reaction mixture was concentrated under reduced pressure, and the residue was purified by preparative LCMS (method A) to provide the desired product (25 mg, 50% yield) as a white powder. LCMS calculated for C$_{12}$H$_{17}$N$_6$O (M+H): 261.1. found: 261.1.

Step C: 2-bromo-8-methyl-4-pentyl-1,4-dihydro-5H-[1,2,4]triazolo[5,1-i]purin-5-one

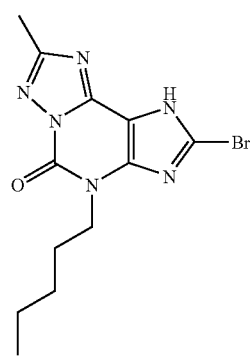

To the mixture of 8-methyl-4-pentyl-1,4-dihydro-5H-[1,2,4]triazolo[5,1-i]purin-5-one (20 mg, 0.078 mmol) in THF (5 mL) was added N-Bromosuccinimide (19 mg, 0.11 mmol). After stirring at room temperature for 1 hour, phenol was added to quench the reaction. The reaction mixture was concentrated at reduced pressure, and the residue was purified by preparative LCMS (method B) to yield the desired product as white powder. LCMS calculated for C$_{12}$H$_{16}$BrN$_6$O (M+H): 339.1. found: 339.0, 341.0.

Example 10

Preparation of 2-bromo-4-pentyl-8-pyridin-4-yl-1,4-dihydro-5H-[1,2,4]triazolo[5,1-i]purin-5-one

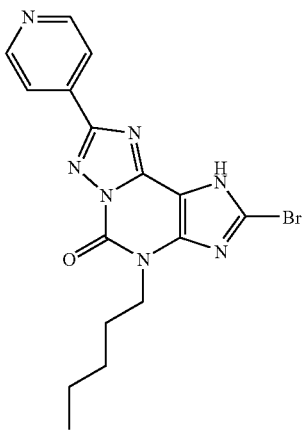

The title compound was prepared using procedures analogous to those described for Example 8. LCMS calculated for $C_{16}H_{17}BrN_7O$ (M+H): 402.1. found: 402.0, 404.0.

Example 11

Preparation of 2-bromo-4-pentyl-8-pyridin-3-yl-1,4-dihydro-5H-[1,2,4]triazolo[5,1-i]purin-5-one

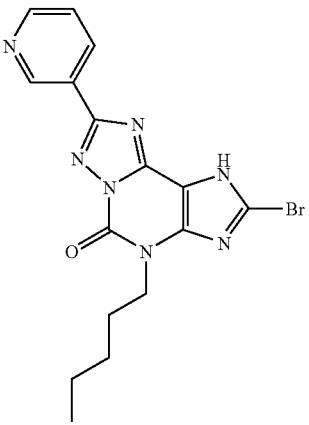

The title compound was prepared using procedures analogous to those described for Example 8. $^1$HNMR (400 MHz, CD$_3$OD): δ 9.41 (s, 1H), 8.66 (m, 2H), 7.59 (m, 1H), 4.30 (t, J=7.9 Hz, 2H), 1.87 (m, 2H), 1.43 (m, 4H), 0.94 (t, J=7.0 Hz, 3H). LCMS calculated for $C_{16}H_{17}BrN_7O$ (M+H): 402.1. found: 402.0, 404.0.

Example 12

Preparation of 8-bromo-3-methyl-6-pentyl-6,9-dihydro-5H-[1,2,4]triazolo[3,4-i]purin-5-one

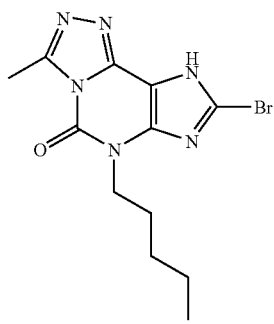

The title compound was prepared using procedures analogous to those described for Example 4. LCMS calculated for $C_{12}H_{16}BrN_6O$ (M+H): 339.1. found: 339.0, 341.0.

Example 13

Preparation of 8-benzyl-2-bromo-4-pentyl-1,4-dihydro-5H-[1,2,4]triazolo[5,1-i]purin-5-one

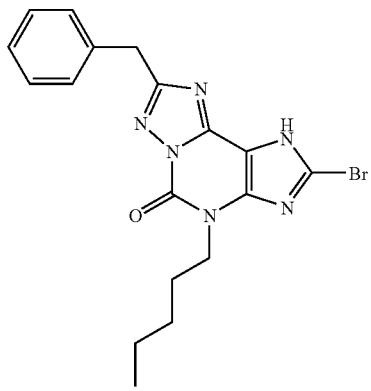

The title compound was prepared using procedures analogous to those described for Example 8. LCMS calculated for $C_{18}H_{19}BrN_6O$ (M+H): 415.1. found: 415.1, 417.1.

Example 14

Preparation of 2-bromo-4-pentyl-8-pyrimidin-4-yl-1,4-dihydro-5H-[1,2,4]triazolo[5,1-i]purin-5-one

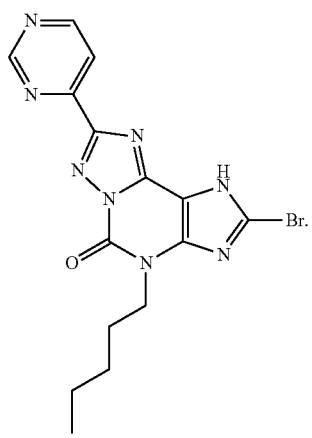

Step A: pyrimidine-4-carbohydrazide

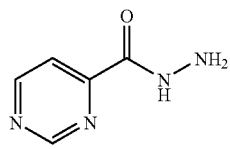

To a solution of pyrimidine-4-carboxylic acid (1.0 g, 8.0 mmol) in THF (15 mL), N,N-Carbonyldiimidazole (1.4 g, 8.9 mmol) was added. After refluxing for 2 hours, hydrazine (0.8 g, 20 mmol) was added to the reaction mixture slowly with a syringe at 0° C. The reaction mixture was allowed to warm to room temperature slowly and then concentrated to yield the desired product as white solid. LCMS calculated for $C_5H_7N_4O$ (M+H): 139.1. found: 139.1.

Step B: N-pentyl-5-(3-pyrimidin-4-yl-1H-1,2,4-triazol-5-yl)-1H-imidazol-4-amine

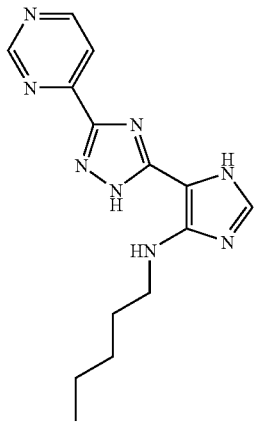

The mixture of methyl 4-(pentylamino)-1H-imidazole-5-carbimidothioate (1.5 g, 6.6 mmol) and pyrimidine-4-carbohydrazide (1.2 g, 8.7 mmol) in ethanol (10 mL) was refluxed overnight. The reaction mixture was concentrated under reduced pressure to yield the desired product as light green viscous oil. LCMS calculated for $C_{14}H_{19}N_8$ (M+H): 299.2. found: 299.1.

Step C: 4-pentyl-8-pyrimidin-4-yl-1,4-dihydro-5H-[1,2,4]triazolo[5,1-i]purin-5-one (14C1) and 6-pentyl-3-pyrimidin-4-yl-6,9-dihydro-5H-[1,2,4]triazolo[3,4-i]purin-5-one (14C2)

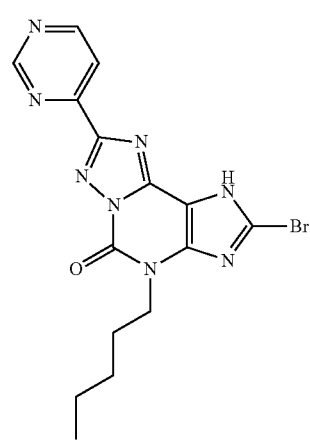

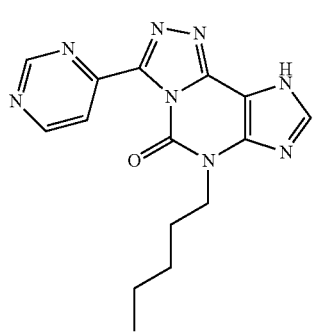

To a solution of N-pentyl-5-(3-pyrimidin-4-yl-1H-1,2,4-triazol-5-yl)-1H-imidazol-4-amine (2.0 g, 6.7 mol) in THF (10 mL), phosgene 20% in toluene (4.2 g, 8.4 mmol) was added slowly with a syringe at room temperature. The reaction mixture was stirred at room temperature for 2 hours. The reaction mixture was concentrated under reduced pressure, and the residue was purified by preparative LCMS (method A) to yield compounds 14C1 and 14C2 (50 mg, 2.3% yield). LCMS calculated for $C_{15}H_{17}N_8O$ (M+H): 325.2. found: 325.1.

Step D: 2-bromo-4-pentyl-8-pyrimidin-4-yl-1,4-dihydro-5H-[1,2,4]triazolo[5,1-i]purin-5-one(14D1) and 8-bromo-6-pentyl-3-pyrimidin-4-yl-6,9-dihydro-5H-[1,2,4]triazolo[3,4-i]purin-5-one(14D2)

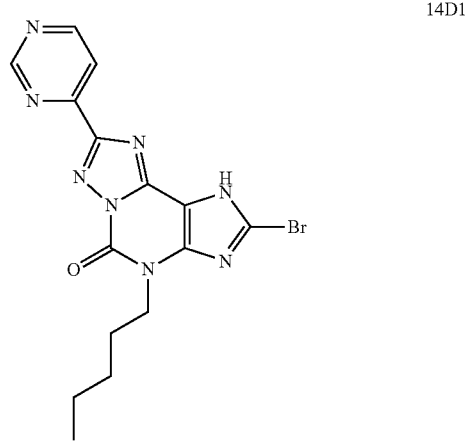

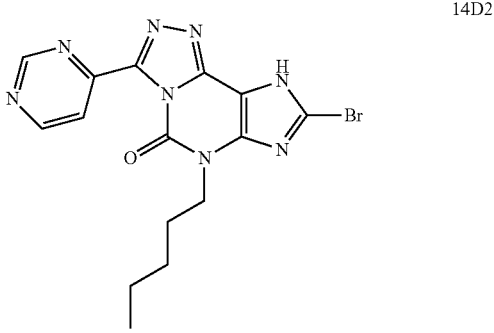

To a mixture of 4-pentyl-8-pyrimidin-4-yl-1,4-dihydro-5H-[1,2,4]triazolo[5,1-i]purin-5-one (14C1) and 6-pentyl-3-pyrimidin-4-yl-6,9-dihydro-5H-[1,2,4]triazolo[3,4-i]purin-5-one (14C2) (25 mg, 0.15 mmol) in THF (5 mL) was added N-bromosuccinimide (19 mg, 0.22 mmol). The reaction mixture was stirred at room temperature for 1 hour, then the reaction was quenched by phenol. After removing the solvent, the residue was purified using preparative LCMS (method B) to yield the pure compound (14D1) and the pure compound 14D2 respectively. LCMS calculated for $C_{15}H_{16}BrN_8O$ (M+H): 403.1. found: 403.0, 405.0.

Example 15

Preparation of 8-bromo-6-pentyl-3-pyrimidin-4-yl-6,9-dihydro-5H-[1,2,4]triazolo[3,4-i]purin-5-one

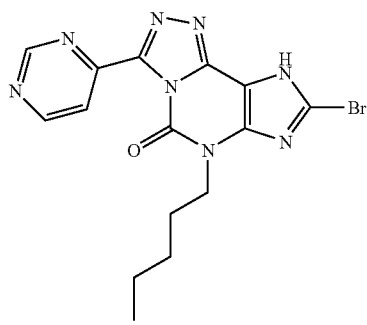

The title compound was prepared using procedures analogous to those described for Example 14. LCMS calculated for $C_{15}H_{16}BrN_8O$ (M+H): 403.1. found: 403.0, 405.0.

Example 16

Preparation of 2-bromo-4-pentyl-8-(trifluoromethyl)-1,4-dihydro-5H-[1,2,4]triazolo[5,1-i]purin-5-one

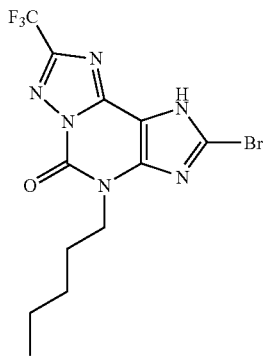

Step A: Trifluoroacetic acid hydrazide

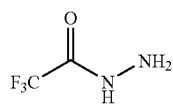

To a solution of hydrazine (1.0 g, 31 mmol) in THF (15 mL) at 0° C. was added trifluoroacetic anhydride (6.6 g, 31 mmol) slowly with a syringe. After warming up to room temperature, the reaction mixture was concentrated to yield the desired product as white solid. LCMS calculated for $C_2H_4F_3N_2O$ (M+H): 129.0. found: 129.0.

Step B: N-pentyl-5-[3-(trifluoromethyl)-1H-1,2,4-triazol-5-yl]-1H-imidazol-4-amine

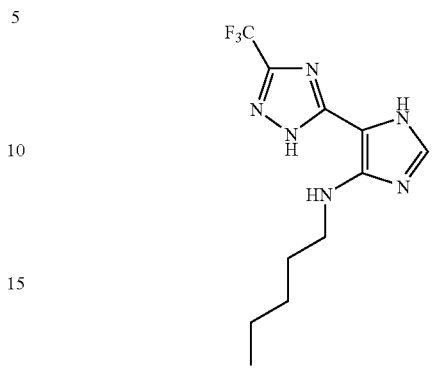

The mixture of methyl 4-(pentylamino)-1H-imidazole-5-carbimidothioate (0.53 g, 2.4 mmol) and trifluoroacetic acid hydrazide (0.45 g, 3.5 mmol) in ethanol (10 mL) was refluxed overnight. The reaction mixture was concentrated to yield the product as slightly green viscous oil. LCMS calculated for $C_{11}H_{16}F_3N_6$ (M+H): 289.1. found: 289.1.

Step C: 4-pentyl-8-(trifluoromethyl)-1,4-dihydro-5H-[1,2,4]triazolo[5,1-i]purin-5-one (C1) and 6-pentyl-3-(trifluoromethyl)-6,9-dihydro-5H-[1,2,4]triazolo[3,4-i]purin-5-one (C2)

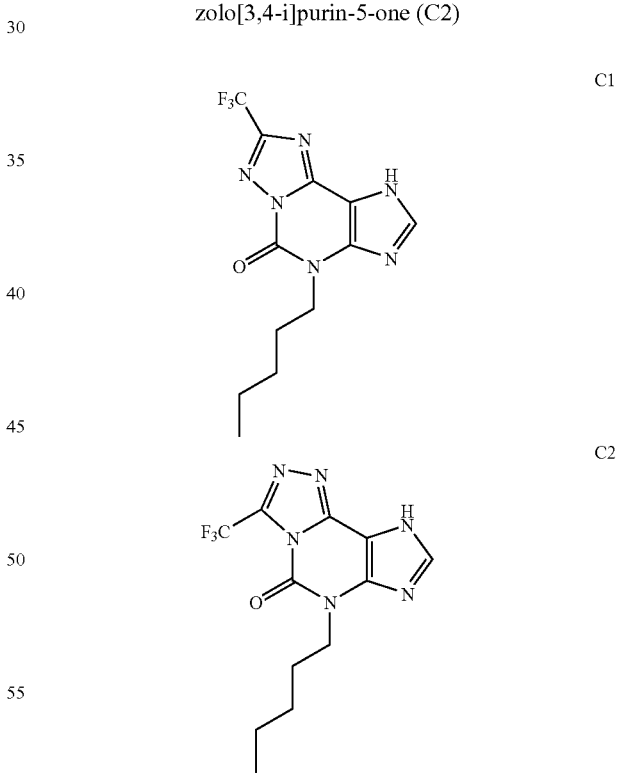

To a mixture of N-pentyl-5-[3-(trifluoromethyl)-1H-1,2,4-triazol-5-yl]-1H-imidazol-4-amine (55 mg, 0.19 mmol) in THF (10 mL) at 0° C. was added 20% phosgene in toluene (0.3 mL, 10 mmol). The reaction mixture was slowly warmed up to room temperature. The reaction mixture was concentrated under reduced pressure. The residue was purified by preparative LCMS (method A) to yield the products as a mixture of C1 and C2 (45 mg, 75% yield). LCMS calculated for $C_{12}H_{14}F_3N_6O$ (M+H): 315.1. found: 315.0.

Step D: 2-bromo-4-pentyl-8-(trifluoromethyl)-1,4-dihydro-5H-[1,2,4]triazolo[5,1-i]purin-5-one (D1) and 8-bromo-6-pentyl-3-(trifluoromethyl)-6,9-dihydro-5H-[1,2,4]triazolo[3,4-i]purin-5-one (D2)

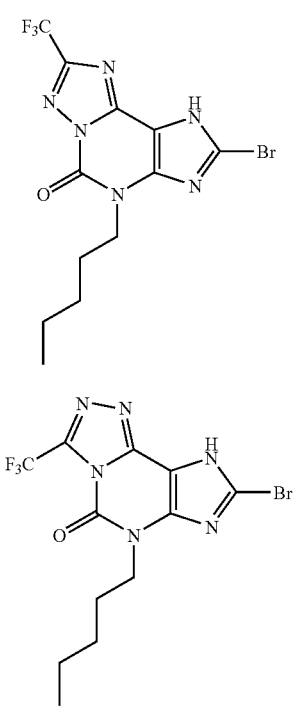

To a mixture of 4-pentyl-8-(trifluoromethyl)-1,4-dihydro-5H-[1,2,4]triazolo[5,1-i]purin-5-one (C1) and 6-pentyl-3-(trifluoromethyl)-6,9-dihydro-5H-[1,2,4]triazolo[3,4-i]purin-5-one (C2) (45 mg, 0.14 mmol) in THF (5 mL) was added N-bromosuccinimide (30 mg, 0.17 mmol). The reaction mixture was stirred at room temperature for 1 hour, and then the reaction was quenched by phenol. After removing the solvent, the residue was purified using preparative LCMS (method B) to yield the pure compound (D1) and compound D2 respectively. LCMS calculated for D1 $C_{12}H_{13}BrF_3N_6O$ (M+H): 393.0. found: 393.0, 395.0.

Example 17

Preparation of 8-bromo-6-pentyl-3-(trifluoromethyl)-6,9-dihydro-5H-[1,2,4]triazolo[3,4-i]purin-5-one

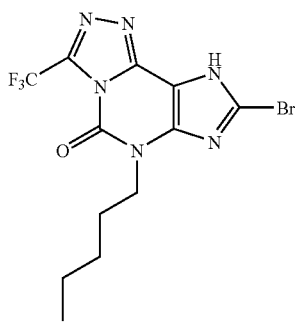

The title compound was prepared using procedures analogous to those described for Example 16. $^1$HNMR (400 MHz, $d_6$-DMSO): δ 4.15 (t, J=7.3 Hz, 2H), 1.73 (m, 2H), 1.31 (m, 4H), 0.85 (t, J=7.0 Hz, 3H). LCMS calculated for $C_{12}H_{13}BrF_3N_6O$ (M+H): 393.0. found: 393.0, 395.0.

Example 18

Preparation of 8-chloro-6-pentyl-3-pyrimidin-4-yl-6,9-dihydro-5H-[1,2,4]triazolo[3,4-i]purin-5-one trifluoroacetate

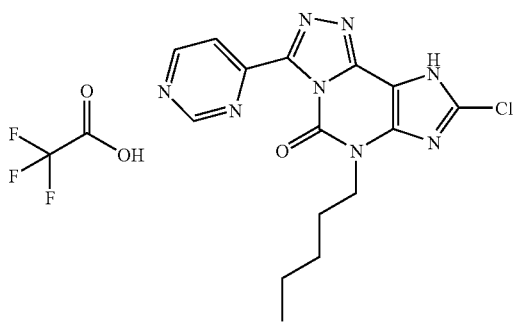

The title compound was prepared using procedures analogous to those described for Example 15. LCMS calculated for $C_{15}H_{16}ClN_8O$ (M+H): 359.1. found: 359.1.

Example 19

Preparation of 2-chloro-8-methyl-4-pentyl-1,4-dihydro-5H-[1,2,4]triazolo[5,1-i]purin-5-one

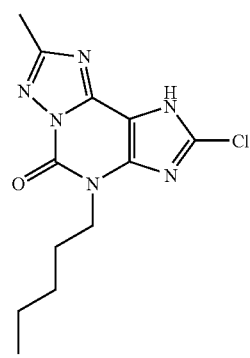

The title compound was prepared using procedures analogous to those described for Example 9. $^1$HNMR (400 MHz, $d_6$-DMSO): δ 4.10 (t, J=7.5 Hz, 2H), 3.4 (br, 1H), 2.40 (s, 3H), 1.70 (m, 2H), 1.29 (m, 4H), 0.84 (t, J=7.5 Hz, 3H). LCMS calculated for $C_{12}H_{16}ClN_6O$ (M+H): 295.1. found: 295.1.

Example 20

Preparation of 2-chloro-4-pentyl-8-pyrimidin-4-yl-1,4-dihydro-5H-[1,2,4]triazolo[5,1-i]purin-5-one trifluoroacetate

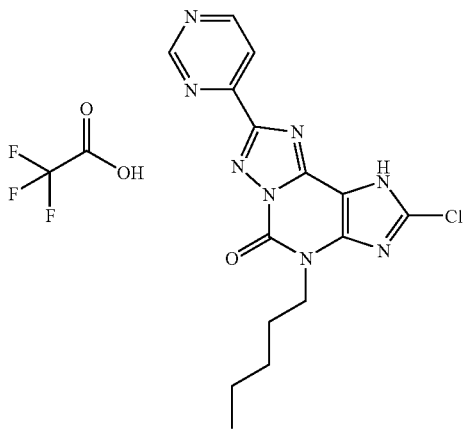

The title compound was prepared using procedures analogous to those described for Example 14. LCMS calculated for $C_{15}H_{16}ClN_8O$ (M+H): 359.1. found: 359.1.

Example 21

Preparation of 8-[2-(3-benzyl-1,2,4-oxadiazol-5-yl)ethyl]-2-bromo-4-butyl-1,4-dihydro-5H-[1,2,4]triazolo[5,1-i]purin-5-one

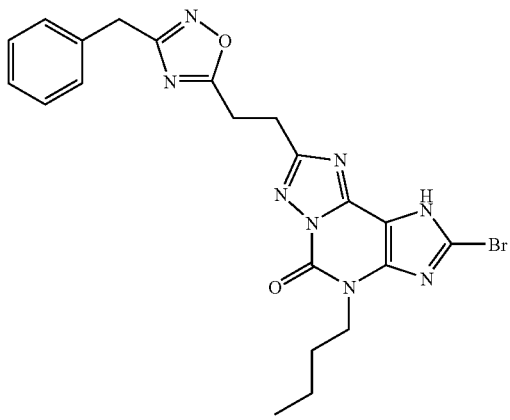

Step A: methyl 3-(3-benzyl-1,2,4-oxadiazol-5-yl)propanoate

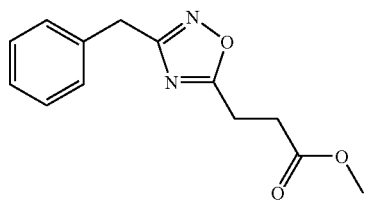

Butanedioic acid, monomethyl ester (4.0 g, 30.3 mmole) and CDI (5.40 g, 33.3 mmole) were dissolved in anhydrous DMF (15 ml) and stirred at room temperature for 3 hours. (1Z)-N'-hydroxy-2-phenylethanimidamide (5.0 g, 33.3 mmole) was added to above solution and the mixture was stirred at 90° C. for 20 hours. The reaction mixture was concentrated and the residue was diluted with water and EtOAc. The organic layer was washed with water and brine, dried over $Na_2SO_4$, filtered and concentrated. The residue was purified by flash chromatography (elution with 1:3 ethyl acetate:hexane) to give the desired product as light yellowish oil (5.2 g, 70% yield). LCMS calculated for $C_{13}H_{15}N_2O_3$ (M+H): 247.1. found: 247.1.

Step B: 3-(3-benzyl-1,2,4-oxadiazol-5-yl)propanoic acid

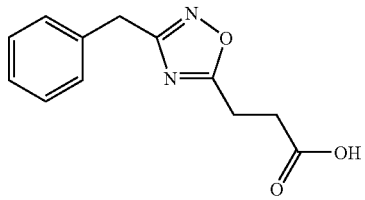

To a solution of methyl 3-(3-benzyl-1,2,4-oxadiazol-5-yl)propanoate (5.2 g, 21.1 mmole) in methanol (30 ml) was added 50 ml of 1N NaOH aqueous solution. The mixture was stirred at room temperature for 2 hours. After the reaction solution was adjusted to be acidic (pH=3-4) at 0° C., the reaction mixture was extracted with EtOAc 3 times. The combined organic layers were washed with water and brine, dried over $Na_2SO_4$, filtered and concentrated to give the desired product as colorless oil (4.8 g, 98%). LCMS calculated for $C_{12}H_{13}N_2O_3$ (M+H): 233.1. found: 233.1.

Step C: 3-(3-benzyl-1,2,4-oxadiazol-5-yl)propanohydrazide

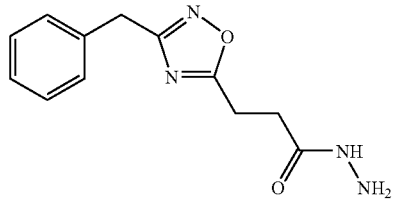

To a solution of 3-(3-benzyl-1,2,4-oxadiazol-5-yl)propanoic acid (1.0 g, 4.3 mmol) in THF (15 mL) was added N,N-carbonyldiimidazole (0.77 g, 4.7 mmol). After refluxing for 2 hours, hydrazine (0.6 g, 20 mmol) was added to the reaction mixture slowly with syringe at 0° C. The reaction mixture was allowed to warm to room temperature slowly and then concentrated to yield the desired product as white solid. LCMS calculated for $C_{12}H_{15}N_4O_2$ (M+H): 247.1. found: 247.1.

Step D: 5-3-[2-(3-benzyl-1,2,4-oxadiazol-5-yl)ethyl]-1H-1,2,4-triazol-5-yl-N-butyl-1H-imidazol-4-amine

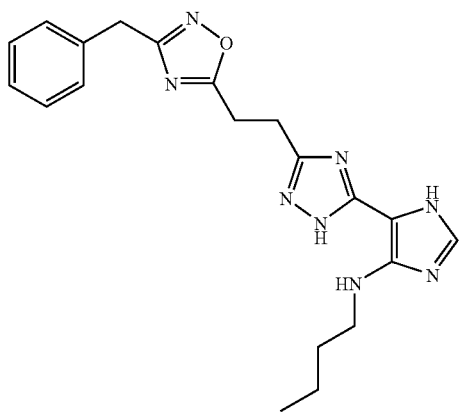

The mixture of methyl 4-(butylamino)-1H-imidazole-5-carbimidothioate (0.80 g, 3.8 mmol) and 3-(3-benzyl-1,2,4-oxadiazol-5-yl)propanohydrazide (1.1 g, 4.5 mmol) in ethanol (20 mL) was refluxed overnight. The reaction mixture was concentrated to give the desired product as lightly green viscous oil. LCMS calculated for $C_{20}H_{25}N_8O$ (M+H): 393.2. found: 393.1.

Step E: 8-[2-(3-benzyl-1,2,4-oxadiazol-5-yl)ethyl]-4-butyl-1,4-dihydro-5H-[1,2,4]triazolo[5,1-i]purin-5-one

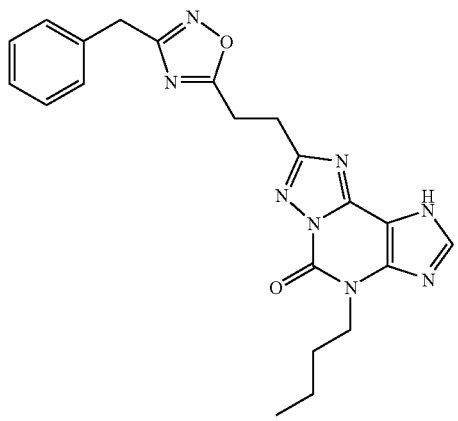

The solution of 5-3-[2-(3-benzyl-1,2,4-oxadiazol-5-yl)ethyl]-1H-1,2,4-triazol-5-yl-N-butyl-1H-imidazol-4-amine (0.90 g, 2.3 mmol) and N,N-carbonyldiimidazole (CDI, 1.0 g, 6.2 mmol) in 1,4-dioxane (10 mL) was stirred at 110° C. for 2 hours. The reaction mixture was concentrated, and the residue was purified by preparative LCMS (method A) to give the desired product as a white powder (80 mg, 8.3% yield). LCMS calculated for $C_{21}H_{23}N_8O_2$ (M+H): 419.2. found: 419.1.

Step F: 8-[2-(3-benzyl-1,2,4-oxadiazol-5-yl)ethyl]-2-bromo-4-butyl-1,4-dihydro-5H-[1,2,4]triazolo[5,1-i]purin-5-one

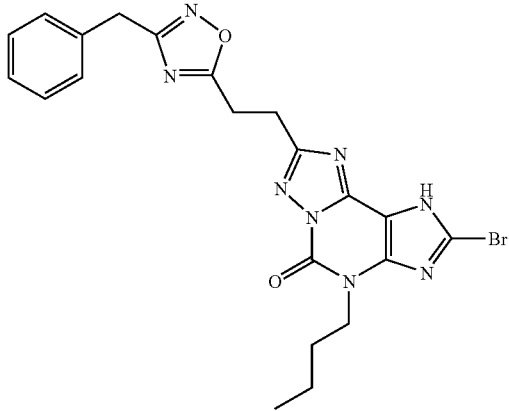

To a mixture of 8-[2-(3-benzyl-1,2,4-oxadiazol-5-yl)ethyl]-4-butyl-1,4-dihydro-5H-[1,2,4]triazolo[5,1-i]purin-5-one (40 mg, 0.096 mmol) in THF (5 mL) was added N-bromosuccinimide (19 mg, 0.11 mmol). After stirring at room temperature overnight, the reaction was quenched with phenol. The reaction mixture was concentrated, and the residue was purified by preparative LCMS (method A) to give desired product as white powder. LCMS calculated for $C_{21}H_{22}BrN_8O_2$ (M+H): 497.1. found: 497.0, 499.0.

Example 22

Preparation of 8-[2-(3-benzyl-1,2,4-oxadiazol-5-yl)ethyl]-4-butyl-2-chloro-1,4-dihydro-5H-[1,2,4]triazolo[5,1-i]purin-5-one

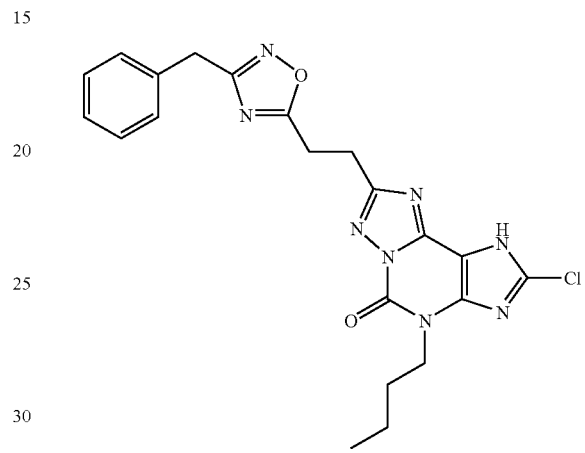

The title compound was prepared using procedures analogous to those described for Example 21. LCMS calculated for $C_{21}H_{22}ClN_8O_2$ (M+H): 453.2. found: 453.2.

Example 23

Preparation of 2-bromo-4-butyl-8-[(4-pyridin-4-ylphenoxy)methyl]-1,4-dihydro-5H-[1,2,4]triazolo[5,1-i]purin-5-one trifluoroacetate

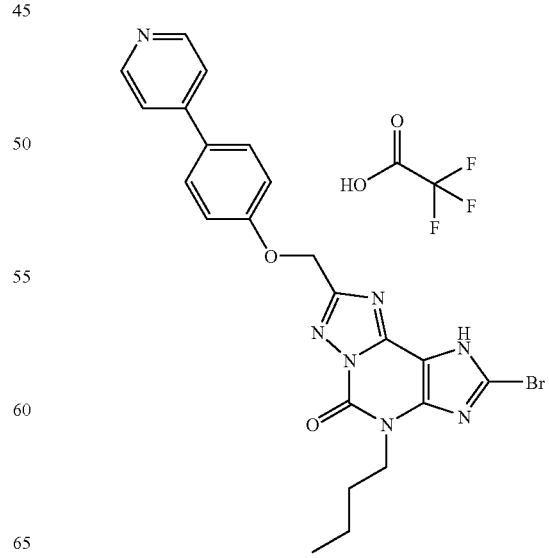

Step A: 2-(4-bromophenoxy)acetohydrazide

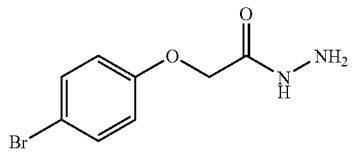

To a solution of (4-bromophenoxy)acetic acid (1.0 g, 4.3 mmol) in THF (15 mL) was added N,N-Carbonyldiimidazole (0.84 g, 5.2 mmol). After refluxing for 2 hours, hydrazine (0.6 g, 20 mmol) was added to the reaction mixture slowly with a syringe at 0° C. The reaction mixture was allowed to warm to room temperature slowly and then concentrated to yield the desired product as a white solid. LCMS calculated for $C_8H_{10}BrN_2O_2$ (M+H): 245.0. found: 244.9, 246.9.

Step B: 5-3-[(4-bromophenoxy)methyl]-1H-1,2,4-triazol-5-yl-N-butyl-1H-imidazol-4-amine

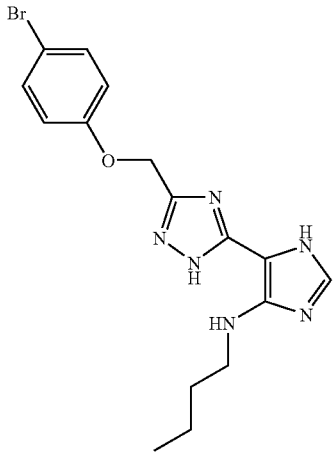

A mixture of methyl 4-(butylamino)-1H-imidazole-5-carbimidothioate (0.80 g, 3.8 mmol), and 2-(4-bromophenoxy)acetohydrazide (1.0 g, 4.1 mmol) in ethanol (10 mL) was refluxed overnight. The reaction mixture was concentrated and the residue was purified using Combi-flash chromatography (elution: EtOAc/methanol) to yield the desired product as a brown oil (1.1 g, 74%). LCMS calculated for $C_{16}H_{20}BrN_6O$ (M+H): 391.1. found: 391.0, 393.0.

Step C: 8-[(4-bromophenoxy)methyl]-4-butyl-1,4-dihydro-5H-[1,2,4]triazolo[5,1-i]purin-5-one

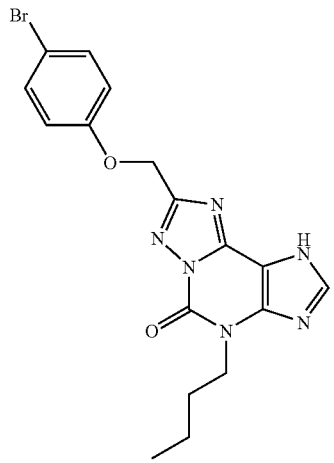

A solution of 5-3-[(4-bromophenoxy)methyl]-1H-1,2,4-triazol-5-yl-N-butyl-1H-imidazol-4-amine (1.1 g, 2.8 mmol) and N,N-Carbonyldiimidazole (0.68 g, 4.2 mmol) in 1,4-dioxane (20 mL) was stirred at 110° C. for 2 hours. The reaction mixture was concentrated, and the residue was purified by preparative LCMS (method A) to give the desired product as a white powder (0.40 g, 38% yield). LCMS calculated for $C_{17}H_{18}BrN_6O_2$(M+H): 417.1. found: 417.1, 419.1.

Step D: 4-butyl-8-[(4-pyridin-4-ylphenoxy)methyl]-1,4-dihydro-5H-[1,2,4]triazolo[5,1-i]purin-5-one

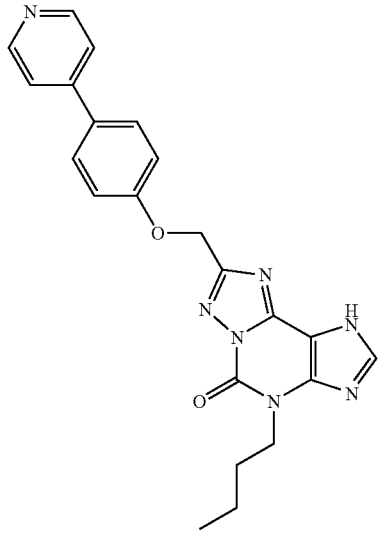

8-[(4-bromophenoxy)methyl]-4-butyl-1,4-dihydro-5H-[1,2,4]triazolo[5,1-i]purin-5-one (100 mg, 0.24 mmol) and 4-pyridinylboronic acid (32 mg, 0.26 mol) were dissolved in N,N-dimethylformamide (3 mL) in a microwave tube. After the solution was degassed with $N_2$ for 5 minutes, dibromo[bis(triphenylphosphoranyl)]-palladium (20 mg, 0.02 mmol) and a solution of sodium carbonate in water (2 M, 1 mL) were added. The reaction mixture was heated on a microwave reactor at 120° C. for 20 minutes. After cooling down to room temperature, the reaction mixture was diluted with water and EtOAc. The aqueous layer was extracted with EtOAc. The combined organic layers were concentrated. The residue was dissolved in DMSO/acetonitrile and purified by preparative LCMS (method A) to yield the desired product as white powder (30 mg, 24% yield). LCMS calculated for $C_{22}H_{22}N_7O_2$ (M+H): 416.2. found: 417.1.

Step E: 2-bromo-4-butyl-8-[(4-pyridin-4-ylphenoxy)methyl]-1,4-dihydro-5H-[1,2,4]triazolo[5,1-i]purin-5-one trifluoroacetate

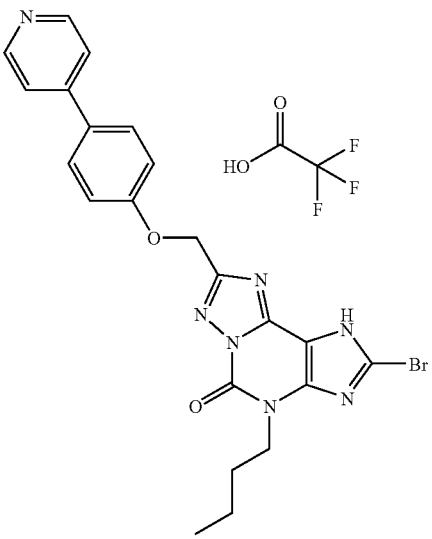

To a mixture of 4-butyl-8-[(4-pyridin-4-ylphenoxy)methyl]-1,4-dihydro-5H-[1,2,4]triazolo[5,1-i]purin-5-one (25 mg, 0.060 mmol) in THF (5 mL) was added N-bromosuccinimide (13 mg, 0.072 mmol). The reaction mixture was stirred at room temperature overnight and then quenched by phenol. The reaction mixture was concentrated, and the residue was purified by preparative LCMS (method A) to yield the desired product as white powder. LCMS calculated for $C_{22}H_{21}BrN_7O_2$ (M+H): 494.1. found: 494.0, 496.0.

Example 24

Preparation of 4'-[(2-bromo-4-butyl-5-oxo-4,5-dihydro-1H-[1,2,4]triazolo[5,1-i]purin-8-yl)methoxy]biphenyl-3-carbonitrile

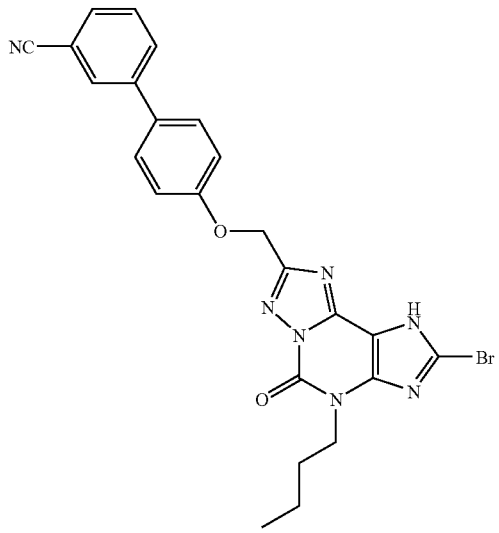

The title compound was prepared using procedures analogous to those described for Example 23. LCMS calculated for $C_{24}H_{21}BrN_7O_2$ (M+H): 518.1. found: 518.1, 520.1.

Example 25

Preparation of 2-bromo-4-butyl-8-[(4-pyridin-3-ylphenoxy)methyl]-1,4-dihydro-5H-[1,2,4]triazolo[5,1-i]purin-5-one trifluoroacetate

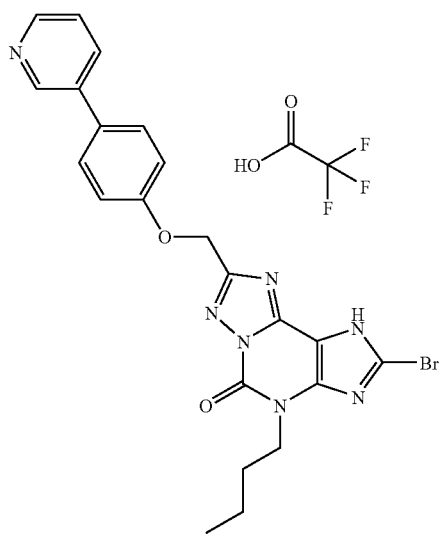

The title compound was prepared using procedures analogous to those described for Example 23. LCMS calculated for $C_{22}H_{21}BrN_7O_2$ (M+H): 494.1. found: 494.1, 496.1.

Example 26

Preparation of 2-bromo-4-pentyl-1,4-dihydro-5H-[1,2,4]triazolo[5,1-i]purin-5-one

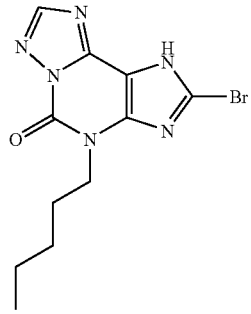

Step A: 4-(Pentylamino)-1H-imidazole-5-carbothioamide

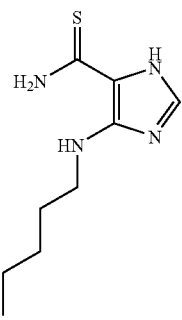

A mixture of 4-(pentylamino)-1H-imidazole-5-carbonitrile (25 g, 0.14 mol), sodium hydrogen sulfide dihydrate (26 g, 0.28 mol) and ammonium chloride (7.5 g, 0.14 mol) in methanol (400 mL) was stirred at room temperature overnight. The conversion was about 60% according to analytical LCMS. The mixture was then stirred at 50° C. for 3 hours. The methanol was removed and the residue was diluted with water and EtOAc. The organic layer was washed with water and brine respectively, dried and concentrated to yield the crude product (30.0 g), which was used for next step without further purification. LCMS calculated for $C_9H_{17}N_4S$ (M+H): 213.1. found: 213.1.

Step B: Methyl 4-(pentylamino)-1H-imidazole-5-carbimidothioate

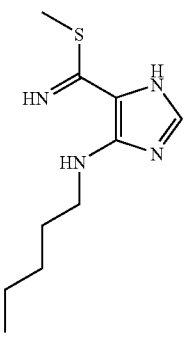

To a solution of 4-(pentylamino)-1H-imidazole-5-carbothioamide (1.0 g, 4.7 mmol) in acetone (40 mL) was added methyl iodide (0.80 g, 5.6 mmol) dropwise. The mixture was stirred at room temperature overnight. The solvent was removed and the residue was diluted with water and ethyl acetate. The organic layer was washed with water and brine, dried and concentrated to yield the crude product (1.2 g), which was used for next step without further purification. LCMS calculated for $C_{10}H_{19}N_4S$ (M+H): 227.1. found: 227.1.

Step C: N-Pentyl-5-(1H-1,2,4-triazol-5-yl)-1H-imidazol-4-amine

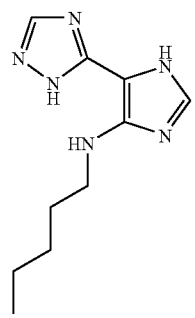

A mixture of methyl 4-(pentylamino)-1H-imidazole-5-carbimidothioate (0.53 g, 2.4 mmol) and formic hydrazide (0.21 g, 3.5 mmol) in ethanol (10 mL) was refluxed overnight. The reaction mixture was concentrated under reduced pressure to yield the desired product as a slightly green viscose oil. LCMS calculated for $C_{10}H_{17}N_6$ (M+H): 221.2. found: 221.1.

Step D: 4-Pentyl-1,4-dihydro-5H-[1,2,4]triazolo[5,1-i]purin-5-one

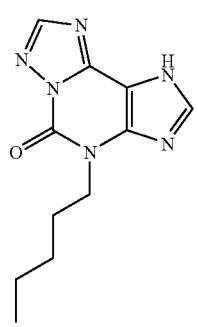

A mixture of N-pentyl-5-(1H-1,2,4-triazol-5-yl)-1H-imidazol-4-amine (0.52 g, 2.4 mmol) and N,N-carbonyldiimidazole (0.57 g, 3.5 mmol) in 1,4-dioxane (10 mL) was stirred at 110° C. for 2 hours. The solvent was removed under reduced pressure, and the residue was purified by preparative LCMS to yield the desire product (30 mg, 5% yield). LCMS calculated for $C_{11}H_{15}N_6O$ (M+H): 247.1. found: 247.1.

Step E: 2-Bromo-4-pentyl-1,4-dihydro-5H-[1,2,4]triazolo[5,1-i]purin-5-one

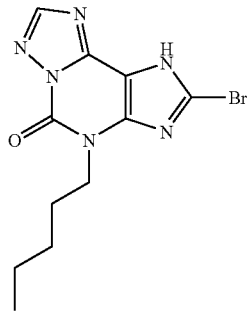

To a mixture of 4-pentyl-1,4-dihydro-5H-[1,2,4]triazolo[5,1-i]purin-5-one (20 mg, 0.081 mmol) in THF (5 mL) was added N-bromosuccinimide (19 mg, 0.11 mol). The reaction mixture was stirred at room temperature for 1 hour and then quenched by phenol. After removing solvent, the residue was purified by preparative LCMS (method B) to yield the desired product. $^1$HNMR (400 MHz, CD$_3$OD): δ 8.30 (s, 1H), 4.30 (t, J=7.4 Hz, 2H), 1.86 (m, 2H), 1.41 (m, 4H), 0.93 (t, J=7.0 Hz, 3H). LCMS calculated for $C_{11}H_{14}BrN_6O$ (M+H): 325.0. found: 325.0, 327.0.

Example 27

Preparation of 2-bromo-4-butyl-8-methyl-1,4-dihydro-5H-[1,2,4]triazolo[5,1-i]purin-5-one

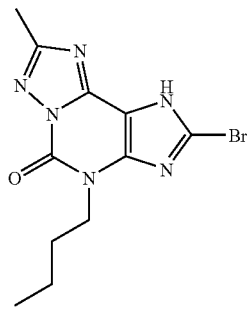

The title compound was prepared using procedures analogous to those described for Example 26. $^1$HNMR (400 MHz, d$_6$-DMSO): δ 4.01 (t, J=7.3 Hz, 2H), 2.72 (s, 3H), 1.66 (m, 2H), 1.32 (m, 2H), 0.89 (t, J=7.4 Hz, 3H). LCMS calculated for $C_{11}H_{14}BrN_6O$ (M+H): 325.0. found: 325.1, 327.1.

Example 28

Preparation of 2-chloro-8-methyl-4-propyl-1,4-dihydro-5H-[1,2,4]triazolo[5,1-i]purin-5-one

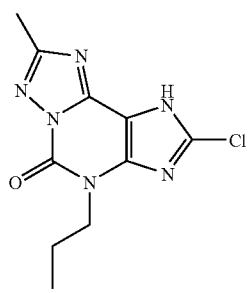

The title compound was prepared using procedures analogous to those described for Example 26. $^1$HNMR (300 MHz, CD$_3$OD): δ 4.20 (t, J=7.6 Hz, 2H), 2.46 (s, 3H), 1.85 (m, 2H), 1.00 (t, J=7.5 Hz, 3H). LCMS calculated for C$_{10}$H$_{12}$ClN$_6$O (M+H): 267.1. found: 267.1.

Example 29

Preparation of 2-bromo-8-methyl-4-propyl-1,4-dihydro-5H-[1,2,4]triazolo[5,1-i]purin-5-one

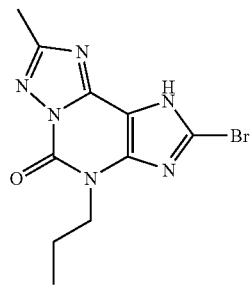

The title compound was prepared using procedures analogous to those described for Example 26. $^1$HNMR (400 MHz, CD$_3$OD): δ 4.23 (t, J=7.3 Hz, 2H), 2.49 (s, 3H), 1.86 (m, 2H), 1.01 (t, J=7.4 Hz, 3H). LCMS calculated for C$_{10}$H$_{12}$BrN$_6$O (M+H): 311.0. found: 311.0, 313.0.

Example 30

Preparation of 4-butyl-2-chloro-8-methyl-1,4-dihydro-5H-[1,2,4]triazolo[5,1-i]purin-5-one

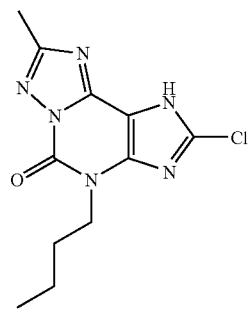

The title compound was prepared using procedures analogous to those described for Example 26. $^1$HNMR (300 MHz, CD$_3$OD): δ 4.28 (t, J=7.7 Hz, 2H), 2.51 (s, 3H), 1.82 (m, 2H), 1.44 (m, 2H), 0.99 (t, J=7.4 Hz, 3H). LCMS calculated for C$_{11}$H$_{14}$ClN$_6$O (M+H): 281.1. found: 281.1.

Example 31

Preparation of 8-bromo-6-pentyl-3-methyl-6,9-dihydro-5H-[1,2,4]triazolo[3,4-i]purin-5-one

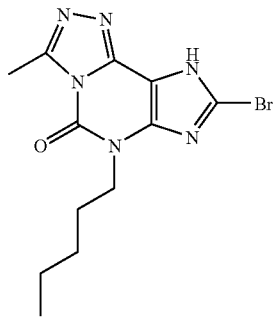

The title compound was prepared using procedures analogous to those described for Example 4. LCMS calculated for C$_{12}$H$_{16}$BrN$_6$O (M+H): 339.0, 341.0. found: 339.0, 341.0.

Example 32

Preparation of 8-bromo-6-isobutyl-6,7-dihydro-5H-[1,2,4]triazolo[3,4-i]purin-5-one

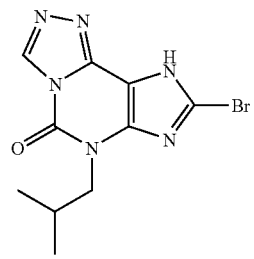

Step A: 2,6-dichloro-9-(tetrahydro-2H-pyran-2-yl)-9H-purine

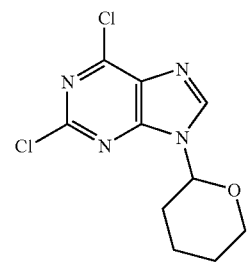

A suspension of 2,6-dichloropurine (22.0 g, 116.4 mmol), dihydropyran (11.5 mL, 126 mmol) and D-(+)-10-camphorsulfonic acid (2.20 g, 9.47 mmol) in 1,2-dichloroethane (300 mL) was stirred at 83° C. for 16 hours. The initially white suspension, after 2 hrs, turned yellow and then black. The reaction mixture was diluted with CCl$_3$H and then washed with brine. The organic layer is dried over MgSO$_4$, filtered, concentrated and triturated with hexane 3 times to give the desired product. $^1$HNMR (300 MHz, CCl$_3$D): δ 8.33 (s, 1H), 5.75 (dd, J=10.4 Hz, 2.5 Hz, 1H), 4.18 (m, 2H), 3.79 (m, 2H), 1.84 (m, 4H).

Step B: 2-chloro-6-hydrazino-9-(tetrahydro-2H-pyran-2-yl)-9H-purine

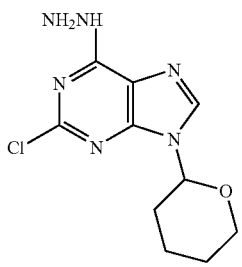

To a suspension of 2,6-dichloro-9-(tetrahydro-2H-pyran-2-yl)-9H-purine (5 g, 20 mmol) in 1-butanol (75 mL) was added hydrazine hydrate (2.0 ml, 40 mmol) at room temperature. The mixture was stirred at 80° C. for 4 hours. The reaction mixture was concentrated under reduced pressure to give the desired product. LCMS calculated for $C_{10}H_{14}ClN_6O$ (M+H): 269.1. found: 269.0.

Step C: 5-chloro-7-(tetrahydro-2H-pyran-2-yl)-7H-[1,2,4]triazolo[3,4-i]purine

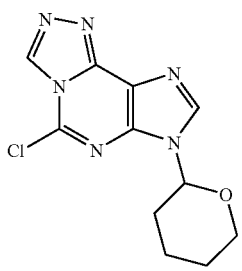

A mixture of (6Z)-2-chloro-9-(tetrahydro-2H-pyran-2-yl)-1,9-dihydro-6H-purin-6-one hydrazone [which is a tautomeric form of 2-chloro-6-hydrazino-9-(tetrahydro-2H-pyran-2-yl)-9H-purine; 0.1 g, 0.5 mmol] and ethyl orthoformate (3 g, 20 mmol) was stirred at 98° C. for 12 hours. The reaction mixture was concentrated under reduced pressure to provide the product. LCMS calculated for $C_{11}H_{12}ClN_6O$ (M+H): 279.1. found: 279.0.

Step D: 7-(tetrahydro-2H-pyran-2-yl)-6,7-dihydro-5H-[1,2,4]triazolo[3,4-i]purin-5-one

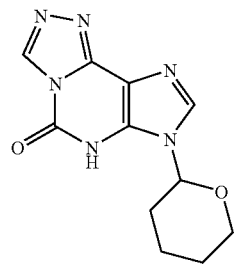

To the solution of 5-chloro-7-(tetrahydro-2H-pyran-2-yl)-7H-[1,2,4]triazolo[3,4-i]purine (0.17 g, 0.50 mmol) in THF (10 mL) was added lithium hydroxide (420 mg, 18 mmol) and water (10 mL). After stirring at room temperature for 10 minutes, the reaction mixture was concentrated under reduced pressure to give the product, which is used for next step without further purification. LCMS calculated for $C_{11}H_{13}N_6O_2$ (M+H): 261.1. found: 261.0.

Step E: 6-isobutyl-7-(tetrahydro-2H-pyran-2-yl)-6,7-dihydro-5H-[1,2,4]triazolo[3,4-i]purin-5-one

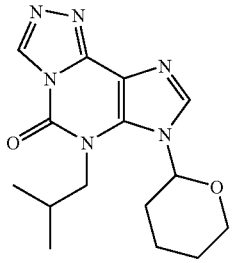

To a solution of 7-(tetrahydro-2h-pyran-2-yl)-6,7-dihydro-5h-[1,2,4]triazolo[3,4-i]purin-5-one (2.08 g, 4.0 mmol) in DMF (20 ml), was added potassium carbonate (1.10 g, 8.0 mmol) and isobutyl iodide (1.47 g, 8.0 mmol). The mixture was stirred at room temperature overnight. The reaction was diluted with water and extracted with EtOAc three times. The combined organic layers was dried with sodium sulfate, filtered, and concentrated in vacuo to give the product. LCMS calculated for $C_{15}H_{21}N_6O_2$ (M+H): 317.2. found: 317.1.

Step F: 6-isobutyl-6,7-dihydro-5H-[1,2,4]triazolo[3,4-i]purin-5-one

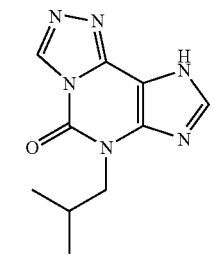

To a solution of 6-isobutyl-7-(tetrahydro-2H-pyran-2-yl)-6,7-dihydro-5H-[1,2,4]triazolo[3,4-i]purin-5-one (20 mg, 0.06 mmol) in methylene chloride (0.8 mL) was added TFA (0.1 mL, 1 mmol) dropwise. After stirring at room temperature for 30 minutes, the reaction mixture was concentrated to give the crude product which was used for next step without further purification. LCMS calculated for $C_{10}H_{13}N_6O$ (M+H): 233.1. found: 233.1.

Step G: 8-bromo-6-isobutyl-6,7-dihydro-5H-[1,2,4]triazolo[3,4-i]purin-5-one

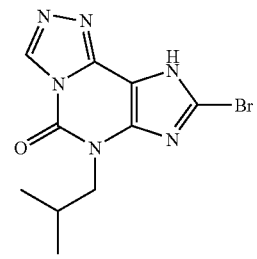

To a solution of 6-isobutyl-6,7-dihydro-5h-[1,2,4]triazolo[3,4-i]purin-5-one (9.4 mg, 40 mmol) in THF (5 ml) was added N-bromosuccinimide (8 mg, 44.7 mmol). The mixture was stirred at room temperature for 30 minutes. The reaction mixture was concentrated, and the residue was purified by preparative LCMS (method A) to provide the desired product. LCMS calculated for $C_{10}H_{12}BrN_6O$ (M+H): 311.0. found 310.9, 313.0.

Example 33

5-(8-bromo-5-oxo-5H-[1,2,4]triazolo[3,4-i]purin-6(7H)-yl)pentanenitrile

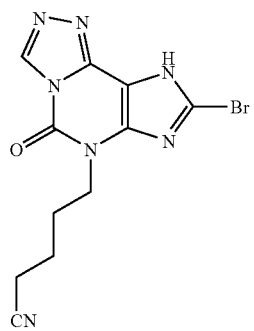

The title compound was prepared using procedures analogous to those described for example 32. LCMS calculated for $C_{11}H_{11}BrN_7O$ (M+H): 336.0. found 336.0, 338.0.

Example 34

8-bromo-6-(3,3,3-trifluoropropyl)-6,7-dihydro-5H-[1,2,4]triazolo[3,4-i]purin-5-one

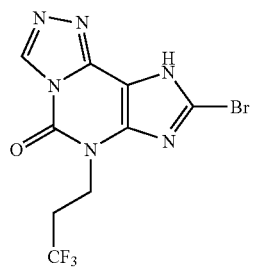

The title compound was prepared using procedures analogous to those described for example 32. LCMS calculated for $C_9H_7BrF_3N_6O$ (M+H): 351.0. found: 351.0, 353.0.

Example 35

8-bromo-6-(2-cyclohexylethyl)-6,9-dihydro-5H-[1,2,4]triazolo[3,4-i]purin-5-one

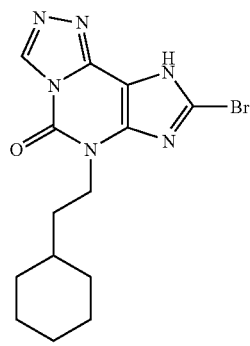

The title compound was prepared using procedures analogous to those described for example 32. LCMS calculated for $C_{14}H_{18}BrN_6O$ (M+H): 365.1. found 365.1, 367.1.

Example 36

8-bromo-6-(3-methylbutyl)-6,9-dihydro-5H-[1,2,4]triazolo[3,4-i]purin-5-one

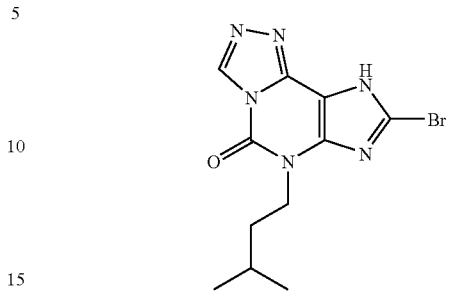

The title compound was prepared using procedures analogous to those described for example 32. $^1$HNMR (300 MHz, d$_6$-DMSO): δ 8.49 (s, 1H), 4.62 (t, J=6.5 Hz, 2H), 1.81 (m, 1H), 1.74 (m, 2H), 0.95 (t, J=6.5 Hz, 3H). LCMS calculated for $C_{11}H_{14}BrN_6O$ (M+H): 325.0. found 325.0, 327.0.

Example 37

Preparation of 2-bromo-8-methyl-4-(4,4,4-trifluorobutyl)-1,4-dihydro-5H-[1,2,4]triazolo[5,1-i]purin-5-one

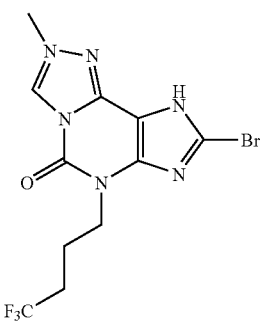

The title compound was prepared using procedures analogous to those described for Example 26. $^1$HNMR (400 MHz, d$_6$-DMSO): δ 4.21 (t, J=7.2 Hz, 2H), 2.1 (s, 3H), 2.38 (m, 2H), 1.95 (m, 2H). LCMS calculated for $C_{11}H_{11}BrF_3N_6O$ (M+H): 379.0, 381.0. found: 379.0, 381.0.

Example 38

Preparation of 2-bromo-8-methyl-4-(5,5,5-trifluoropentyl)-1,4-dihydro-5H-[1,2,4]triazolo[5,1-i]purin-5-one

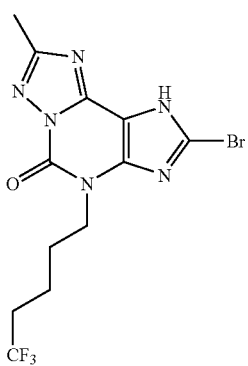

The title compound was prepared using procedures analogous to those described for Example 26. LCMS calculated for $C_{12}H_{13}BrF_3N_6O$ (M+H): 393.0, 395.0. found: 393.0, 395.0.

Example 39

Preparation of 2-bromo-8-methyl-4-(3,3,3-trifluoropropyl)-1,4-dihydro-5H-[1,2,4]triazolo[5,1-i]purin-5-one

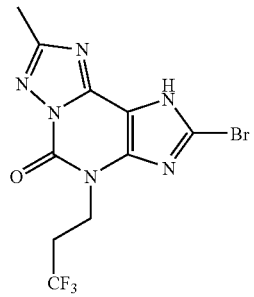

The title compound was prepared using procedures analogous to those described for Example 26. LCMS calculated for $C_{10}H_9BrF_3N_6O$ (M+H): 365.0, 367.0. found: 365.0, 367.0.

Example 40

Preparation of 2-bromo-4-(4-fluorobutyl)-8-methyl-1,4-dihydro-5H-[1,2,4]triazolo[5,1-i]purin-5-one

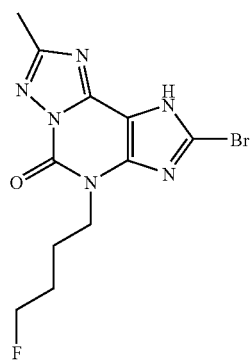

The title compound was prepared using procedures analogous to those described for Example 26. LCMS calculated for $C_{11}H_{13}BrFN_6O$ (M+H): 343.0, 345.0. found: 343.0, 345.0.

Example 41

Preparation of 2-bromo-4-(5-fluoropentyl)-8-methyl-1,4-dihydro-5H-[1,2,4]triazolo[5,1-i]purin-5-one

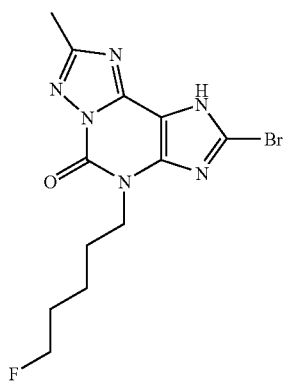

The title compound was prepared using procedures analogous to those described for Example 26. LCMS calculated for $C_{12}H_{15}BrFN_6O$ (M+H): 357.0, 359.0. found: 357.0, 359.0.

Example 42

Preparation of 2-bromo-4-(3-fluoropropyl)-8-methyl-1,4-dihydro-5H-[1,2,4]triazolo[5,1-i]purin-5-one

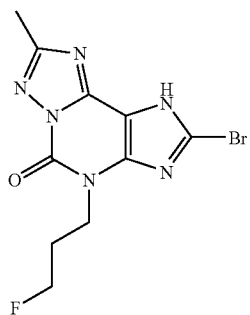

The title compound was prepared using procedures analogous to those described for Example 26. LCMS calculated for $C_{10}H_{11}BrFN_6O$ (M+H): 329.0, 331.0. found: 329.0, 331.0.

Example 43

Preparation of 2-bromo-4-butyl-8-(4-methoxyphenyl)-1,4-dihydro-5H-[1,2,4]triazolo[5,1-i]purin-5-one

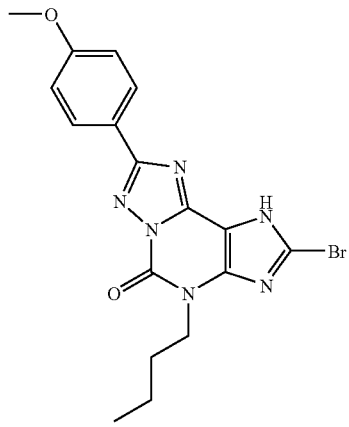

The title compound was prepared using procedures analogous to those described for Example 26. LCMS calculated for $C_{17}H_{18}BrN_6O_2$ (M+H): 417.1, 419.1. found: 417.0, 419.0.

Example 44

Preparation of 2-bromo-4-butyl-8-(4-hydroxyphenyl)-1,4-dihydro-5H-[1,2,4]triazolo[5,1-i]purin-5-one

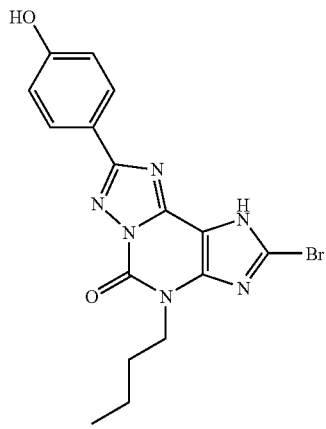

The title compound was prepared using procedures analogous to those described for Example 26. LCMS calculated for $C_{16}H_{16}BrN_6O_2$ (M+H): 403.0, 405.0. found: 403.0, 405.0.

Example 45

Preparation of 2-bromo-4-butyl-8-(4-methoxybenzyl)-1,4-dihydro-5H-[1,2,4]triazolo[5,1-i]purin-5-one

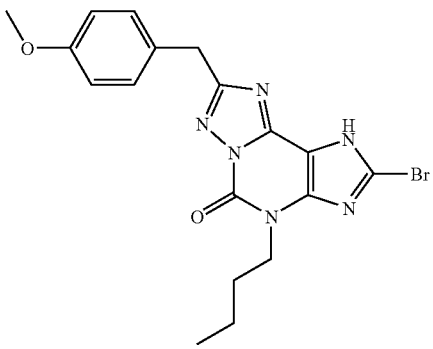

The title compound was prepared using procedures analogous to those described for Example 26. LCMS calculated for $C_{18}H_{20}BrN_6O_2$ (M+H): 431.1, 433.1. found: 431.0, 433.0.

Example 46

Preparation of 2-bromo-4-butyl-8-(4-hydroxybenzyl)-1,4-dihydro-5H-[1,2,4]triazolo[5,1-i]purin-5-one

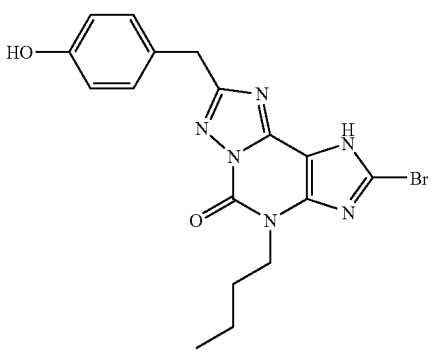

The title compound was prepared using procedures analogous to those described for Example 26. LCMS calculated for $C_{17}H_{18}BrN_6O_2$ (M+H): 417.1, 419.1. found: 417.0, 419.0.

Example 47

Preparation of 2-bromo-4-butyl-8-(methoxymethyl)-1,4-dihydro-5H-[1,2,4]triazolo[5,1-i]purin-5-one

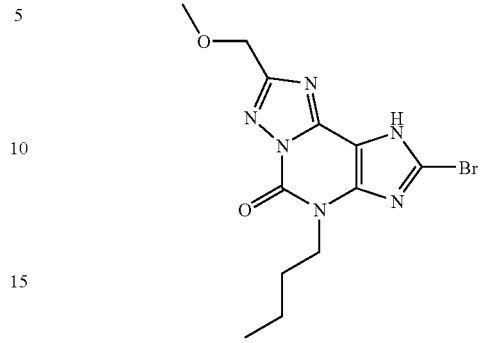

The title compound was prepared using procedures analogous to those described for Example 26. LCMS calculated for $C_{12}H_{16}BrN_6O_2$ (M+H): 355.0, 357.0. found: 355.0, 357.0.

Example A

GTPγS Recruitment Assay

Membranes were prepared from HEK293 cells transiently transfected with human HM74a and $G_{\alpha o}$ protein. Assays were performed in 384-well format in a volume of 50 µL per assay point. Serial dilutions of compounds were prepared in the assay buffer (20 mM HEPES pH. 7.4, 100 mM NaCl, 10 mM $MgCl_2$, 10 mg/L saponin and 10 µM GDP) and mixed with membranes (2 µg per assay point) and $^{35}S$ GTPγS (Amersham, 0.3 nM) in the assay buffer. The mixtures were incubated at room temperature for 30 min and wheat germ agglutinin SPA beads (Amersham) (0.2 mg per assay point) in the assay buffer were added. After 30 min incubation with agitation, plates were centrifuged at 1500 g for 5 min and bound $^{35}S$ GTPγS was determined by counting on a TopCount scintillation counter. An active compound according to this assay has an $EC_{50}$ of about 50 µM or less. In some embodiments, the compounds of the present invention have an $EC_{50}$ of less than about 50 µM, less than about 40 µM, less than about 30 µM, less than about 20 µM, less than about 10 µM, less than about 5 µM, less than about 1 µM, less than about 500 nM, less than 300 nM, or less than about 200 nM. For example, the compound of Example 1 has an $EC_{50}$ of 61 nM in this assay.

Example B

Nicotinic Acid Displacement Assay

Membranes were prepared from HEK293 cells transiently transfected with the human HM74a and $G_{\alpha o}$ protein. Wheat germ agglutinin SPA beads (Amersham) were weighed and suspended in the assay buffer (50 mM Tris-HCl, pH. 7.5, 1 mM $MgCl_2$ and 0.02% CHAPS). The beads were mixed with membrane (75 µg membrane/mg beads) at room temperature for 1 hr. The beads were spun down and washed once with buffer and then resuspended in buffer at 5 mg beads/ml. 20 nM of $^3H$ nicotinic acid was added to the beads and then mixed with compounds at (total vol. of 50 µL). Nonspecific binding was determined by the inclusion of 100 µM nicotinic acid. The binding mixtures were incubated at room temperature for overnight with agitation. Plates were centrifuged at 1500 g for 5 min and bound $^3H$ nicotinic acid was determined by counting on a TopCount scintillation counter. An active compound according to this assay has an $IC_{50}$ of about 50 µM or less. In some embodiments, the compounds of the present invention have an $IC_{50}$ of less than about 50 µM, less than about 40 µM, less than about 30 µM, less than about 20 µM, less than about 10 µM, less than about 5 µM, less than about 1 µM, less than about 500 nM, less than 300 nM, or less than about 200 nM.

Example C

FLIPR Assay

HEK293e cells transfected with human HM74a and $G_{\alpha 16}$ DNA were seeded the day before the assay at 50,000 cells/well in 384-well plates. Cells were washed once with 1×HBSS and incubated with FLIPR Calcium 3 (Molecular Devices) dye in 1×HBSS buffer containing 3 mM probenecid at 37° C. and 5% $CO_2$ for 60 min. Compounds were added to the cell plate and fluorescence changes due to $G_{\alpha 16}$-mediated intracellular calcium response were measured. An active compound according to this assay has an $EC_{50}$ of about 50 μM or less. In some embodiments, the compounds of the present invention have an $EC_{50}$ of less than about 50 μM, less than about 40 μM, less than about 30 μM, less than about 20 μM, less than about 10 μM, less than about 5 μM, less than about 1 μM, less than about 500 nM, less than 300 nM, or less than about 200 nM.

Example D cAMP Assay

CHO cells stably transfected with human HM74a were seeded at 7,500 cells/well in a 96-well plate in HAMS F12 medium with 10% FBS. The plate was incubated overnight at 37° C. and 5% $CO_2$. The test compounds were prepared in a stimulation buffer containing 1×HANKS, 20 mM HEPES, 5 μM forskolin, and 0.25 mM IBMX. The media from the cell plate was removed before adding 30 μL of the test compounds. After 30 minute incubation at 37° C. and 5% $CO_2$, the cAMP level was assayed using HitHunter cAMP XS assay kit (DiscoverX, CA). $IC_{50}$ determinations were based on compound inhibition relative to DMSO controls. An active compound according to this assay has an $IC_{50}$ of about 100 μM or less. In some embodiments, the compounds of the present invention have an $IC_{50}$ of less than about 100 μM, less than about 80 μM, less than about 60 μM, less than about 40 μM, less than about 30 μM, less than about 20 μM, less than about 10 μM, less than about 5 μM, less than about 1 μM, less than about 500 nM, less than 300 nM, or less than about 200 nM. For example, the compound of Example 1 has an $IC_{50}$ of 20 nM in this assay.

Example E

Adipocyte Lipolysis Assay

Preadipocytes purchased from Zen Bio were plated at 8.7×$10^4$ cells/well in 96-well plates, differentiated for 14 days and mature adipocytes assayed during days 15 through 21. Adipocyte maturation is assessed by the presence of rounded cells with large lipid droplets in the cytoplasm. Following maturation, cells were washed and incubated overnight with IBMX (100 μM) and various concentrations of compound diluted in assay buffer containing a final DMSO concentration of 0.1%. After overnight culture, the glycerol concentration in the supernatants was determined with the Lipolysis Assay Kit purchased from Zen-Bio. Absorbance at 540 nm is directly proportional to the glycerol concentration in the sample. $IC_{50}$ determinations were based on compound inhibition relative to DMSO controls. An active compound according to this assay has an $IC_{50}$ of about 10 μM or less. In some embodiments, the compounds of the present invention have an $IC_{50}$ of less than about 10 μM, less than about 5 μM, less than about 2 μM, less than about 1 μM, less than about 500 nM, less than 300 nM, less than 200 nM, less than 100 nM, or less than about 50 nM. For example, the compound of Example 1 has an $IC_{50}$ of 100 nM in this assay.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula IIa1:

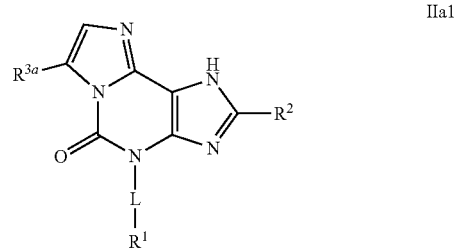

or pharmaceutically acceptable salt thereof, wherein:
- -L-$R^1$ is $C_{2-7}$ alkyl optionally substituted with 1, 2, 3, 4 or 5 substituents each independent selected from halo, cycloalkyl, OH, and CN;
- $R^2$ is halo or $C_1$ haloalkyl;
- $R^{3a}$ is selected from H, $C_{1-6}$ alkyl, $C_{1-6}$ haloalkyl, $Cy^1$, $OR^a$, $SR^a$, $S(O)R^b$, $S(O)_2R^b$, and $NR^cR^d$, wherein said $C_{1-6}$ alkyl is optionally substituted with 1, 2, or 3 substituents independently selected from $Cy^1$, $C(O)NR^cR^d$, $C(O)OR^a$, halo, $OR^a$, $NR^cR^d$, $NR^cC(O)NR^cR^d$, and $NR^cC(O)R^b$;
- $Cy^1$ and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $-(L^B)_{t1}$-$Cy^3$, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, and $S(O)_2NR^{c4}R^{d4}$;
- $Cy^3$ is independently selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;
- $R^a$ is independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;
- $R^{a4}$, $R^{a5}$, and $R^{a6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^b$ is independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{b4}$, $R^{b5}$, and $R^{b6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^c$ and $R^d$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^c$ and $R^d$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c4}$ and $R^{d4}$ together with the N atom to which they are attached form a 4-, 5-, 6- or 7-membered heterocycloalkyl group;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c5}$ and $R^{d5}$ together with the N atom to which they are attached form a 4-, 5-, 6- or 7-membered heterocycloalkyl group;

$R^{c6}$ and $R^{d6}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c6}$ and $R^{d6}$ together with the N atom to which they are attached form a 4-, 5-, 6- or 7-membered heterocycloalkyl group;

$L^B$ is $C_{1-4}$ alkylene optionally substituted with 1, 2, 3, 4 or 5 substituents independently selected from OH, halo, —O—($C_{1-4}$ alkyl), —O—($C_{1-4}$ haloalkyl), and amino; and t1 is 0 or 1.

2. The compound of claim 1 or pharmaceutically acceptable salt thereof wherein $-L-R^1$ is $C_{2-7}$ alkyl optionally substituted with 1, 2, 3, 4 or 5 halo.

3. The compound of claim 1 or pharmaceutically acceptable salt thereof wherein $-L-R^1$ is propyl, butyl, or pentyl.

4. The compound of claim 1 or pharmaceutically acceptable salt thereof wherein $R^2$ is halo.

5. The compound of claim 1 or pharmaceutically acceptable salt thereof wherein $R^2$ is Br or Cl.

6. The compound of claim 1 or pharmaceutically acceptable salt thereof wherein $R^2$ is $C_1$ haloalkyl.

7. The compound of claim 1 or pharmaceutically acceptable salt thereof wherein $R^2$ is $CF_3$.

8. The compound of claim 1 or pharmaceutically acceptable salt thereof wherein $R^{3a}$ is selected from H, $C_{1-3}$ alkyl, and $C_{1-3}$ haloalkyl.

9. The compound of claim 1 or pharmaceutically acceptable salt thereof wherein $R^{3a}$ is selected from H and methyl.

10. The compound of claim 1 or pharmaceutically acceptable salt thereof wherein $R^{3a}$ is methyl.

11. The compound of claim 1 or pharmaceutically acceptable salt thereof, wherein:

$R^{3a}$ is $C_{1-3}$ alkyl substituted with $Cy^1$ and optionally substituted with 1 or 2 substitutents independently selected from halo, $OR^a$, and $SR^a$;

$Cy^1$ is selected from aryl and heteroaryl each substituted with $R^7$ and optionally substituted by 1, 2, or 3 $R^8$;

$R^7$ is, at each occurrence, independently selected from $Cy^3$ and $-L^B-Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, NO$_2$, NR$^{c6}$R$^{d6}$, OR$^{a6}$, and SR$^{a6}$.

12. The compound of claim 1 or pharmaceutically acceptable salt thereof, wherein:
R$^{3a}$ is Cy$^1$;
Cy$^1$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, -(L$^B$)$_{r1}$-Cy$^3$, OR$^{a4}$, SR$^{a4}$, C(O)R$^{b4}$, C(O)NR$^{c4}$R$^{d4}$, and C(O)OR$^{a4}$; and
Cy$^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, NO$_2$, NR$^{c6}$R$^{d6}$, OR$^{a6}$, and SR$^{a6}$.

13. The compound of claim 1 or pharmaceutically acceptable salt thereof, wherein R$^{3a}$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, OR$^{a4}$, SR$^{a4}$, C(O)R$^{b4}$, C(O)NR$^{c4}$R$^{d4}$, and C(O)OR$^{a4}$.

14. A compound of Formula IIb1:

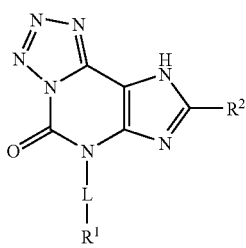

IIb1 or pharmaceutically acceptable salt thereof, wherein:
-L-R$^1$ is $C_{1-7}$ alkyl optionally substituted with 1, 2, 3, 4 or 5 substituents each independent selected from halo, cycloalkyl, OH, and CN; and
R$^2$ is halo.

15. The compound of claim 14 or pharmaceutically acceptable salt thereof, wherein -L-R$^1$ is $C_{2-7}$ alkyl optionally substituted with 1, 2, 3, 4 or 5 halo.

16. The compound of claim 14 or pharmaceutically acceptable salt thereof, wherein -L-R$^1$ is propyl, butyl, or pentyl.

17. The compound of claim 14 or pharmaceutically acceptable salt thereof, wherein -L-R$^1$ is butyl or pentyl.

18. The compound of claim 14 or pharmaceutically acceptable salt thereof, wherein R$^2$ is Cl or Br.

19. A compound of Formula IIIa:

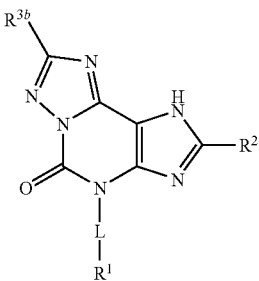

IIIa or pharmaceutically acceptable salt thereof, wherein:
-L-R$^1$ is $C_{1-7}$ alkyl optionally substituted with 1, 2, 3, 4 or 5 substitutents each independent selected from halo, cycloalkyl, OH, and CN;

R$^2$ is halo or $C_1$ haloalkyl;
R$^{3b}$ is selected from H, $C_{1-6}$ alkyl, $C_{1-6}$ haloalkyl, Cy$^1$, OR$^a$, SR$^a$, S(O)R$^b$, S(O)$_2$R$^b$, and NR$^c$R$^d$, wherein said $C_{1-6}$ alkyl is optionally substituted with 1, 2, or 3 substitutents independently selected from Cy$^1$, C(O)NR$^c$R$^d$, C(O)OR$^a$, halo, OR$^a$, NR$^c$R$^d$, NR$^c$C(O)NR$^c$R$^d$, and NR$^c$C(O)R$^b$;
Cy$^1$ and Cy$^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, -(L$^B$)$_{r1}$-Cy$^3$, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, S(O)R$^{b4}$, S(O)NR$^{c4}$R$^{d4}$, S(O)$_2$R$^{b4}$, and S(O)$_2$NR$^{c4}$R$^{d4}$;
Cy$^3$ is independently selected from aryl, heteroaryl, cycloalkyl, and heterocycloalkyl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, S(O)R$^{b6}$, S(O)NR$^{c6}$R$^{d6}$, S(O)$_2$R$^{b6}$, and S(O)$_2$NR$^{c6}$R$^{d6}$;
R$^a$ is independently selected from H, $C_{1-6}$ alkyl, $C_{1-6}$ haloalkyl, $C_{2-6}$ alkenyl, $C_{2-6}$ alkynyl, and Cy$^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;
R$^{a4}$, R$^{a5}$, and R$^{a6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;
R$^b$ is independently selected from H, $C_{1-6}$ alkyl, $C_{1-6}$ haloalkyl, $C_{2-6}$ alkenyl, $C_{2-6}$ alkynyl, and Cy$^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;
R$^{b4}$, R$^{b5}$, and R$^{b6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^c$ and $R^d$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^c$ and $R^d$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c4}$ and $R^{d4}$ together with the N atom to which they are attached form a 4-, 5-, 6- or 7-membered heterocycloalkyl group;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c5}$ and $R^{d5}$ together with the N atom to which they are attached form a 4-, 5-, 6- or 7-membered heterocycloalkyl group;

$R^{c6}$ and $R^{d6}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c6}$ and $R^{d6}$ together with the N atom to which they are attached form a 4-, 5-, 6- or 7-membered heterocycloalkyl group;

$L^B$ is $C_{1-4}$ alkylene optionally substituted with 1, 2, 3, 4 or 5 substituents independently selected from OH, halo, —O—($C_{1-4}$ alkyl), —O—($C_{1-4}$ haloalkyl), and amino; and t1 is 0 or 1.

20. The compound of claim 19 or pharmaceutically acceptable salt thereof, wherein -L-$R^1$ is $C_{2-7}$ alkyl optionally substituted with 1, 2, 3, 4 or 5 substitutents each independent selected from halo, cycloalkyl, OH, and CN.

21. The compound of claim 19 or pharmaceutically acceptable salt thereof, wherein -L-$R^1$ is $C_{2-7}$ alkyl optionally substituted with 1, 2, 3, 4 or 5 halo.

22. The compound of claim 19 or pharmaceutically acceptable salt thereof, wherein $R^2$ is halo.

23. The compound of claim 19 or pharmaceutically acceptable salt thereof, wherein $R^2$ is Br or Cl.

24. The compound of claim 19 or pharmaceutically acceptable salt thereof wherein $R^2$ is $C_1$ haloalkyl.

25. The compound of claim 19 or pharmaceutically acceptable salt thereof wherein $R^2$ is $CF_3$.

26. The compound of claim 19 or pharmaceutically acceptable salt thereof wherein:

$R^{3b}$ is $C_{1-3}$ alkyl substituted with $Cy^1$ and optionally substituted with 1 or 2 substituents independently selected from halo, $OR^a$, and $SR^a$;

$Cy^1$ is selected from aryl and heteroaryl each substituted with $R^7$ and optionally substituted by 1, 2, or 3 $R^8$;

$R^7$ is, at each occurrence, independently selected from $Cy^3$ and -$L^B$-$Cy^3$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

27. The compound of claim 19 or pharmaceutically acceptable salt thereof wherein:

$R^{3b}$ is selected from $C_{1-3}$ alkyl, wherein said $C_{1-3}$ alkyl is substituted with —O-$Cy^2$ and optionally substituted with 1 or 2 substituents independently selected from halo, $OR^a$, and $SR^a$;

$Cy^2$ is selected from aryl and heteroaryl, each substituted with $Cy^3$ and optionally substituted by 1, 2, or 3 $R^8$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

28. The compound of claim 19 or pharmaceutically acceptable salt thereof, wherein:

$R^{3b}$ is $Cy^1$;

$Cy^1$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, -($L^B$)$_{t1}$-$Cy^3$, $OR^{a4}$, $SR^{a4}$, $C(O)R^{b4}$, $C(O)NR^{c4}R^{d4}$, and $C(O)OR^{a4}$; and $Cy^3$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

29. The compound of claim 19 or pharmaceutically acceptable salt thereof, wherein $R^{3b}$ is selected from aryl and heteroaryl, each optionally substituted with 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^{c4}R^{d4}$, and $C(O)OR^{a4}$.

30. A compound selected from:
    6-pentyl-8-(trifluoromethyl)-6,9-dihydro-5H-[1,2,4]triazolo[3,4-i]purin-5-one;
    6-butyl-8-(trifluoromethyl)-6,9-dihydro-5H-[1,2,4]triazolo[3,4-i]purin-5-one;
    6-butyl-3-methyl-8-(trifluoromethyl)-6,9-dihydro-5H-[1,2,4]triazolo[3,4-i]purin-5-one;
    8-bromo-6-pentyl-6,9-dihydro-5H-[1,2,4]triazolo[3,4-i]purin-5-one;
    8-bromo-6-butyl-6,9-dihydro-5H-[1,2,4]triazolo[3,4-i]purin-5-one;
    8-bromo-6-butyl-3-methyl-6,9-dihydro-5H-[1,2,4]triazolo[3,4-i]purin-5-one;
    8-bromo-6-pentyl-6,9-dihydro-5H-tetrazolo[5,1-i]purin-5-one;
    2-bromo-4-pentyl-8-phenyl-1,4-dihydro-5H-[1,2,4]triazolo[5,1-i]purin-5-one;
    2-bromo-8-methyl-4-pentyl-1,4-dihydro-5H-[1,2,4]triazolo[5,1-i]purin-5-one;
    2-bromo-4-pentyl-8-pyridin-4-yl-1,4-dihydro-5H-[1,2,4]triazolo[5,1-i]purin-5-one;
    2-bromo-4-pentyl-8-pyridin-3-yl-1,4-dihydro-5H-[1,2,4]triazolo[5,1-i]purin-5-one;
    8-bromo-3-methyl-6-pentyl-6,9-dihydro-5H-[1,2,4]triazolo[3,4-i]purin-5-one;
    8-benzyl-2-bromo-4-pentyl-1,4-dihydro-5H-[1,2,4]triazolo[5,1-i]purin-5-one;
    2-bromo-4-pentyl-8-pyrimidin-4-yl-1,4-dihydro-5H-[1,2,4]triazolo[5,1-i]purin-5-one;
    8-bromo-6-pentyl-3-pyrimidin-4-yl-6,9-dihydro-5H-[1,2,4]triazolo[3,4-i]purin-5-one;
    2-bromo-4-pentyl-8-(trifluoromethyl)-1,4-dihydro-5H-[1,2,4]triazolo[5,1-i]purin-5-one;
    8-bromo-6-pentyl-3-(trifluoromethyl)-6,9-dihydro-5H-[1,2,4]triazolo[3,4-i]purin-5-one;
    8-chloro-6-pentyl-3-pyrimidin-4-yl-6,9-dihydro-5H-[1,2,4]triazolo[3,4-i]purin-5-one;
    2-chloro-8-methyl-4-pentyl-1,4-dihydro-5H-[1,2,4]triazolo[5,1-i]purin-5-one;
    2-chloro-4-pentyl-8-pyrimidin-4-yl-1,4-dihydro-5H-[1,2,4]triazolo[5,1-i]purin-5-one;
    8-[2-(3-benzyl-1,2,4-oxadiazol-5-yl)ethyl]-2-bromo-4-butyl-1,4-dihydro-5H-[1,2,4]triazolo[5,1-i]purin-5-one;
    8-[2-(3-benzyl-1,2,4-oxadiazol-5-yl)ethyl]-4-butyl-2-chloro-1,4-dihydro-5H-[1,2,4]triazolo[5,1-i]purin-5-one;
    2-bromo-4-butyl-8-[(4-pyridin-4-ylphenoxy)methyl]-1,4-dihydro-5H-[1,2,4]triazolo[5,1-i]purin-5-one;
    4'-[(2-bromo-4-butyl-5-oxo-4,5-dihydro-1H-[1,2,4]triazolo[5,1-i]purin-8-yl)methoxy]biphenyl-3-carbonitrile;
    2-bromo-4-butyl-8-[(4-pyridin-3-ylphenoxy)methyl]-1,4-dihydro-5H-[1,2,4]triazolo[5,1-i]purin-5-one;
    2-bromo-4-pentyl-1,4-dihydro-5H-[1,2,4]triazolo[5,1-i]purin-5-one;
    2-bromo-4-butyl-8-methyl-1,4-dihydro-5H-[1,2,4]triazolo[5,1-i]purin-5-one;
    2-chloro-8-methyl-4-propyl-1,4-dihydro-5H-[1,2,4]triazolo[5,1-i]purin-5-one;
    2-bromo-8-methyl-4-propyl-1,4-dihydro-5H-[1,2,4]triazolo[5,1-i]purin-5-one;
    4-butyl-2-chloro-8-methyl-1,4-dihydro-5H-[1,2,4]triazolo[5,1-i]purin-5-one;
    8-bromo-6-pentyl-3-methyl-6,9-dihydro-5H-[1,2,4]triazolo[3,4-i]purin-5-one;
    8-bromo-6-isobutyl-6,7-dihydro-5H-[1,2,4]triazolo[3,4-i]purin-5-one;
    5-(8-bromo-5-oxo-5H-[1,2,4]triazolo[3,4-i]purin-6(7H)-yl)pentanenitrile;
    8-bromo-6-(3,3,3-trifluoropropyl)-6,7-dihydro-5H-[1,2,4]triazolo[3,4-i]purin-5-one;
    8-bromo-6-(2-cyclohexylethyl)-6,9-dihydro-5H-[1,2,4]triazolo[3,4-i]purin-5-one;
    8-bromo-6-(3-methylbutyl)-6,9-dihydro-5H-[1,2,4]triazolo[3,4-i]purin-5-one;
    2-bromo-8-methyl-4-(4,4,4-trifluorobutyl)-1,4-dihydro-5H-[1,2,4]triazolo[5,1-i]purin-5-one;
    2-bromo-8-methyl-4-(5,5,5-trifluoropentyl)-1,4-dihydro-5H-[1,2,4]triazolo[5,1-i]purin-5-one;
    2-bromo-8-methyl-4-(3,3,3-trifluoropropyl)-1,4-dihydro-5H-[1,2,4]triazolo[5,1-i]purin-5-one;
    2-bromo-4-(4-fluorobutyl)-8-methyl-1,4-dihydro-5H-[1,2,4]triazolo[5,1-i]purin-5-one;
    2-bromo-4-(5-fluoropentyl)-8-methyl-1,4-dihydro-5H-[1,2,4]triazolo[5,1-i]purin-5-one;
    2-bromo-4-(3-fluoropropyl)-8-methyl-1,4-dihydro-5H-[1,2,4]triazolo[5,1-i]purin-5-one;
    bromo-4-butyl-8-(4-methoxyphenyl)-1,4-dihydro-5H-[1,2,4]triazolo[5,1-i]purin-5-one;
    2-bromo-4-butyl-8-(4-hydroxyphenyl)-1,4-dihydro-5H-[1,2,4]triazolo[5,1-i]purin-5-one;
    2-bromo-4-butyl-8-(4-methoxybenzyl)-1,4-dihydro-5H-[1,2,4]triazolo[5,1-i]purin-5-one;
    2-bromo-4-butyl-8-(4-hydroxybenzyl)-1,4-dihydro-5H-[1,2,4]triazolo[5,1-i]purin-5-one; and
    2-bromo-4-butyl-8-(methoxymethyl)-1,4-dihydro-5H-[1,2,4]triazolo[5,1-i]purin-5-one,
  or pharmaceutically acceptable salt thereof.

31. The compound of claim 30 or pharmaceutically acceptable salt thereof that is a compound selected from:
    6-pentyl-8-(trifluoromethyl)-6,9-dihydro-5H-[1,2,4]triazolo[3,4-i]purin-5-one;
    6-butyl-8-(trifluoromethyl)-6,9-dihydro-5H-[1,2,4]triazolo[3,4-i]purin-5-one;
    6-butyl-3-methyl-8-(trifluoromethyl)-6,9-dihydro-5H-[1,2,4]triazolo[3,44]purin-5-one;
    8-bromo-6-pentyl-6,9-dihydro-5H-[1,2,4]triazolo[3,4-i]purin-5-one;
    8-bromo-6-butyl-6,9-dihydro-5H-[1,2,4]triazolo[3,4-i]purin-5-one;
    8-bromo-6-butyl-3-methyl-6,9-dihydro-5H-[1,2,4]triazolo[3,4-i]purin-5-one;
    8-bromo-6-pentyl-6,9-dihydro-5H-tetrazolo[5,1-i]purin-5-one;
    2-bromo-4-pentyl-8-phenyl-1,4-dihydro-5H-[1,2,4]triazolo[5,1-i]purin-5-one;
    2-bromo-4-pentyl-8-pyridin-4-yl-1,4-dihydro-5H-[1,2,4]triazolo[5,1-i]purin-5-one;
    2-bromo-4-pentyl-8-pyridin-3-yl-1,4-dihydro-5H-[1,2,4]triazolo[5,1-i]purin-5-one;
    8-bromo-3-methyl-6-pentyl-6,9-dihydro-5H-[1,2,4]triazolo[3,4-i]purin-5-one;
    2-bromo-4-pentyl-8-pyrimidin-4-yl-1,4-dihydro-5H-[1,2,4]triazolo[5,1-i]purin-5-one;

8-bromo-6-pentyl-3-pyrimidin-4-yl-6,9-dihydro-5H-[1,2,4]triazolo[3,4-i]purin-5-one;

8-bromo-6-pentyl-3-(trifluoromethyl)-6,9-dihydro-5H-[1,2,4]triazolo[3,4-i]purin-5-one ;

8-chloro-6-pentyl-3-pyrimidin-4-yl-6,9-dihydro-5H-[1,2,4]triazolo[3,4-i]purin-5-one;

2-chloro-4-pentyl-8-pyrimidin-4-yl-1,4-dihydro-5H-[1,2,4]triazolo[5,1-i]purin-5-one;

8-bromo-6-pentyl-3-methyl-6,9-dihydro-5H-[1,2,4]triazolo[3,4-i]purin-5-one;

8-bromo-6-isobutyl-6,7-dihydro-5H-[1,2,4]triazolo[3,4-i]purin-5-one;

5-(8-bromo-5-oxo-5H-[1,2,4]triazolo[3,4-i]purin-6(7H)-yl)pentanenitrile;

8-bromo-6-(3,3,3-trifluoropropyl)-6,7-dihydro-5H-[1,2,4]triazolo[3,4-i]purin-5-one;

8-bromo-6-(2-cyclohexylethyl)-6,9-dihydro-5H-[1,2,4]triazolo[3,4-i]purin-5-one;

8-bromo-6-(3-methylbutyl)-6,9-dihydro-5H-[1,2,4]triazolo[3,4-i]purin-5-one;

2-bromo-4-butyl-8-(4-methoxyphenyl)-1,4-dihydro-5H-[1,2,4]triazolo[5,1-i]purin-5-one; and 2-bromo-4-butyl-8-(4-hydroxyphenyl)-1,4-dihydro-5H-[1,2,4]triazolo[5,1-i]purin-5-one, or pharmaceutically acceptable salt thereof.

32. A composition comprising a compound of claim 1 or pharmaceutically acceptable salt thereof, and at least one pharmaceutically acceptable carrier.

33. A composition comprising a compound of claim 14 or pharmaceutically acceptable salt thereof, and at least one pharmaceutically acceptable carrier.

34. A composition comprising a compound of claim 19 or pharmaceutically acceptable salt thereof, and at least one pharmaceutically acceptable carrier.

35. A composition comprising a compound of claim 30 or pharmaceutically acceptable salt thereof, and at least one pharmaceutically acceptable carrier.

36. A composition comprising a compound of claim 31 or pharmaceutically acceptable salt thereof, and at least one pharmaceutically acceptable carrier.

* * * * *